(12) United States Patent
Heijstra et al.

(10) Patent No.: US 10,494,600 B2
(45) Date of Patent: *Dec. 3, 2019

(54) BACTERIA AND METHODS OF USE THEREOF

(71) Applicant: LanzaTech New Zealand Limited, Skokie, IL (US)

(72) Inventors: Bjorn Daniel Heijstra, Skokie, IL (US); Evgenia Kern, Auckland (NZ); Michael Koepke, Skokie, IL (US); Simon Segovia, Santiago (CL); Fungmin Liew, Nottingham (GB)

(73) Assignee: LANZATECH NEW ZEALAND LIMITED, Auckland (NZ)

(*) Notice: Subject to any disclaimer, the term of this patent is extended or adjusted under 35 U.S.C. 154(b) by 419 days.

This patent is subject to a terminal disclaimer.

(21) Appl. No.: 14/874,665

(22) Filed: Oct. 5, 2015

(65) Prior Publication Data

US 2016/0017276 A1 Jan. 21, 2016

Related U.S. Application Data

(63) Continuation of application No. 13/812,029, filed as application No. PCT/NZ2011/000144 on Jul. 28, 2011, now abandoned.

(60) Provisional application No. 61/368,486, filed on Jul. 28, 2010.

(51) Int. Cl.
| | |
|---|---|
| C12N 1/20 | (2006.01) |
| C12P 7/06 | (2006.01) |
| C12R 1/145 | (2006.01) |
| C12P 7/24 | (2006.01) |

(52) U.S. Cl.
CPC ............... *C12N 1/20* (2013.01); *C12P 7/065* (2013.01); *C12P 7/24* (2013.01); *C12R 1/145* (2013.01)

(58) Field of Classification Search
None
See application file for complete search history.

(56) References Cited

U.S. PATENT DOCUMENTS

| 5,173,429 A | 12/1992 | Gaddy |
| 5,593,886 A | 1/1997 | Gaddy |
| 6,368,819 B1 | 4/2002 | Gaddy |
| 2003/0211585 A1 | 11/2003 | Gaddy et al. |
| 2011/0250629 A1 | 10/2011 | Heijstra |
| 2013/0045517 A1 | 2/2013 | Oakley et al. |
| 2013/0224838 A1 | 8/2013 | Koepke et al. |
| 2013/0224839 A1 | 8/2013 | Koepke et al. |
| 2013/0236941 A1 | 9/2013 | Burns-Guydish et al. |
| 2013/0252083 A1 | 9/2013 | Stauffer |
| 2013/0256600 A1 | 10/2013 | Tsumori et al. |

FOREIGN PATENT DOCUMENTS

| WO | 1998/000558 | 1/1998 |
| WO | 2000/068407 | 11/2000 |
| WO | 2002/008438 | 1/2002 |
| WO | 2007/117157 | 10/2007 |
| WO | 2008/028055 | 3/2008 |
| WO | 2008/115080 | 9/2008 |
| WO | 2009/064200 | 5/2009 |
| WO | 2010/064933 | 6/2010 |
| WO | 2011/078709 | 6/2011 |
| WO | 2012/054798 | 4/2012 |

OTHER PUBLICATIONS

Abrini, *Clostridium autoethanogenum*, sp. nov., an anaerobic bacterium that produces ethanol from carbon monoxide, Arch Microbial, 161: 345-351, 1994.
Carver, Artemis and ACT: viewing, annotating and comparing sequences stored in a relational database, Bioinformatics, 24: 2672-2676, 2008.
Darling, Mauve: multiple alignment of conserved genomic sequence with rearrangements, Genome Res, 14: 1394-1403, 2004.
Hensirisak, Scale-Up of microbubble dispersion generator for aerobic fermentation, Appl Biochem Biotechnol, 101: 211-228, 2002.
International Search Report for International Patent Application PCT/NZ201/000144, Australian Patent Office, dated Nov. 1, 2011.
Klasson, Bioconversion of synthesis gas into liquid or gaseous fuels, Enzyme Microb Technol, 14: 602-608, 1992.
Lewis, Making the connection: conversion of biomass-generated producer gas to ethanol, Proceedings Bioenergy Conference, 1-8, 2002.
Najafpour, Ethanol and acetate synthesis from waste gas using batch culture of Clostridium Ijungdahlii, Enzyme Microb Technol, 38: 223-228, 2006.

*Primary Examiner* — Jennifer M. H. Tichy
(74) *Attorney, Agent, or Firm* — Andrea E Schoen

(57) ABSTRACT

The invention provides a novel bacterium with improved properties, including improved ethanol production, ethanol productivity, CO uptake, specific growth rate, ethanol to acetate ratio, and alcohol tolerance. The bacterium may be derived from *Clostridium autoethanogenum* and/or may comprise at least one DNA or amino acid sequence selected from SEQ ID NOs: 1, 3, 6, 8, 10, 12, 14, and 16. In one embodiment, the bacterium is *Clostridium autoethanogenum* deposited under DSMZ accession number DSM23693 or a bacterium derived therefrom.

13 Claims, 19 Drawing Sheets
Specification includes a Sequence Listing.

Track 1: coding sequences on leading strand;

Track 2: genes on lagging strand;

Track 3: rearrangement event compared to LZ1560;

Track 4: point mutations compared to LZ1560;

Track 5: deletions compared to LZ1560;

Track 6: insertions compared to LZ1560;

Track 7: GC plot;

Track 8: GC Skew.

GTGGCATTAACTCCAATGATGCAGCAGTATATGGAAGTAAAAGAAAGTTATAAAGACTGTATACTGTTTTTTA
GATTAGGTGATTTTTATGAAATGTTTTTTGAAGATGCAAAAATAGCATCTAGGGAACTAGAATTAGTACTTACA
GGTAGAGATTGCGGCTTAAAAGAAAGGGCTCCTATGTGTGGAATACCCTATCATGCCGCAAATTCATATATAG
GAAGGCTTATAAACAAGGGATATAAGATAGCTATATGTGAGCAACTAGAAGATCCAGCTCTAGCAAAAGGTA
TAGTTAAAAGGGGCATAATCAAGGTTGTAACTCCTGGGACTTATACGGACTCTACTTTTTTAGAAGAAAATAA
AAATAATTATATAGCGTGTTTGTACATAGATACCAAGACAAATATTTCTGCATTGTGTTTTGCAGATGTGTCCA
CTGGAGAATTCAATTGTACGGACACTCCTTTTAATTTATCTATAATTTTAGATGAAATATCAAAATACTCTCCAA
GTGAACTAGTGATTCAAGGTAGTATAAGTGCTGATTTATTGAATAAAATGAAGGATATTTTTAATGGCTCATTC
ACTAAATTAGATGAAAGCTATTTTGCAGACGAAACTAAAAATATATTAGAGGATCAGTTTGAAAATTTTACAG
GAGAAAATTATAGTAATGAAATTATAAAATGCTGCGGCTCACTACTAAAATATATAAGGGAAACTCAAAAGAA
TGATCTATCTCATATAAATAAATTTTCCTATTACAATATAGTAGATTATCTCACTATAGATGGGAATTCCAGAAG
AAATTTAGAAATTACAGAAAGCTTAAGAGAAAATAATAAAAAAGGATCTCTCCTCTGGGTTATAGATAAAACA
AATACATCTATGGGAGGGAGACAGCTTAGAAGATGGCTGGAACAGCCCCTTATAAATAAGGTTAAGATAGAA
GAAAGACTGGATTCTGTAGAGGAAATTTCAAATAATATATCCTATCATGAAGATCTAAAAGAGGCTTTAAAAA
ACATATATGATATTGAGCGATTAGTTGGAAAAATATCTTCTAAAAGTGTAAACGCAAAAGAACTAAATTTTTA
AAAAATTCTATAGAAAAAATACCTGAAGTAAAATCCATACTATCCAATTTTCATACAAAATTATTGAAGGATAT
GTACGAAAACTTGGATGAACTAAAGGACATATATTCACTTTTAGATAAATCTATATTAGATAATCCTGCAATAT
CTTTAAAAGAAGGTAACCTTATAAAAAAGGGATATAACAGTGACATAGATGAACTTAAAGAAATAAAGGCTC
ACGGTAAGGAGTGGATAGCTTCTCTTGAGAATTCAGAAAGGGAAGTTACTAAAATAAAATCTCTTAAAATAG
GTTATAATAAAGTATTTGGTTATTATATTGAGGTTACTAAAAGTAATTTAAGTCTTGTACCAGAAGGTAGATAT
ATAAGAAAACAAACTCTTACAAATGCAGAAAGATACATAACTCCTGAATTGAAAGAAATGGAAGATAAAATAT
TAGGTCTAGAATATAGTGTCTTTATAGAAGTAAGAGATAAAATAGAAAATGAAGTAGACAGAATGCAAAAAT
CCGCTAAAATAATTTCAGAAGTAGATTGCTTAAGCTCCCTTGCAAGAGTTGCTATAGAAAATAATTATTGTAAA
CCTGAAATAACAAATTCAGATAACATAATTATAGAAGAAGGTAGACATCCTGTAGTAGAAAAGATGATTGACT
CTGGAGAATTTATATCAAACGATATAAACATAGATACTGGTAAAAATCAACTTCTTTTAATAACAGGGCCTAAT
ATGGCAGGCAAATCTACCTACATGAGGCAGATAGCTTTGATCGTTATAATGGCCCAAATTGGTAGCTTTGTAC
CGGCAAAAAATGCTTCTATATCTGTTTGTGATAAGATATTTACAAGGATAGGTGCATCAGATGACCTGGCATC
AGGAAAGAGTACCTTTATGGTGGAAATGTGGGAGGTTTCCAACATACTTAAAAATGCAACTAACAAAAGTTTG
ATTTTACTGGATGAAGTAGGACGTGGAACAAGTACTTACGACGGCCTTAGCATAGCCTGGTCAGTAATAGAAT
ATATATGTAAAAACAGCAAACTAAAATGTAAAACCTTATTTGCAACCCATTATCATGAACTAACTAAATTAGAA
GGTAAGATAGATGGAGTCAAAAATTACTGTGTATCCGTTAAAGAAATGGAGGATAATATAGTTTTTTTGAGAA
AAATTATAAGAGGAGGAGCCGACCAATCCTACGGCATAGAAGTTGCAAAGCTTGCAGGGCTTCCAGAAGAAG
TTTTAAAAAGAGCAGGAGAAATACTAAATAGCCTTGAAAGTAAAAAGCTAAAAGAAAATAAATGTGTTGATTC
TGAAATTGCATTAGATTCAGAGTATTCAATAAATGAGAAAAAAGCACCTCTTAAAAATGAGGAGATGATTAAA
GAAAAAGCTCCTATGCTTGAACCAACCAGACAATTAGGATTTTCAGATATAGAAAAGACAAATTTAGTAAAAG
ATATTACGGATATAGATATACTAAACATGACTCCTATGGACGGATTTAATAAACTTTATGATATAATAAGAAGA
GCAAAGTCCATAAGATAA (SEQ ID NO: 1)

GTGGCATTAACTCCAATGATGCAGCAGTATATGGAAGTAAAAGAAAGTTATAAAGACTGTATACTGTTTTTTA
GATTAGGTGATTTTTATGAAATGTTTTTTGAAGATGCAAAAATAGCATCTAGGGAACTAGAATTAGTACTTACA
GGTAGAGATTGCGGCTTAAAAGAAAGGGCTCCTATGTGTGGAATACCCTATCATGCCGCAAATTCATATATAG
GAAGGCTTATAAACAAGGGATATAAGATAGCTATATGTGAGCAACTAGAAGATCCAGCTCTAGCAAAAGGTA
TAGTTAAAAGGGGCATAATCAAGGTTGTAACTCCTGGGACTTATACGGACTCTACTTTTTTAGAAGAAAATAA
AAATAATTATATAGCGTGTTTGTACATAGATACCAAGACAAATATTTCTGCATTGTGTTTTGCAGATGTGTCCA
CTGGAGAATTCAATTGTACGGACACTCCTTTTAATTTATCTATAATTTTAGATGAAATATCAAAATACTCTCCAA
GTGAACTAGTGATTCAAGGTAGTATAAGTGCTGATTTATTGAATAAAATGAAGGATATTTTTAATGGCTCATTC
ACTAAATTAGATGAAAGCTATTTTGCAGACGAAACTAAAAATATATTAGAGGATCAGTTTGAAAATTTTACAG
GAGAAAATTATAGTAATGAAATTATAAAATGCTGCGGCTCACTACTAAAATATATAAGGGAAACTCAAAAGAA
TGATCTATCTCATATAAATAAATTTTCCTATTACAATATAGTAGATTATCTCACTATAGATGGGAATTCCAGAAG
AAATTTAGAAATTACAGAAAGCTTAAGAGAAAATAATAAAAAAGGATCTCTCCTCTGGGTTATAGATAAAACA
AATACATCTATGGGAGGGAGACAGCTTAGAAGATGGCTGGAACAGCCCCTTATAAATAAGGTTAAGATAGAA
GAAAGACTGGATTCTGTAGAGGAAATTTCAAATAATATATCCTATCATGAAGATCTAAAAGAGGCTTTAAAAA
ACATATATGATATTGAGCGATTAGTTGGAAAAATATCTTCTAAAAGTGTAAACGCAAAAGAACTAAATTTTTTA
AAAAATTCTATAGAAAAATACCTGAAGTAAAATCCATACTATCCAATTTTCATACAAAATTATTGAAGGATAT
GTACGAAAACTTGGATGAACTAAAGGACATATATTCACTTTTAGATAAATCTATATTAGATAATCCTGCAATAT
CTTTAAAAGAAGGTAACCTTATAAAAAAGGGATATAACAGTGACATAGATGAACTTAAAGAAATAAAGGCTC
ACGGTAAGGAGTGGATAGCTTCTCTTGAGAATTCAGAAAGGGAAGTTACTAAAATAAAATCTCTTAAAATAG
GTTATAATAAAGTATTTGGTTATTATATTGAGGTTACTAAAAGTAATTTAAGTCTTGTACCAGAAGGTAGATAT
ATAAGAAAACAAACTCTTACAAATGCAGAAAGATACATAACTCCTGAATTGAAAGAAATGGAAGATAAAATAT
TAGGTGCAGAGGAAAAACTTATAAATCTAGAATATAGTGTCTTTATAGAAGTAAGAGATAAAATAGAAAATG
AAGTAGACAGAATGCAAAAATCCGCTAAAATAATTTCAGAAGTAGATTGCTTAAGCTCCCTTGCAAGAGTTGC
TATAGAAAATAATTATTGTAAACCTGAAATAACAAATTCAGATAACATAATTATAGAAGAAGGTAGACATCCT
GTAGTAGAAAAGATGATTGACTCTGGAGAATTTATATCAAACGATATAAACATAGATACTGGTAAAAATCAAC
TTCTTTTAATAACAGGGCCTAATATGGCAGGCAAATCTACCTACATGAGGCAGATAGCTTTGATCGTTATAATG
GCCCAAATTGGTAGCTTTGTACCGGCAAAAAATGCTTCTATATCTGTTTGTGATAAGATATTTACAAGGATAGG
TGCATCAGATGACCTGGCATCAGGAAAGAGTACCTTTATGGTGGAAATGTGGGAGGTTTCCAACATACTTAAA
AATGCAACTAACAAAAGTTTGATTTTACTGGATGAAGTAGGACGTGGAACAAGTACTTACGACGGCCTTAGCA
TAGCCTGGTCAGTAATAGAATATATATGTAAAAACAGCAAACTAAAATGTAAAACCTTATTTGCAACCCATTAT
CATGAACTAACTAAATTAGAAGGTAAGATAGATGGAGTCAAAAATTACTGTGTATCCGTTAAAGAAATGGAG
GATAATATAGTTTTTTTGAGAAAAATTATAAGAGGAGGAGCCGACCAATCCTACGGCATAGAAGTTGCAAAG
CTTGCAGGGCTTCCAGAAGAAGTTTTAAAAAGAGCAGGAGAAATACTAAATAGCCTTGAAAGTAAAAAGCTA
AAAGAAATAAATGTGTTGATTCTGAAATTGCATTAGATTCAGAGTATTCAATAAATGAGAAAAAAGCACCTC
TTAAAAATGAGGAGATGATTAAAGAAAAAGCTCCTATGCTTGAACCAACCAGACAATTAGGATTTTCAGATAT
AGAAAAGACAAATTTAGTAAAAGATATTACGGATATAGATATACTAAACATGACTCCTATGGACGGATTTAAT
AAACTTTATGATATAATAAGAAGAGCAAAGTCCATAAGATAA (SEQ ID NO: 2)

MALTPMMQQYMEVKESYKDCILFFRLGDFYEMFFEDAKIASRELELVLTGRDCGLKERAPMCGIPYHAANSYIGRL
INKGYKIAICEQLEDPALAKGIVKRGIIKVVTPGTYTDSTFLEENKNNYIACLYIDTKTNISALCFADVSTGEFNCTDTPF
NLSIILDEISKYSPSELVIQGSISADLLNKMKDIFNGSFTKLDESYFADETKNILEDQFENFTGENYSNEIIKCCGSLLKYIR
ETQKNDLSHINKFSYYNIVDYLTIDGNSRRNLEITESLRENNKKGSLLWVIDKTNTSMGGRQLRRWLEQPLINKVKIE
ERLDSVEEISNNISYHEDLKEALKNIYDIERLVGKISSKSVNAKELNFLKNSIEKIPEVKSILSNFHTKLLKDMYENLDELK
DIYSLLDKSILDNPAISLKEGNLIKKGYNSDIDELKEIKAHGKEWIASLENSEREVTKIKSLKIGYNKVFGYYIEVTKSNLSL
VPEGRYIRKQTLTNAERYITPELKEMEDKILGLEYSVFIEVRDKIENEVDRMQKSAKIISEVDCLSSLARVAIENNYCKP
EITNSDNIIIEEGRHPVVEKMIDSGEFISNDINIDTGKNQLLLITGPNMAGKSTYMRQIALIVIMAQIGSFVPAKNASIS
VCDKIFTRIGASDDLASGKSTFMVEMWEVSNILKNATNKSLILLDEVGRGTSTYDGLSIAWSVIEYICKNSKLKCKTLF
ATHYHELTKLEGKIDGVKNYCVSVKEMEDNIVFLRKIIRGGADQSYGIEVAKLAGLPEEVLKRAGEILNSLESKKLKEN
KCVDSEIALDSEYSINEKKAPLKNEEMIKEKAPMLEPTRQLGFSDIEKTNLVKDITDIDILNMTPMDGFNKLYDIIRRA
KSIR (SEQ ID NO: 3)

FIG. 7

MALTPMMQQYMEVKESYKDCILFFRLGDFYEMFFEDAKIASRELELVLTGRDCGLKERAPMCGIPYHAANSYIGRL
INKGYKIAICEQLEDPALAKGIVKRGIIKVVTPGTYTDSTFLEENKNNYIACLYIDTKTNISALCFADVSTGEFNCTDTPF
NLSIILDEISKYSPSELVIQGSISADLLNKMKDIFNGSFTKLDESYFADETKNILEDQFENFTGENYSNEIIKCCGSLLKYIR
ETQKNDLSHINKFSYYNIVDYLTIDGNSRRNLEITESLRENNKKGSLLWVIDKTNTSMGGRQLRRWLEQPLINKVKIE
ERLDSVEEISNNISYHEDLKEALKNIYDIERLVGKISSKSVNAKELNFLKNSIEKIPEVKSILSNFHTKLLKDMYENLDELK
DIYSLLDKSILDNPAISLKEGNLIKKGYNSDIDELKEIKAHGKEWIASLENSEREVTKIKSLKIGYNKVFGYYIEVTKSNLSL
VPEGRYIRKQTLTNAERYITPELKEMEDKILGAEEKLINLEYSVFIEVRDKIENEVDRMQKSAKIISEVDCLSSLARVAIE
NNYCKPEITNSDNIIIEEGRHPVVEKMIDSGEFISNDINIDTGKNQLLLITGPNMAGKSTYMRQIALIVIMAQIGSFVP
AKNASISVCDKIFTRIGASDDLASGKSTFMVEMWEVSNILKNATNKSLILLDEVGRGTSTYDGLSIAWSVIEYICKNSK
LKCKTLFATHYHELTKLEGKIDGVKNYCVSVKEMEDNIVFLRKIIRGGADQSYGIEVAKLAGLPEEVLKRAGEILNSLES
KKLKENKCVDSEIALDSEYSINEKKAPLKNEEMIKEKAPMLEPTRQLGFSDIEKTNLVKDITDIDILNMTPMDGFNKLY
DIIRRAKSIR (SEQ ID NO: 4)

FIG. 8

TAAGTTTTTTGGCCAGATAGCTCAGTCGGTAGAGCAGAGGACTGAAAATCCTCGTGTCCCTGGTTCGATTCCT
GGTCTGGCCACCAAAAGTTTCAGATATAATCTGAAACTTTTTTTATTTTATATAGAAAAAATAATTGAACTATGT
AATAATTAAGTATAAAATATAAAAATATTAAGGAGAAACTTATATGCAAAATAATGTGTTAGCAATTGTAAAT
GGAATGGAAATAAAAGAAAGCGATCTTAAAGAAGCAATTAATAGATTTCCACAAGATAAGAGAAATCAATTA
AATACAGCTGAAGGTAAGAAATATTTACTTAATGAGATGGTATTTTTTGAATTAGCATATAGTTACGCTAAAGA
TGAAAACTTAGAAAAAGATGATGAGTATTTAAAGATGCTGGAATCTGCTAAAAAAGAAATATTAACTCAAATA
GCTATATCTAAAGTTATGAATAAGGTTAATGTAACTGATAAAGAAAGTCAGGATTATTATGAAGCCAATAAAG
ATATGTATAAAAAGCCTGAAAGATTAAAAGCAAAGCATATATTAGTAGATAGTATAGAAAAAGCTAAGAAAA
TTTCAAAAGAGATCTCAGAAGGTATGCCTTTTGAAGAAGCTGCACAAAAATATTCAACTTGTCCATCTAAGGCT
CAAGGTGGCAGTTTAGGTGAATTTGCTAGAGGACAAATGGTTCCAGAATTTGAGAACGCTGCATTTAGTTTAG
ATATAGATGTAGTTAGTGAACCTGTAAAAACTCAATTTGGATACCACCTTATAAAAGTGGAAGAGAAAATAGA
ACCTTCTATAGCATCTTATGATGAAGTAAAGAACGCTATTAAGAATGGATTATTACAGGAAAGACAGAAATAT
GAGTATTCAAAATTTAATAAAGAATTGAGAAGTAAATATAAAGTTGAAATGAAGTAATACATATTGCAATAAA
AATGCCAAGGTAATAATGGACATAGGTTTGTGTAAAAACAAAACCTATGTCCATTATTTTATGTAACTTTTTGA
AATTTAATGGAAATTTATTTCAAATTAAACTAAAATGGTATTTAATATTATAGCATTTTCTTTTATTTGCAGGTA
ATATAATGTCACCGAAATTTTTATAATGAATTGCATCAGGTAATGTCTGCGGTTCCAAAGCTATTCCCATATTG
GAAACTAATTTTTGATTTTGCACTTTCCAAGTGTCATCTTTAATATTAAGAGTATAAACGATTAGAGCATTACGA
TCTGATTCAATGTCTAAACGCCTACATGTATCATGATTAATTAAAGTAGCAATATTTTACCATTTACATTAAAG
GGATGGTCAAAGCCATTGAGGCCCGATTCAGTTTGCAAATATTTAATTGCATCTTCCAAATTTTTAGGCTGCTG
GAAATCAAAAGGTGTTCCAGAAACTTCTTTTAAAGTACCAGTTGGTAATAAGGCTTCATTAATTTCAGCATAAT
GGGATGCATTAATTTGTAGTGTATGACCTGAGAACAACTTTGTAATGTCATTATTTAAGTTGAAGTATGAATGT
ACTGTAGGATTAAAAAGTGCATCTTTATTGCTTAATCCACTAAAAGTGATTAATAAATCATTATTGTTATTAAGT
GTATATTTAACCTCTACATTTAATGTCCCAGGAAATCCATCTTCGTCGGGAGATATAGTCCTATGAAAAAGTAC
ACTAGTGGCTTCTTCAGAGTCTTCTGTGCTACTATTCCATATAAGAGAATTGAACCCATAAGTGCCACCATGAA
GTGTATTTTCACCTTCATTTTTAGGAACGTTATAGGAGATACCTTTAATTTTAAAAGAGCCATTAGCTATGCGAC
CAGCTACTGGTCCGATAGCTGCTCCTAGAAACATCTTTCTATCTTTTATATAACTATCTAAGTTGTCAAAGCCTA
ATAAAACGTTTGAAAAGTTGCCTAACTTATCGGGTACAATAATTTCTGTTAAAGTAGCTCCGTGTGAGATACAG
GAAACTTTCATACCATGTTTGTTAGTCATTGTATATTTATAAATTTTGTTTCCTTTGAAAGAACCAAAAACACTTT
TTTCTATCATTTTATATACTCCTTTAATATTTAATTTTATCCGATGACTACCTGCTCTAATACTCACACTTTTCCAA
GTGGGAGTAAAGATCAGCTACGTCTCTGGATAACGATTTCTAAGCATCAGGCGGAGTTAAAACACCGTCTGAT
GCTTAGAACTCTGTTTATAAGATAAAAAATTTAGGTATGCTTAATTATTTGTGTTATGATAATATTAAATAATAA
GCATACCTTTATATAATTAATTATTTTGTAGTTTCTCTTATAACATCTCTTAAATTTGTATTATGATCTATAATAAT
TGATTCTAAATTAACCATGCGGGCCCAATCATATACTTGTTCAACTGTTAATCCTAGAGTAAGAACAGTATGAT
GACCACCACCAGCATAAATCCAGGCTTTTACACCATCAGCAAAGTTTGGTTCAGGTTTCCATACCATCTTAGCT
ACAGGGAGTTCAGGAGTATCCTCTGCAGGTTCTACAGCATTTACTTCACTGATTATCAAACGATAATGTGTTCC
AAGATCTAGCATTGTCATTGAAGTACCTTTACCAGTAGATCCATTGAATATCAAACGTGCAGGATCTTCACGAT
CACCTATTCCTAAGGGTTTTACCACAACTCTAGGTTTATCAGATGCAAATGTTGGATCAACCTCCAACATATGA
GCGCCTAAGATTTCCTCATTACCTTCACTTAATTCATAAGTATAATCTTCCATAAATCCTGTCTTTTATTGTTTG
TCATGATTTTTATAAGTCTACTTAAAGCAGCAGTTTTCCAATCACCTTCTCCTGCAAAGCCATATCCTTCAGCATT
TAAACGCTGAACTGCAAGTCCAGGTAACTGTTTCATACCATATAAATCTTCGAAATTTGTTGTAAATGCAGTAT
AGCCTCCTGCTTCTAAGAAGTGACGAAGTCCAATTTCAATTTTAATTTGTTCTTTTACTTGATTCTCATAGAATTT
AGGGTCATTTTCTCCTACATCCATAATATAAATCTTTTTAAATTCTTCATAAGTATCATCAATGTCTTTTTGGGAA

FIG. 9A

```
ACTTTATTCATTTCAGCAACTAAATCACCAATACCAAAATAATCTACTGTCCATCCAAACTGAATTTGAGCTTCA
ATCTTATCACCTTCAGTAACAGCAACATTACGCATATTATCACCAAAACGTGCAACTTTGATGTCTTGACTTAAG
ATATAACCTGCGGCTACGTTCATCCAATCAGCAATTTGTTTTTGAACATTTTCTTTTTTCCAATGTCCTACAACAA
TTTTATTATGTTTCTTTAATCTAGCATTAATAAAACCATATTCTCTATCACCATGAGCACTTTGATGTAAGTTCAT
ATAATCCATATCAATTGTTTTCCAAGGAATATGTTCGTAAAATTGTGTTGCTAGATGAAGTAATGGTTTTTGTA
ATAATTTAGTACCAGCAATCCACATTTTAGCTGGTGAGAATGTGTGCATCCATGTAATAACACCAGCTACATTA
TCATTGTAGTTTACTTCCTTCATAAGTTTTGTTATTTGGCTCGCAGAAGTTGCAAGAGATTTAAATACAATAGGA
TAAGGTAATTTGCCACTCTTATTTAAAGCATCTGCAATTTCCATAGAATGTTCTTTTACTTCTGATAGTGCCTCTT
CACCATATAAATGTTGGCTGCCTACAATAAACCAAAATTCCATTTCTTTATTTTTTAGCATAATTGACCCTCTTTC
CTTGTTTTTATTTATTATTTTGACCATAGTATGCATTTTTTCCGTGTTTGCGTTTAAAATGCTTATCTAATAAAACT
TGATCCATTCTAATATTATGGGGATTTAATTGTAAGGAATGATATGTAATTTTTGCAACCTCTTCCAATACGACT
GCATTATGAACTGCATTTTTAGGATCGGTTCCCCAAGTAAATGGACCATGATCATTTACAAGAACTCCAGGTAT
ATCATTTGGATTAATACTATTGTCCTTGAATGTTCTAACAATTACATCTCCTGTCTGCTTCTCATAATCTGTCACT
ATTTCATCTTTAGTCATCTTTGGTGTTACAGGAATATCTCCGTAGAAATAATCGCCATGTGTAGTACCAGCTGC
AGGAATGCAAATACCTGCTTGAGCAAAAGACACGGCCCAAGGAGAATGTGTGTACAATGCCTAAGATGTC
AGGGAAGTTTCTATATAATACTAAGTGAGTTGCTGTATCACTTGACGGATTTAAATCTCCTTCAATTACTTTCCC
ATTAAGATCTACAACGACCATATCACTTGCTTTCATTTTTGTATATTCAACACCACTAGGTTAATAACTACAAG
ACTCTGACTGCGATCAATTCCACTTACGTTGCCCCATGTAAATGTTACCATATGGTATTTTGGCAACATCAAATT
AGCCTCGAGCACTTTTTCTTTTAAATCTTCTAACATGAGCTAACCTTCTTTCACTAATAAGATAAATTATCTTAGT
TGTTTTTAACTTATTCATCTAGATTAAATAATCTACTGCAGCTTGTTCAATAGGAATTCCATTTTTATAACGTTTC
ATAAATTGTTCAAAACCTTTAACGTCTTTTGCTTCAGGTTTTACTTCATCAGCTACATAACCAGCAAAAACTTTTT
TTGATAAAAATTCTGCTAGCGTGGAGTTACTTTCTTTATTATTCAAATAACTAGCTAATAGTGCAATTCCCCATG
CACCGCCTTCACCTGCAGTTTCCATAACTGATACTGGTGTATTTACTGCAGCTGCAACTGCTTCTTGTCCTACAA
TAGGTGTCTTGAATAATCCACCATGACCAAGTAACTTATCAAGCTTTACGCCTTCATCTTTTAGGAGAATGTCC
ATTCCAATTTTCAAGGCTCCTAATGAAGTAAAGAGATGTGCTTTCATAAAGTTTGGTAGATTAAAATTACTTTTT
GGTTTTCGTACAATTAGAGGTCTACCTTCCGGAACACCTGTGATATTTTCGCCTGCAAAATAGTTATATGCAAG
AATTCCTCCACAATCAGGGTCACCTAGAAATGCTTGAGTATAGAGTCCCATATAAAGAAGATCTCTTGGAATG
TTGACATTTATTGCTTCGGCAAATTCATGAAAGATATTAATCCATGCGTCTATATCAGAATAACCATTATTTGCA
TGAACCATTCCAACTAAGTCTCCTGTAGGTGTTGTTACCATATCAATCTCTGGATGAACATTCTTAAGTGGATTC
TCAAGGACGACCATTGCAAAAATTGATGTGCCTGCAGAGATATTTCCTGTACGTGGTGCAACTGAATTTGTAG
CAACCATTCCTGTACCTGCATCTCCTTCAGGTGGACATAGTGGAATACCACTTTGAAGATTTCCACTTACATCAA
GTTTATTGGCTCCTTCTGGAGTTAAGACGCCAGCATTTTCTCCGGCTAGTAAGACTTTTGGTAGAAGCTTCTCT
ACATTCAATGAATACTTTTCAACTTCTGGCAAATGATTGAATGTTTCTAACATATGTTTATCGTAATTATGAGTT
TTCATATCAATTGGAAACATTCCTGATGCATCACAAATACCCAAAACCTTTTTACCTGTTAATTCCCAATGAATA
TAACCAGCTAAAGTAGTTATAAAATCAAGCTTTTCAATATGAGGTTCTTTATGGAGAATAGCCTGATATAAATG
AGCTATACTCCATCTCTCAGGAATATTGAAGTGAAATGATTCTGTTAACTTTTTGGCTGCTTCCTCTGTCATGGT
ATTACGCCATGTCCTAAATGGAACAAGTAGGTTTCCTTGTTTATCAAATGCCATATATCCATGCATCATTGCTGA
AAAACCAATTGAACCAATTTTTGAAAGTGTTACACCATATTTTTCTTTTATCTCAGCAAAAGTTTTTGATAACT
ATATTGTAATCCTTTCCAGATTTCTTCTAGCGAATAGGTCCAAATACCATCTCTTAAGCTTGTCTCCCATTCAAA
GCTGCCACTAGCTAATGGAGAAAAATCGTTTCCAATAAGAACAGCTTTAATACGAGTAGAACCAAATTCTATT
CCTAATGATGTTTTACCATTTTGAATTTCTTTTACTCTATCCTTATTTATAGTCAATAGAATTACCTCCCCCTTACA
ATAATAGTAAACGGTTTTTTATGATAAATATATCATTTATATACGTACATGTCAATAAATATATAAAAAAGAT
```

FIG. 9B

```
ACGTACTTATTTTAAATGTATTTAGATAATTACTTATTAAATAATTATTTTTAGTGATGATATTATCGCGTTTCAT
TACAGCGTTTTAAACAAATATAACTACTTTTTCACAAACAATTGCTATATCATTAAATATTAATTTTACTTGTAAA
TTTATTAGTACAAATTGCTCGATGATTGTAATTATTTTACTTTTTATATTTTTATGCTTTAATATAATATGATATGT
ATTATAATATGAGGTGTAATATAATAAACTATTATTTTGTGCAGGAGATAAACATGAAACATAAATATGAAAA
AGTAAAAGAAGAAATTATTAGCTGGGCAGTTAATGAAAATATAAACCACATGAAAAAATTCCAACAGAATC
GGAACTTATGGAGCTATTTAAAGTTAGTAGACATACTATAAGGAGAGCAATAAGTGATCTAGCGGCAGAGAA
ATACTTGTATAGATTGCAGGGAAGTGGAATATATGTATCTGATTTTAAACAAAATGAAATTTACTTGACAAACA
ACAAGAATGTTGGGGTGCTTACAACATATATTTCCAACTATATATTCCCTGATATAATTAGAGGAATTGAAGAT
ACACTATATGATGAATCATACTCCCTTTTATTATCTTCTACGAAGAATAATATAATGCTTGAAAGCAGCAATTTA
AAAAATTTATTAGCACACAAAATAGATGGACTCATTGTAGAGCCTACAAAGAGTGCATATCAAAGTCCTAACA
TGGGATATTTTAATAATTTAATAGAGCAAGATATTCCTTTTATTATGATAAATGCATCTTATTCTCAAGTTAAAG
TACCAAGCTTATGTGTAGATGATTTAAAGGGGGGCAATATAGCTGCAAAGTATTTAATTACTTTAGGACATAA
GAATATAGCTGGTATTTTCAAGGTAGATGACCTACAAGGTGTGCACAGGATGAATGGTTTTATTACTGGATGT
CAGGAAAGTAATGTATTGTTAAGGCAAGATAAAATTTTAACCTATCTGTCAGAGGAAACAAATACACTACTAC
CTGAAAAGATAAAGAATGTTTTAAAACAGGAAAAACGTCCAACGGGTATATTTTGCTATAATGATGAAATTGC
ATACATGGTGTTAAATATTGCATATGATCTAAAATTAAAGGTTCCAGAAGATTTATCAATTATTGGATTTGATG
ATTCTCCAATGGCAACAATTATGGAACCGAAATTAACATCAATAACTCATCCAAAGGAAAAGATGGGAATAGA
TGCTGCTAAGTTAATTATTAGATTAATTAATAATAATAATCATTTTAGTGAATGTGATTCAATATTATATGAACC
TGAAATTGTTATTAGAAGTTCTACAGCATCAATTTAAATTTATGCACATAATAAAATAAAATTTTCAAAATGATC
CTTATGAATAACATAAGGGTCATTTTTTGTAAAAAAACTAATAAAATGATCAAATTTTTAAGAAATACGGGGAT
TTATCCCTATAAAAATAAAATAAGGTTGACATTTGTACGAACAAATATTATTATTAATTTAAGTAATCGCTTTCA
AAAATAAAATTAAAGGAGGAATGTTAGTGTATAAATACTCCTGGTAATGTAGTGGCTTACGATGATGTTTGAA
AGAGTACGGTGATATGGTTTAAAGGTACTATCATAATTTATTGCAGATTATAAAGATTTATAATTCTCTAAAAA
GTTATATTAAGTTATATTTTATCTATAAGAAAGGAGATTGTTATAAAATGAAAAAAGTTAGTTATTATTATGAT
AATCATTTTAAGATTGGAGATGTTAATGAAAATTTATATAGTTCATTTATTGAGCATTTAGGCAGGGCTGTATA
TAGTGGAATTTATGAACCAGGGCATGAAAAGGCCGATGAAGATGGATTCAGAACAGATGCTATGGAAGTAAT
AAAAGATTTAAAATTGGGATTGGTTCGTTACCCTGGCGGAAATTTTGTTTCCAATTATGATTGGAAAGATGGT
ATTGGACCAAAGGAAAACAGGCCTAAAAGAATGGAATTTGCTTGGTCAAGTGTTGAAACAAATCAATTTGGA
ATTGATGATTTTTGTCGTTGGGCAAAAAAAGCTGGTATTGAACCAATGATAGCAGTTAATTTAGGAACAGGTA
GTGTTAAAAGTGCAGCTGAACTTGTAGAATATTGTAATCATCCTGGCGGGACTTACTGGAGTGATCTTCGTAT
CAAAAATGGAAGTAAGGAGCCTTATAATATAAAATATTGGTGCCTTGGAAATGAAATGGAAGGTACCTGGCA
AGCAGGTCACTTATCAGCAGAAGACTATGCAAAAAAGCTTGTGAAGCTGCTAAACTTATGAAATGGGTAGA
CAAAGATATTAAATTAGTTGCTTGTGGAAGTAGTTATGAAATGCTTCCTACTTATATGGATTGGGATAGAATTG
TACTTAAAGAACTTTATCCTTATGTTGATTACATATCTACTCATAATTATAATATGAATACCAATCAAGGAACGT
CAAATTTTCTTGCATCATATAAACAACTTGATGACCATATAAAAAATACAGAAAGAGTTCTTGATTATGTAAAG
GCAAAAAATAAGGAAGAAAAAGATATAAAAATATGTTTAGATGAATGGAATGTATGGAACTTCCAGGATATA
AAACTTGATAGTCTCGACGACTTACAGGGACTGACGACTTTTGAAGTAACTTCAGCTGAGAAATGGGAAGAA
GCTCCTGCAATCTTAGAGGAAAAATATAGTCTTTTAGATGCACTAACAGTTGGTGGACTTGCAATAACTTTAAT
AAATAATGCTGATAGAGTAAAGATTGCATGTCTTGCACAATTAATTAATGTAATAGCACCTATTACAACGCAG
AGAAATGGAGGAGTTTTAAAACAGTCGACTTATTATCCATTTAGTATGGTTAGTAATTATGGTAGAGGAACTG
```

FIG. 9C

```
TACTTAAACCATCTGTTAATGGTGCAAGCTACAAATGTGATTTTGGTGAATTACCTTTAGTAGAAGCAGCTACT
GTTTATGATAAAGAATCTGATGAAATTAGAGTATTTGCATTAAATTGTAACCAGGATGAAGACACAGAATTAG
ACCTTCAATTTAATGGATTTGGAGATCGTAAAATCTCTAAGCAATTTGTATTATCTGGAGATGACTTAGAACTT
AGAAATACATTTGAAAGTCCTGATAACGTTACTGTAAAGGAAAAAGATCTTTCAAATTGTGATGGTACGAAAG
TTGTTCTTCCAAAGCTTTCTTGGAATGTTTTAATTATAAAGTAATTTCAATAAATTATGAAGGGAGTGGGAAGG
TAAGTGGATATGAAAGTACAAGATAAAGATGTTTTTAAAGAAAATTTAAAATTTAGTGAGAAGTTTGGTTATG
GATGTGGTGATTTAGCCATTAACTTTACTTGGGCTTCTTTGGGAATGTTTGTAGTTTATTTCTATACTGATGTTG
TTGGTATGTCTGCTGCTATTATTGGAACTATTATGTTGTTCTCACGTTGTTTAGATGGTGTCTTAGATGTTATAA
TGGGCACAATTGTTGATAAAACTAATTCAAAGTATGGTAAAGCTCGTCCTTGGATATTATGGGGATCAATTCCT
TTTGTTGTTTTAACAGTATCAATATTTATGGTACCAAACATAAGCACTTTTGGAAAGATAGTGTATATTGTAATA
TCGTATAATTTACTTATGATAGCGTTTACTGCAATTGCTATTCCTTATGGTACATTAAATTCATTGGTTACTCAA
GATCAACATCAGAGAGAAGTATTAAATCTTTTTAGAATGTTTTTGGCACAAATAGGAGTATTAATTGTTACTAA
TCTTACAATGCCATTGGTAAATTTATTTGGAGGAAAACAACCTGGATGGGCTTTAACTTATTCAGTTTTAGGAG
TAGTTTCTCTATTATTATTTGTTTATGTTTTTAAAACGCAAAAAGAAAGAGTAAAACCAATTAAAAAGGAAAAA
ATTCCTTTGAAGATTAGTCTAAAGGCTTTATGTCAAAATAAATATTGGTTTATAGCAACTATATTTTTTATAGTT
TATAGTATTGGATATGCTATAAATCAAGGTAGTACGGTATATTATGCTAAATATCTTCTTGGTAATTCTTCTCTA
GTTGGAGGATTAACTATTGCATATTTAGCTCCAGTATTAGTGGGATTCCTTATGATCTCAAAAGTTTATGATAA
ATACGGAAAAAGAAATGCTATGATCATTGGTTCAATAATAAGCATAGGTGGTTACTTAATTACAATAATAAAT
CCGTATAGTTTAACAGTTGTTATGGTTTCTCAAATTGTTAAAGGTTTTGGCCAAGCTTTCTTGCTAGGAGGAGT
GTGGGCATTATTCCCTGATACTATAGAATATGGTGAATGGAAAACAGGCATAAGAAATGAAGGATTGCTTTAT
AGCGGAGGTAGTTTAGGACAAAAGATGGGTATAGGTTTTGGTACAGCCATAACAGGATGGATTTAGCTTGG
GGAGGATATAATGGTGCACAAGCAGTACAAGCTAGTTCTGCGGTATTTTCAATAAAAGCATTGTTTATTCATG
TTCCAATAATAATATATGTTGCTCAAATTATATTATTGCTCTGTTATGGACTTGACAAAGAGTATCCACGCATTA
TGAAGGATTTACAATTAAGAAAAAGTAAAATGAGTGCAGAAAATAACTAATAAATGTACTTGCAGATTTTATA
CAATATTGTAACTGACATATAAAAATGAATAAGTGAAATAAGGTTTTAGTTTCAATAAAATAACAAATAAATAA
GAAGTAAATAATAGGGAGTGTCTTTTCTGATGGTTTTTTTATCATTAGAGATGATACTCTCTATATTTTTTAATT
TGAATGTCAAAATATGCCATTAAAATTCAAAAGATAATAATTAATAGAAAGTAGGTTAATTTTATGACAAAATA
TAAAAATTAATACTGATAATCACAAAAAACAATTGACATTTGTACGAACAAATATTATTATAAATTTAAGAAAT
CGCTTTCATTTAATGGAATATAAGGGACTAATATGGATACAATGAAGACCATAACAGTAATTACAATTGTTAA
GATTAGTAATAAAAATTTACAATATAAACTTGATTTTTTAATTAAAAGGAGAGGGGATTTAAAAATGATTAAAT
TTAAATCAATTAGAAAAAGCATGAGGTCAATTCTATTATGTGGACTTGTATTAGTTCTAAGTGTAGGTCTCATG
GCATGTGGAAGTACAAGTACTTCAAGTTCTGGTACAAGCAGTAAAAAGAAAACGATAGCATTTATTCCACCAT
CACTTGTAAGCCCATTTTATACTCAGGCTGTTACAGGAGCAAAGCAAGAAGCAGCTAAAGAAGGATTTAACAT
AAAAGTATTGGCTCCTCAAACAGAAGACGATTTCAATGGATTATTAAAAATAGTTGAAGACGTTATAACTCAG
CAAGTTGATGCTATTGCAATATGTACCACAGATGATAAAACTATGGCTGCTGTTGTAAAAAAAGCAAATGATG
CAAAGATACCAGTTATTGTATTTAACTCATTAAGTCCAATAAAGGGTGCAGATGTTTATGCTTATGTTGGATAT
GACCAAAAACAAGCAGGAGCTCAGGCTGCAGACTATTTAGGAACTAAACTTAAAGACAAGCAATTCAATGTT
GGTGTATTAGAGGGTCTTCCTGGTGTATTTACAGACAATAGAAAAGGTGGATTTGTAAATGAAGCTAAAAAAT
ATTCAAATGTAAAGATTGTAGCTACACAACCAGCTGATTGGCAGAGAGAAAAAGGCATGAATGTTGCAACTA
ACCTTTATCAAGCTAATAAGGCTATAAATATGTTTTATGGATTGAGTGATGAAATGGCAATAGGTGCAGCCCA
```

FIG. 9D

```
AGCTTTTAAATCAGCAGGGGTTAAGGATGGAGTTACTATTGGTATAGATGGAAATCCAGCTACTTTAGATTCA
ATCGCACAGGGAGAAACTACTGCTACAATTTATACAGATCCAAAACAAATTGGTAAAGAAAGTATAATAGATT
GTTCTAAAGCTTTAAAAGGTGAAAAAATGGCAAATAAATTAGATCAGACAAAGACTTTTGTAGTAGACAAGA
GTAACGTTAGTACTTATAAAGCAAAATAATTCTATATTTGCTCTTAGAAAATGTTAGCTTTAACATTTTCTAAGA
GTAAAATATTTAGTTACGTAATTTGTGGCAAAAGGGGGGGTAATATTGTCAGAAACTATATTGAAAATGGAG
AACATAACTAAAAGTTTTTCAGGAGTTACAGTTCTTAAAAATTCGGGAATTGAAGTTAAAAAAGGAGAAGTTC
ATATTTTACTTGGTGAAAATGGTGCAGGTAAATCAACTCTTATGAAGATACTTTCTGGAGCATATTCAAAAGAT
AGTGGAGACATTATACTAAACGGAAACAAAGTAGAGATAAATTCTCCAAAAGATGCTGAGAAACTTGGAATA
AGCATAATTTATCAGGAATTTAATTTAGTTCCCTATATGACTGTTGCTGAGAATATATATCTTGGAAGAGAACC
TGAATCCAAGGTACCTGGTAAGGTTAATTTCAAAAAAATGTACAATGATGCACAAAAGATGATTGATTACTTA
AATGTAGATATACCTGTAGATAAACCAATAAAGAATTTAGGAATTGCCCAGCAACAAATGGTTGAGATAGCAA
AAGCACTATCGGTTCATTCTGATATCATAATAATGGATGAGCCAACAGCGGCACTGACAGAAAAAGAAATAG
ATAATTTATTTAAAATAATGAGAAAAATTAAATCTGAAGGAGTTTCTATAATATACATTTCTCATAGACTTGAG
GAATTTGCTCAAATTGGTGATAGAGTTACTGTTATGAGAGATGGAGAAACTGTAGAAACAGTTAATATCAAAG
GTACATCTATAGATGAACTTATAAAATTAATGGTAGGAAGAGAAATTAAAGAAAAATTTCCTAAAATAAAGGT
TGATTTAGGAGAAGAAATATTAAGGGTTAAGGGATTAACCAAAAAAGGAGTTTTTGAAAATATAAATTTCAGT
TTGAGATCAGGCGAAATACTAGGATTTTCTGGTCTTATGGGTGCGGGAAGAACAGAAGTAATGAGGGCTATA
TTTGGTATAGATTCATTTGATTCTGGTGAAATATATTTAAAAGGTAAAAAAGTTGAAATAAATTCCCCTATGAA
AGCAATAAAAAATGGTATAGGATTTGTAACGGAAAATAGAAGAGATGAAGGTCTTGTTTTACAGATGGGTGT
AGGTCAAAATATAACCTTAGCATCCCTTGGCAAATATATTAGTAATCCTATAAAATTAAATCTTAGAAAAGAAG
TCAAGGAAATAAAAGATTATATATCTAAATTGTCAATTAAGTCTTCAGGATATAGACAAATTGCAGGTACACTG
AGCGGTGGAAACCAACAAAAGATTGTTATAGCAAAGTGGCTATTATCTGATTCAAAGGTTTTAATTGTGGATG
AACCTACTCGTGGAATAGATGTAGGTGCTAAAATAGAAATTTATAATATTATGAATGATTTAGTTAAAAGTGG
GGTAGGAATAATTATGGTTTCTTCAGAACTTCCTGAAGTACTTGGCATGAGTGATAGAATATTAGTTATGTGTA
GAGGGAAAATAACTGGAGAATTAAATAAGGATGAGGCTACTCAAGAAAAAATAATGCATTATGCAACAGGA
GGTATAGAATGATGAATCAGTTAGAAGATACTGAAAAAAGAAAAAGACTAGTATAAATGACATACTGGATA
AGCTAGGGGTTGTCATTGCATTAGTTGTTTTAATTGTAGTTATGGCTGTGTTGTCTCCAGATTTTCTTACTGTAA
AAAATGTATTTAACATATTGCAGCAGATTGCACAAATTGGAATAATATCTGTTGGTATGACTTTTGTAATATTA
CTTGGAGGAATCGACTTATCTGTTGGTTCAATTATTGCATTTACAGGACTTATTATGGCATTATGCATGAAAGC
AGGAATGTCTGTTGTGTTAGCTATTTTAGTAGGTATTATACTAGGTGCAGCTATTGGTTTCTTAAATGGAATTT
TAATATCAAAGGTTAAACTCCAACCTTTTATAGCTACACTAGGAACTATGACTATGGCTAGAGGACTTGCATAT
ACTATAACAAATGGACAACCAGTATATTCTTTCTCAGCTGGGTTTAAAAGCTTTGCTGGATTTATTGGAGTTGT
TCCAATTCCTGCAATTATTATGGCAGTAATATTTGCATTAGGTTATTATGTGCTTAAATACACAAAGTTTGGAA
GATACATGTATGCTATTGGAGGAAATAGAGTAGCAAGTAAGCTTTCAGGAATAAATGTGGATAAATATGAGA
TGTTGGTTTATACGATTTCAGGAATATGCTGTGCTATAGCTGCTATAATTTTAACAGCAAGGCTTGATTCAGCA
GTACCAGTTGCAGGTGATGGAAACGAACTTGATGCTATAGCGGCAGTAGCTATAGGTGGAACAAGTATGACC
GGTGGAGAAGGCGGTATAGTTGGAACACTTATTGGTGCCTTAATTATGGGAGTAATTGCGAATGGAATGAAC
CTACTAGATGTGCAACAGGGACCACAGAGGTTTGCTAAAGGTGCAATTATAATTTTAGCTGTAGGAATTGATG
TAATAAGAAAGAAAAGAACTTCTAAATAATACTTTGGATAAATTCACAAGGTGCTTATTAATTTTTATTAAAAA
AGTTTCAGATTATATCCGAAACTTTTTTTGTATTTAAATACTATAGTTTTATCTCCAATCCTAAAAGAAATTTGTT
```

FIG. 9E

TATTAGGGTTATTTAATGATATGTAATAGGTATCATATTTATTAAAAATGGGTAATATAGTTCTCTGTTAGAATA
AATTAAGTATAAACATATCCATGTGTATCTATGTAAGAAAAATGGTGAATATAAGTAGTATAAAGGAGAAAAT
GCAAATTAAGTTATAAAAATACCGGAGTAAGTGAACTGAGTTAAGTATAAGCTGTGATATAATAAATTTCGTT
GTCATGGAGATTACAGAAACAGATTAAATCAATAGTTTTTTATTTAAAGAAAAATAATAAAACGTATTGACAG
ATGTAATTTAAAATGATATACTATAAAGG (SEQ ID NO: 5)

FIG. 9F

ATCTGTATATTTTTTCCCATTTTAATTATTTGTACTATAATATTACACTGAGTGTATTGCATATTTAAAAAATATT
TGGTACAATTAGTTAGTTAAATAAATTCTAAATTGTAAATTATCAGAATCCTTATTAAGGAAATACATAGATTT
AAGGAGAAATCATAAAAAGGTGTAATATAAACTGGCTAAAATTGAGCAAAAATTGAGCAATTAAGACTTTTTG
ATTGTATCTTTTTATATATTTAAGGTATATAATCTTATTTATATTGGGGGAACTTGATGAATAAACATATTCTAG
AC (SEQ ID NO: 6)

FIG. 10

ATCTGTATATTTTTTCCCATTTTAATTATTTGTACTATAATATTACACTGAGTGTATTGTATATTTAAAAAATATTT
GGTACAATTAGTTAGTTAAATAAATTCTAAATTGTAAATTATCAGAATCCTTATTAAGGAAATACATAGATTTA
AGGAGAAATCATAAAAAGGTGTAATATAAACTGGCTAAAATTGAGCAAAAATTGAGCAATTAAGACTTTTTGA
TTGTATCTTTTTATATATTTAAGGTATATAATCTTATTTATATTGGGGGAACTTGATGAATAAACATATTCTAGA
C (SEQ ID NO: 7)

FIG. 11

TGTTAATTTTTTGTGTCAATAATTTTTGTTATATTATTTTAATTAAATTTTTCACATGTATAATTAAAAGTAAGAT
AGATATTCTAATGTACTTACTTAGGTAGAAAAACATGTATACAAAATTAAAAAACTATTATAACACATAGTATC
AATATTGAAGGTAATACTGTTCAATATCGATACAGATAAAAAAAATATATAATACAGAAGAAAAAATTATAAAT
TGTGGTATAATATAAAGTATAGTAATTTAAGTTTAAACCTCGTGAAAACGCTAACAAATAATAGGAGGTGTA
TTAT (SEQ ID NO: 8)

FIG. 12

GTTAATTTTTTGTGTCAATAATTTTTGTTATATTATTTTAATTAAATTTTTCACATGTATAATTAAAAGTAAGATA
GATATTCTAATGTACTTACTTAGGTAGAAAAACATGTATACAAAATTAAAAAACTATTATAACACATAGTATCA
ATATTGAAGGTAATACTGTTCAATATCGATACAGATAAAAAAAATATATAATACAGAAGAAAAAATTATAAAT
TGTGGTATAATATAAAGTATAGTAATTTAAGTTTAAACCTCGTGAAAACGCTAACAAATAATAGGAGGTGTA
TTAT (SEQ ID NO: 9)

FIG. 13

AGTTGGATAAATAGGGTTTATCCTTAAAAGTTTTATTCACAGTGTGTATGAAAAAAAATTCACACTGTGAATTT
TTTTTATAAATTTTTCTACACTGTAAAATTCAATTATGTTATTCAACTCATTGTAAATACCATTCACATGTTATTTT
TGACCATTCGCATCCGTTTTTTTGCACTTTGGAATATTTGGGTATGAAAATCAATAAATTCAGACTATTATAAAC
ATGTAATAAAATTCATATAATTAATTATTAATGAACTATTTATAATTATTAAAAATTAAAAAGGAGGTTTTTAT
(SEQ ID NO: 10)

FIG. 14

AGTTGGATAAATAGGGTTTATCCTTAAAAGTTTTATTCACAGTGTGTATAGAAAAAAAATTCACACTGTGAATT
TTTTTTATAAATTTTTCACACTGTAAAATTCAATTATGTTATTCAACTCATTGTAAATACCATTCACATGTTATTTT
TGACCATTCGCATCCGTTTTTTTGCACTTTGGAATATTTGGGTATGAAAATCAATAAATTCAGACTATTATAAAC
ATGTAATAAAATTCATATAATTAATTATTAATGAACTATTTATAATTATTAAAAATTAAAAAGGAGGTTTTTAT
(SEQ ID NO: 11)

FIG. 15

ATGAATTTATTTCAAACTGTATTCACTGGTTCAAAGCAAGCTTTAGCAGCTGCTGAAGGCATAGTTAAGCAAGC
TGTTGACGAGAAGGGTAGAGACTATAAAGTAGCATTTCCTGATACTGAATATTCATTACCAGTAATTTTTGCAG
CTACAGGAAAAAAGATAACTAATGTAGGAGAATTAGAAGGTGCATTAGATATAGTAAGAAGTTTGATAGTTG
AGGAGGAAATGCTTGATAAGCTTTTAAATTCAGGACTTGCAACAGCTGTTGCAGCAGAAATTATAGAAGCTGC
AAAGTATGTTCTTTCCGATGCTCCTTATGCAGAACCATGTGTAGGATTTATATCTGACCCAATAATTCGTTCTCT
TGGTGTACCACTTGTTACCGGAGATATACCAGGTGTAGCAGTTATATTAGGAGAATGTCCAGATTCAGAAACC
GCAGCTAAAATTATAAAGGATTATCAATCAAAAGGTCTTTTAACATGCTTAGTTGGAAAAGTAATTGATCAGG
CAATAGAAGGAAAAGTTAAGATGGGTCTTGACCTCAGAGTTATTCCACTTGGATATGATGTTACATCTGTAATT
CACGTTGTAACTATAGCTATAAGAGCTGCACTTATATTCGGAGGAATTAAGGGTGGTCAGTTAAATGACATAT
TGAAATATACAGCAGAAAGGGTACCTGCTTTTGTAAATGCATTTGGACCATTAAGTGAACTTGTAGTTTCAGCT
GGTGCAGGAGCTATAGCACTTGGATTCCCTGTATTAACTGATCAGGTTGTACCAGAAGTTCCTACATTGTTGTT
AACTCAAAAAGATTATGATAAAATGGTTAAAACTTCATTAGAAGCTAGAAATATAAAGATAAAGATAACTGAG
ATCCCAATTCCAGTTTCCTTTGCAGCAGCATTTGAAGGTGAAAGAATAAGAAAGAATGATATGCTTGCAGAGT
TTGGTGGAAATAAGACTAAAGCTTGGGAATTAGTTATGTGTGCAGATCAGGGAGAAGTTGAAGATCACAAGA
TAGAAGTTATAGGACCAGATATAGATACTATAGATAAGGCTCCTGGAAGAATGCCTCTTGGAATGCTTATTAA
AGTAAGTGGAACAAATATGCAGAAGGATTTTGAGCCAGTGCTTGAAAGAAGACTTCACTACTTCTT

AAACTATATAGAAGGAGTAATGCATGTTGGTCAGAGAAATCTTACTTGGGTAAGAATAGGTAAGGAAGCTTT
TGAAAAGGGATTTAGATTGAAACATTTTGGTGAAGTAATATATGCTAAAATGTTAGATGAATTTGGTTCAGTT
GTAGATAAATGTGAAGTAACTATAATAACTGATCCAGGTAAGGCTGAAGAATTGGAAGGCAAATATGCTGTA
CCAAGATATAAAGAAAGAGATGCAAGACTTGAATCATTAGTTGATGAAAAGTTGATACTTTCTATTCATGTA
ATTTGTGTCAATCCTTTGCACCTGCACATGTATGTATAGTAACTCCTGAAAGACTTGGACTTTGCGGTGCAGTT
TCATGGCTTGATGCTAAAGCTACACTTGAATTAAATCCTACAGGACCATGTCAGGCCGTTCCAAAAGAAGGCG
TGGTTGATGAAAATTTAGGTATTTGGGAAAAAGTAAATGAAACTGTTTCAAAAATTTCTCAAGGTGCTGTAAC
TAGTGTTACATTATACAGTATATTACAAGATCCAATGACTTCCTGTGGATGTTTTGAGTGTATTACAGGTATAA
TGCCAGAAGCAAATGGTGTTGTAATGGTAAACAGAGAATTTGGTGCAACAACTCCTCTTGGAATGACATTTGG
TGAACTTGCATCTATGACAGGTGGTGGAGTTCAGACTCCAGGATTTATGGGACATGGAAGACAATTCATAGCT
TCAAAGAAGTTTATGAAAGGTGAAGGCGGACTTGGCAGAATAGTTTGGATGCCAAAAGAATTAAAAGACTTT
GTTGCAGAAAAATTAAATAAGACAGCAAAGGAATTATATAATATAGATAATTTTGCAGATATGATCTGTGATG
AAACTATAGCTACAGAATCTGAAGAAGTAGTAAAATTCTTGGAAGAAAAAGGTCATCCTGCATTAAAGATGG
ATCCAATAATGTAG (SEQ ID NO: 12)

FIG. 16

ATGAATTTATTTCAAACTGTATTCACTGGTTCAAAGCAAGCTTTAGCAGCTGCTGAAGGCATAGTTAAGCAAGC
TGTTGACGAGAAGGGTAGAGACTATAAAGTAGCATTTCCTGATACTGCATATTCATTACCAGTAATTTTTGCAG
CTACAGGAAAAAAGATAACTAATGTAGGAGAATTAGAAGGTGCATTAGATATAGTAAGAAGTTTGATAGTTG
AGGAGGAAATGCTTGATAAGCTTTTAAATTCAGGACTTGCAACAGCTGTTGCAGCAGAAATTATAGAAGCTGC
AAAGTATGTTCTTTCCGATGCTCCTTATGCAGAACCATGTGTAGGATTTATATCTGACCCAATAATTCGTTCTCT
TGGTGTACCACTTGTTACCGGAGATATACCAGGTGTAGCAGTTATATTAGGAGAATGTCCAGATTCAGAAACC
GCAGCTAAAATTATAAAGGATTATCAATCAAAAGGTCTTTTAACATGCTTAGTTGGAAAAGTAATTGATCAGG
CAATAGAAGGAAAAGTTAAGATGGGTCTTGACCTCAGAGTTATTCCACTTGGATATGATGTTACATCTGTAATT
CACGTTGTAACTATAGCTATAAGAGCTGCACTTATATTCGGAGGAATTAAGGGTGGTCAGTTAAATGACATAT
TGAAATATACAGCAGAAAGGGTACCTGCTTTTGTAAATGCATTTGGACCATTAAGTGAACTTGTAGTTTCAGCT
GGTGCAGGAGCTATAGCACTTGGATTCCCTGTATTAACTGATCAGGTTGTACCAGAAGTTCCTACATTGTTGTT
AACTCAAAAAGATTATGATAAAATGGTTAAAACTTCATTAGAAGCTAGAAATATAAAGATAAAGATAACTGAG
ATCCCAATTCCAGTTTCCTTTGCAGCAGCATTTGAAGGTGAAAGAATAAGAAAGAATGATATGCTTGCAGAGT
TTGGTGGAAATAAGACTAAAGCTTGGGAATTAGTTATGTGTGCAGATCAGGGAGAAGTTGAAGATCACAAGA
TAGAAGTTATAGGACCAGATATAGATACTATAGATAAGGCTCCTGGAAGAATGCCTCTTGGAATGCTTATTAA
AGTAAGTGGAACAAATATGCAGAAGGATTTTGAGCCAGTGCTTGAAAGAAGACTTCACTACTTCTTAAACTAT
ATAGAAGGAGTAATGCATGTTGGTCAGAGAAATCTTACTTGGGTAAGAATAGGTAAGGAAGCTTTTGAAAAG
GGATTTAGATTGAAACATTTTGGTGAAGTAATATATGCTAAAATGTTAGATGAATTTGGTTCAGTTGTAGATAA
ATGTGAAGTAACTATAATAACTGATCCAGGTAAGGCTGAAGAATTGGAAGGCAAATATGCTGTACCAAGATA
TAAAGAAAGAGATGCAAGACTTGAATCATTAGTTGATGAAAAGTTGATACTTTCTATTCATGTAATTTGTGTC
AATCCTTTGCACCTGCACATGTATGTATAGTAACTCCTGAAAGACTTGGACTTTGCGGTGCAGTTTCATGGCTT
GATGCTAAAGCTACACTTGAATTAAATCCTACAGGACCATGTCAGGCCGTTCCAAAAGAAGGCGTGGTTGATG
AAAAATTTAGGTATTTGGGAAAAAGTAAATGAAACTGTTTCAAAAATTTCTCAAGGTGCTGTAACTAGTGTTAC
ATTATACAGTATATTACAAGATCCAATGACTTCCTGTGGATGTTTTGAGTGTATTACAGGTATAATGCCAGAAG
CAAATGGTGTTGTAATGGTAAACAGAGAATTTGGTGCAACAACTCCTCTTGGAATGACATTTGGTGAACTTGC
ATCTATGACAGGTGGTGGAGTTCAGACTCCAGGATTTATGGGACATGGAAGACAATTCATAGCTTCAAAGAA
GTTTATGAAAGGTGAAGGCGGACTTGGCAGAATAGTTTGGATGCCAAAAGAATTAAAAGACTTTGTTGCAGA
AAAATTAAATAAGACAGCAAAGGAATTATATAATATAGATAATTTTGCAGATATGATCTGTGATGAAACTATA
GCTACAGAATCTGAAGAAGTAGTAAAATTCTTGGAAGAAAAAGGTCATCCTGCATTAAAGATGGATCCAATAA
TGTAG (SEQ ID NO: 13)

FIG. 17

MNLFQTVFTGSKQALAAAEGIVKQAVDEKGRDYKVAFPDTEYSLPVIFAATGKKITNVGELEGALDIVRSLIVEEEML
DKLLNSGLATAVAAEIIEAAKYVLSDAPYAEPCVGFISDPIIRSLGVPLVTGDIPGVAVILGECPDSETAAKIIKDYQSKG
LLTCLVGKVIDQAIEGKVKMGLDLRVIPLGYDVTSVIHVVTIAIRAALIFGGIKGGQLNDILKYTAERVPAFVNAFGPLS
ELVVSAGAGAIALGFPVLTDQVVPEVPTLLLTQKDYDKMVKTSLEARNIKIKITEIPIPVSFAAAFEGERIRKNDMLAE
FGGNKTKAWELVMCADQGEVEDHKIEVIGPDIDTIDKAPGRMPLGMLIKVSGTNMQKDFEPVLERRLHYFLNYIE
GVMHVGQRNLTWVRIGKEAFEKGFRLKHFGEVIYAKMLDEFGSVVDKCEVTIITDPGKAEELEGKYAVPRYKERDA
RLESLVDEKVDTFYSCNLCQSFAPAHVCIVTPERLGLCGAVSWLDAKATLELNPTGPCQAVPKEGVVDENLGIWEK
VNETVSKISQGAVTSVTLYSILQDPMTSCGCFECITGIMPEANGVVMVNREFGATTPLGMTFGELASMTGGGVQT
PGFMGHGRQFIASKKFMKGEGGLGRIVWMPKELKDFVAEKLNKTAKELYNIDNFADMICDETIATESEEVVKFLEE
KGHPALKMDPIM (SEQ ID NO: 14)

FIG. 18

MNLFQTVFTGSKQALAAAEGIVKQAVDEKGRDYKVAFPDTAYSLPVIFAATGKKITNVGELEGALDIVRSLIVEEEM
LDKLLNSGLATAVAAEIIEAAKYVLSDAPYAEPCVGFISDPIIRSLGVPLVTGDIPGVAVILGECPDSETAAKIIKDYQSK
GLLTCLVGKVIDQAIEGKVKMGLDLRVIPLGYDVTSVIHVVTIAIRAALIFGGIKGGQLNDILKYTAERVPAFVNAFGP
LSELVVSAGAGAIALGFPVLTDQVVPEVPTLLLTQKDYDKMVKTSLEARNIKIKITEIPIPVSFAAAFEGERIRKNDMLA
EFGGNKTKAWELVMCADQGEVEDHKIEVIGPDIDTIDKAPGRMPLGMLIKVSGTNMQKDFEPVLERRLHYFLNYI
EGVMHVGQRNLTWVRIGKEAFEKGFRLKHFGEVIYAKMLDEFGSVVDKCEVTIITDPGKAEELEGKYAVPRYKERD
ARLESLVDEKVDTFYSCNLCQSFAPAHVCIVTPERLGLCGAVSWLDAKATLELNPTGPCQAVPKEGVVDENLGIWE
KVNETVSKISQGAVTSVTLYSILQDPMTSCGCFECITGIMPEANGVVMVNREFGATTPLGMTFGELASMTGGGVQ
TPGFMGHGRQFIASKKFMKGEGGLGRIVWMPKELKDFVAEKLNKTAKELYNIDNFADMICDETIATESEEVVKFLE
EKGHPALKMDPIM (SEQ ID NO: 15)

FIG. 19

ATGAGCTTATTGAAGGAAGCTTTTGAAAAGGGAGAGTTTGCAATTACAGCTGAAATGGCACCTCCAAAGGGA
ACGGATCTTTCTCATTTAATTGAATGTGCCAAAAAGATAAAAGGAAGAGTTCAGGGAGTTAATGTAACGGATT
TTCAGTCTGCTACATTAAAAGCTACATCTTTAGCTACTTGTAAAGTATTAAAAGATGCAGGATTAGAGCCTGTA
TTTCAAATAACAGGAAGAGATAGAAACAGAATAGCAATTCAAGGAGAATTGTTATCTGCAGGTGTTTTTGGAA
TTGAAAACGTTTTAGCTCTTACTGGGGATTATACTGCTACAGGAGATCACCCTGGTGCAAAGCCAGTTTATGAT
CTAGATAGTGTTGGAATATTACAGGTGGCAAGCATTTTAAATGGTGGAAAAGACATGGGTGGAACTGATTTA
AAAGGGAAACCAGATTTCTTTTTAGGGGCCTGTGTTACACCTAGATATGATCCGTTAGAGCTTCAAGTTATAAA
GATGAAGAAGAAATTAAAGCTGGAGCTAAATTCTTTCAAACTCAAGCTGTTTATGATATGGAAACTTTAAAG
AAATTCAAAGAAGAGACTAAAGCTCAAGGTGTAGATGCTAAAGTTATGGTAGGCATAATACCTTTAAAGTCAG
CTGGTATGGCTAAATACATGAATAAAAACGTACCTGGTATATTCGTACCTGATGAACTTATAGATAGAATGAA
GAATGCTGAGGATAAAGTTCAAGAAGGCATAAAGATAGCAGGAGAATTTATAAAGGCCGTAAAAGAATCAG
GACTTTGCGATGGAGTTCATATAATGGCAATTGGTGCGGAAGAAAATGTGCCATTAATATTGGATGAAGCAG
GATTATAA (SEQ ID NO: 16)

FIG. 20

ATGAGCTTATTGAAGGAAGCTTTTGAAAAGGGAGAGTTTGCAATTACAGCTGAAATGGCACCTCCAAAGGGA
ACGGATCTTTCTCATTTAATTGAATGTGCCAAAAAGATAAAAGGAAGAGTTCAGGGAGTTAATGTAACGGATT
TTCAGTCTGCTACATTAAAAGCTACATCTTTAGCTACTTGTAAAGTATTAAAAGATGCAGGATTAGAGCCTGTA
TTTCAAATAACAGGAAGAGATAGAAACAGAATAGCAATTCAAGGAGAATTGTTATCTGCAGGTGTTTTTGGAA
TTGAAAATGTTTTAGCTCTTACTGGGGATTATACTGCTACAGGAGATCACCCTGGTGCAAAGCCAGTTTATGAT
CTAGATAGTGTTGGAATATTACAGGTGGCAAGCATTTTAAATGGTGGAAAAGACATGGGTGGAACTGATTTA
AAAGGGAAACCAGATTTCTTTTTAGGGGCCTGTGTTACACCTAGATATGATCCGTTAGAGCTTCAAGTTATAAA
GATGAAGAAGAAAATTAAAGCTGGAGCTAAATTCTTTCAAACTCAAGCTGTTTATGATATGGAAACTTTAAAG
AAATTCAAAGAAGAGACTAAAGCTCAAGGTGTAGATGCTAAAGTTATGGTAGGCATAATACCTTTAAAGTCAG
CTGGTATGGCTAAATACATGAATAAAAACGTACCTGGTATATTCGTACCTGATGAACTTATAGATAGAATGAA
GAATGCTGAGGATAAAGTTCAAGAAGGCATAAAGATAGCAGGAGAATTTATAAAGGCCGTAAAAGAATCAG
GACTTTGCGATGGAGTTCATATAATGGCAATTGGTGCGGAAGAAAATGTGCCATTAATATTGGATGAAGCAG
GATTATAA (SEQ ID NO: 17)

FIG. 21

SEQUENCE LISTING

<160> NUMBER OF SEQ ID NOS: 17

<210> SEQ ID NO 1
<211> LENGTH: 2655
<212> TYPE: DNA
<213> ORGANISM: Clostridium autoethanogenum

<400> SEQUENCE: 1

```
gtggcattaa ctccaatgat gcagcagtat atggaagtaa aagaaagtta taaagactgt      60
atactgtttt ttagattagg tgatttttat gaaatgtttt ttgaagatgc aaaaatagca     120
tctagggaac tagaattagt acttacaggt agagattgcg gcttaaaaga aagggctcct     180
atgtgtggaa taccctatca tgccgcaaat tcatatatag gaaggcttat aaacaaggga     240
tataagatag ctatatgtga gcaactagaa gatccagctc tagcaaaagg tatagttaaa     300
aggggcataa tcaaggttgt aactcctggg acttatacgg actctacttt tttagaagaa     360
aataaaaata attatatagc gtgtttgtac atagatacca agacaaatat ttctgcattg     420
tgttttgcag atgtgtccac tggagaattc aattgtacgg acactccttt taatttatct     480
ataattttag atgaaatatc aaaatactct ccaagtgaac tagtgattca aggtagtata     540
agtgctgatt tattgaataa aatgaaggat attttttaatg gctcattcac taaattagat     600
gaaagctatt ttgcagacga aactaaaaat atattagagg atcagtttga aaattttaca     660
ggagaaaatt atagtaatga aattataaaa tgctgcggct cactactaaa atatataagg     720
gaaactcaaa agaatgatct atctcatata aataaatttt cctattacaa tatagtagat     780
tatctcacta tagatgggaa ttccagaaga aatttagaaa ttacagaaag cttaagagaa     840
aataataaaa aaggatctct cctctgggtt atagataaaa caaatacatc tatgggaggg     900
agacagctta gaagatggct ggaacagccc cttataaata aggttaagat agaagaaaga     960
ctggattctg tagaggaaat ttcaaataat atatcctatc atgaagatct aaaagaggct    1020
ttaaaaaaca tatatgatat tgagcgatta gttggaaaaa tatcttctaa aagtgtaaac    1080
gcaaaagaac taaattttt aaaaaattct atagaaaaaa tacctgaagt aaaatccata    1140
ctatccaatt ttcatacaaa attattgaag gatatgtacg aaaacttgga tgaactaaag    1200
gacatatatt cacttttaga taaatctata ttagataatc ctgcaatatc tttaaaagaa    1260
ggtaacctta taaaaaaggg atataacagt gacatagatg aacttaaaga aataaaggct    1320
cacggtaagg agtggatagc ttctcttgag aattcagaaa gggaagttac taaaataaaa    1380
tctcttaaaa taggttataa taaagtattt ggttattata ttgaggttac taaaagtaat    1440
ttaagtcttg taccagaagg tagatatata agaaaacaaa ctcttacaaa tgcagaaaga    1500
tacataactc ctgaattgaa agaaatggaa gataaaaatat taggtctaga atatagtgtc    1560
tttatagaag taagagataa aatagaaaat gaagtagaca gaatgcaaaa atccgctaaa    1620
```

```
ataatttcag aagtagattg cttaagctcc cttgcaagag ttgctataga aaataattat    1680
tgtaaacctg aaataacaaa ttcagataac ataattatag aagaaggtag acatcctgta    1740
gtagaaaaga tgattgactc tggagaattt atatcaaacg atataaacat agatactggt    1800
aaaaatcaac ttcttttaat aacagggcct aatatggcag gcaaatctac ctacatgagg    1860
cagatagctt tgatcgttat aatggcccaa attggtagct ttgtaccggc aaaaaatgct    1920
tctatatctg tttgtgataa agatatttaca aggataggtg catcagatga cctggcatca    1980
ggaaagagta cctttatggt ggaaatgtgg gaggtttcca acatacttaa aaatgcaact    2040
aacaaaagtt tgattttact ggatgaagta ggacgtggaa caagtactta cgacggcctt    2100
agcatagcct ggtcagtaat agaatatata tgtaaaaaca gcaaactaaa atgtaaaacc    2160
ttatttgcaa cccattatca tgaactaact aaattagaag gtaagataga tggagtcaaa    2220
aattactgtg tatccgttaa agaaatggag gataatatag tttttttgag aaaaattata    2280
agaggaggag ccgaccaatc ctacggcata gaagttgcaa agcttgcagg gcttccagaa    2340
gaagttttaa aaagagcagg agaaatacta atagccttg aaagtaaaaa gctaaaagaa    2400
aataaatgtg ttgattctga aattgcatta gattcagagt attcaataaa tgagaaaaaa    2460
gcacctctta aaaatgagga gatgattaaa gaaaaagctc ctatgcttga accaaccaga    2520
caattaggat tttcagatat agaaaagaca aatttagtaa agatattac ggatatagat    2580
atactaaaca tgactcctat ggacggattt aataaacttt atgatataat aagaagagca    2640
aagtccataa gataa                                                    2655

<210> SEQ ID NO 2
<211> LENGTH: 2676
<212> TYPE: DNA
<213> ORGANISM: Clostridium autoethanogenum

<400> SEQUENCE: 2
gtggcattaa ctccaatgat gcagcagtat atggaagtaa agaaagtta taaagactgt      60
atactgtttt ttagattagg tgatttttat gaaatgtttt ttgaagatgc aaaaatagca     120
tctagggaac tagaattagt acttacaggt agagattgcg gcttaaaaga aagggctcct     180
atgtgtggaa taccctatca tgccgcaaat tcatatatag gaaggcttat aaacaaggga     240
tataagatag ctatatgtga gcaactagaa gatccagctc tagcaaaagg tatagttaaa     300
aggggcataa tcaaggttgt aactcctggg acttatacgg actctacttt tttagaagaa     360
aataaaaata attatatagc gtgtttgtac atagatacca agacaaatat ttctgcattg     420
tgttttgcag atgtgtccac tggagaattc aattgtacgg acactccttt taatttatct     480
ataattttag atgaaatatc aaaatactct ccaagtgaac tagtgattca aggtagtata     540
agtgctgatt tattgaataa aatgaaggat attttttaatg gctcattcac taaattagat     600
gaaagctatt ttgcagacga aactaaaaat atattagagg atcagtttga aaattttaca     660
ggagaaaatt atagtaatga aattataaaa tgctgcggct cactactaaa atatataagg     720
gaaactcaaa agaatgatct atctcatata aataaatttt cctattacaa tatagtagat     780
tatctcacta tagatgggaa ttccagaaga aatttagaaa ttacagaaag cttaagagaa     840
aataataaaa aaggatctct cctctgggtt atagataaaa caaatacatc tatgggaggg     900
agacagctta gaagatggct ggaacagccc cttataaata aggttaagat agaagaaaga     960
ctggattctg tagaggaaat ttcaaataat atatcctatc atgaagatct aaaagaggct    1020
ttaaaaaaca tatatgatat tgagcgatta gttggaaaaa tatcttctaa aagtgtaaac    1080
```

-continued

```
gcaaaagaac taaattttt aaaaaattct atagaaaaaa tacctgaagt aaaatccata    1140
ctatccaatt ttcatacaaa attattgaag gatatgtacg aaaacttgga tgaactaaag   1200
gacatatatt cacttttaga taaatctata ttagataatc ctgcaatatc tttaaaagaa   1260 ggtaaccta taaaaaaggg atataacagt gacatagatg aacttaaaga aataaaggct    1320
cacggtaagg agtggatagc ttctcttgag aattcagaaa gggaagttac taaaataaaa   1380
tctcttaaaa taggttataa taaagtattt ggttattata ttgaggttac taaaagtaat   1440
ttaagtcttg taccagaagg tagatatata agaaaacaaa ctcttacaaa tgcagaaaga   1500
tacataactc ctgaattgaa agaaatggaa gataaaatat taggtgcaga ggaaaaactt   1560
ataaatctag aatatagtgt ctttatagaa gtaagagata aaatagaaaa tgaagtagac   1620
agaatgcaaa aatccgctaa aataatttca gaagtagatt gcttaagctc ccttgcaaga   1680
gttgctatag aaaataatta ttgtaaacct gaaataacaa attcagataa cataattata   1740
gaagaaggta gacatcctgt agtagaaaag atgattgact ctggagaatt tatatcaaac   1800
gatataaaca tagatactgg taaaaatcaa cttctttaa taacagggcc taatatggca    1860
ggcaaatcta cctacatgag gcagatagct ttgatcgtta taatggccca aattggtagc   1920
tttgtaccgg caaaaaatgc ttctatatct gtttgtgata agatatttac aaggataggt   1980
gcatcagatg acctggcatc aggaaagagt acctttatgg tggaaatgtg ggaggtttcc   2040
aacatactta aaaatgcaac taacaaaagt ttgatttac tggatgaagt aggacgtgga    2100
acaagtactt acgacggcct tagcatagcc tggtcagtaa tagaatatat atgtaaaaac   2160
agcaaactaa aatgtaaaac cttatttgca acccattatc atgaactaac taaattagaa   2220
ggtaagatag atggagtcaa aaattactgt gtatccgtta agaaatgga ggataatata    2280 gttttttga gaaaaattat aagaggagga gccgaccaat cctacggcat agaagttgca    2340
aagcttgcag gcttccaga agaagtttta aaaagagcag gagaaatact aaatagcctt    2400
gaaagtaaaa agctaaaaga aaataaatgt gttgattctg aaattgcatt agattcagag   2460
tattcaataa atgagaaaaa agcacctctt aaaaatgagg agatgattaa agaaaaagct   2520
cctatgcttg aaccaaccag acaattagga ttttcagata tagaaaagac aaatttagta   2580
aaagatatta cggatataga tatactaaac atgactccta tggacggatt taatataactt  2640 tatgatataa taagaagagc aaagtccata agataa                            2676
```

<210> SEQ ID NO 3
<211> LENGTH: 884
<212> TYPE: PRT
<213> ORGANISM: Clostridium autoethanogenum

<400> SEQUENCE: 3

```
Met Ala Leu Thr Pro Met Met Gln Gln Tyr Met Glu Val Lys Glu Ser
1               5                   10                  15

Tyr Lys Asp Cys Ile Leu Phe Phe Arg Leu Gly Asp Phe Tyr Glu Met
            20                  25                  30

Phe Phe Glu Asp Ala Lys Ile Ala Ser Arg Glu Leu Glu Leu Val Leu
        35                  40                  45

Thr Gly Arg Asp Cys Gly Leu Lys Glu Arg Ala Pro Met Cys Gly Ile
    50                  55                  60

Pro Tyr His Ala Ala Asn Ser Tyr Ile Gly Arg Leu Ile Asn Lys Gly
65                  70                  75                  80

Tyr Lys Ile Ala Ile Cys Glu Gln Leu Glu Asp Pro Ala Leu Ala Lys
```

-continued

```
                85                  90                  95
Gly Ile Val Lys Arg Gly Ile Lys Val Val Thr Pro Gly Thr Tyr
               100                 105                 110
Thr Asp Ser Thr Phe Leu Glu Glu Asn Lys Asn Tyr Ile Ala Cys
               115                 120                 125
Leu Tyr Ile Asp Thr Lys Thr Asn Ile Ser Ala Leu Cys Phe Ala Asp
    130                 135                 140
Val Ser Thr Gly Glu Phe Asn Cys Thr Asp Thr Pro Phe Asn Leu Ser
145                 150                 155                 160
Ile Ile Leu Asp Glu Ile Ser Lys Tyr Ser Pro Ser Glu Leu Val Ile
                165                 170                 175
Gln Gly Ser Ile Ser Ala Asp Leu Leu Asn Lys Met Lys Asp Ile Phe
                180                 185                 190
Asn Gly Ser Phe Thr Lys Leu Asp Glu Ser Tyr Phe Ala Asp Glu Thr
                195                 200                 205
Lys Asn Ile Leu Glu Asp Gln Phe Glu Asn Phe Thr Gly Glu Asn Tyr
    210                 215                 220
Ser Asn Glu Ile Ile Lys Cys Cys Gly Ser Leu Leu Lys Tyr Ile Arg
225                 230                 235                 240
Glu Thr Gln Lys Asn Asp Leu Ser His Ile Asn Lys Phe Ser Tyr Tyr
                245                 250                 255
Asn Ile Val Asp Tyr Leu Thr Ile Asp Gly Asn Ser Arg Arg Asn Leu
                260                 265                 270
Glu Ile Thr Glu Ser Leu Arg Glu Asn Asn Lys Lys Gly Ser Leu Leu
                275                 280                 285
Trp Val Ile Asp Lys Thr Asn Thr Ser Met Gly Gly Arg Gln Leu Arg
    290                 295                 300
Arg Trp Leu Glu Gln Pro Leu Ile Asn Lys Val Lys Ile Glu Glu Arg
305                 310                 315                 320
Leu Asp Ser Val Glu Glu Ile Ser Asn Asn Ile Ser Tyr His Glu Asp
                325                 330                 335
Leu Lys Glu Ala Leu Lys Asn Ile Tyr Asp Ile Glu Arg Leu Val Gly
                340                 345                 350
Lys Ile Ser Ser Lys Ser Val Asn Ala Lys Glu Leu Asn Phe Leu Lys
    355                 360                 365
Asn Ser Ile Glu Lys Ile Pro Glu Val Lys Ser Ile Leu Ser Asn Phe
    370                 375                 380
His Thr Lys Leu Leu Lys Asp Met Tyr Glu Asn Leu Asp Glu Leu Lys
385                 390                 395                 400
Asp Ile Tyr Ser Leu Leu Asp Lys Ser Ile Leu Asp Asn Pro Ala Ile
                405                 410                 415
Ser Leu Lys Glu Gly Asn Leu Ile Lys Gly Tyr Asn Ser Asp Ile
                420                 425                 430
Asp Glu Leu Lys Glu Ile Lys Ala His Gly Lys Glu Trp Ile Ala Ser
                435                 440                 445
Leu Glu Asn Ser Glu Arg Glu Val Thr Lys Ile Lys Ser Leu Lys Ile
    450                 455                 460
Gly Tyr Asn Lys Val Phe Gly Tyr Tyr Ile Glu Val Thr Lys Ser Asn
465                 470                 475                 480
Leu Ser Leu Val Pro Glu Gly Arg Tyr Ile Arg Lys Gln Thr Leu Thr
                485                 490                 495
Asn Ala Glu Arg Tyr Ile Thr Pro Glu Leu Lys Glu Met Glu Asp Lys
                500                 505                 510
```

```
Ile Leu Gly Leu Glu Tyr Ser Val Phe Ile Glu Val Arg Asp Lys Ile
            515                 520                 525

Glu Asn Glu Val Asp Arg Met Gln Lys Ser Ala Lys Ile Ile Ser Glu
530                 535                 540

Val Asp Cys Leu Ser Ser Leu Ala Arg Val Ala Ile Glu Asn Asn Tyr
545                 550                 555                 560

Cys Lys Pro Glu Ile Thr Asn Ser Asp Asn Ile Ile Glu Glu Gly
            565                 570                 575

Arg His Pro Val Val Glu Lys Met Ile Asp Ser Gly Glu Phe Ile Ser
            580                 585                 590

Asn Asp Ile Asn Ile Asp Thr Gly Lys Asn Gln Leu Leu Leu Ile Thr
            595                 600                 605

Gly Pro Asn Met Ala Gly Lys Ser Thr Tyr Met Arg Gln Ile Ala Leu
610                 615                 620

Ile Val Ile Met Ala Gln Ile Gly Ser Phe Val Pro Ala Lys Asn Ala
625                 630                 635                 640

Ser Ile Ser Val Cys Asp Lys Ile Phe Thr Arg Ile Gly Ala Ser Asp
            645                 650                 655

Asp Leu Ala Ser Gly Lys Ser Thr Phe Met Val Glu Met Trp Glu Val
            660                 665                 670

Ser Asn Ile Leu Lys Asn Ala Thr Asn Lys Ser Leu Ile Leu Leu Asp
            675                 680                 685

Glu Val Gly Arg Gly Thr Ser Thr Tyr Asp Gly Leu Ser Ile Ala Trp
690                 695                 700

Ser Val Ile Glu Tyr Ile Cys Lys Asn Ser Lys Leu Lys Cys Lys Thr
705                 710                 715                 720

Leu Phe Ala Thr His Tyr His Glu Leu Thr Lys Leu Glu Gly Lys Ile
            725                 730                 735

Asp Gly Val Lys Asn Tyr Cys Val Ser Val Lys Glu Met Glu Asp Asn
            740                 745                 750

Ile Val Phe Leu Arg Lys Ile Ile Arg Gly Gly Ala Asp Gln Ser Tyr
            755                 760                 765

Gly Ile Glu Val Ala Lys Leu Ala Gly Leu Pro Glu Glu Val Leu Lys
            770                 775                 780

Arg Ala Gly Glu Ile Leu Asn Ser Leu Glu Ser Lys Lys Leu Lys Glu
785                 790                 795                 800

Asn Lys Cys Val Asp Ser Glu Ile Ala Leu Asp Ser Glu Tyr Ser Ile
            805                 810                 815

Asn Glu Lys Lys Ala Pro Leu Lys Asn Glu Met Ile Lys Glu Lys
            820                 825                 830

Ala Pro Met Leu Glu Pro Thr Arg Gln Leu Gly Phe Ser Asp Ile Glu
            835                 840                 845

Lys Thr Asn Leu Val Lys Asp Ile Thr Asp Ile Asp Ile Leu Asn Met
850                 855                 860

Thr Pro Met Asp Gly Phe Asn Lys Leu Tyr Asp Ile Ile Arg Arg Ala
865                 870                 875                 880

Lys Ser Ile Arg

<210> SEQ ID NO 4
<211> LENGTH: 891
<212> TYPE: PRT
<213> ORGANISM: Clostridium autoethanogenum

<400> SEQUENCE: 4
```

```
Met Ala Leu Thr Pro Met Met Gln Gln Tyr Met Glu Val Lys Glu Ser
1               5                   10                  15

Tyr Lys Asp Cys Ile Leu Phe Phe Arg Leu Gly Asp Phe Tyr Glu Met
                20                  25                  30

Phe Phe Glu Asp Ala Lys Ile Ala Ser Arg Glu Leu Glu Leu Val Leu
            35                  40                  45

Thr Gly Arg Asp Cys Gly Leu Lys Glu Arg Ala Pro Met Cys Gly Ile
        50                  55                  60

Pro Tyr His Ala Ala Asn Ser Tyr Ile Gly Arg Leu Ile Asn Lys Gly
65                  70                  75                  80

Tyr Lys Ile Ala Ile Cys Glu Gln Leu Glu Asp Pro Ala Leu Ala Lys
                85                  90                  95

Gly Ile Val Lys Arg Gly Ile Ile Lys Val Val Thr Pro Gly Thr Tyr
                100                 105                 110

Thr Asp Ser Thr Phe Leu Glu Glu Asn Lys Asn Asn Tyr Ile Ala Cys
        115                 120                 125

Leu Tyr Ile Asp Thr Lys Thr Asn Ile Ser Ala Leu Cys Phe Ala Asp
        130                 135                 140

Val Ser Thr Gly Glu Phe Asn Cys Thr Asp Thr Pro Phe Asn Leu Ser
145                 150                 155                 160

Ile Ile Leu Asp Glu Ile Ser Lys Tyr Ser Pro Ser Glu Leu Val Ile
                165                 170                 175

Gln Gly Ser Ile Ser Ala Asp Leu Leu Asn Lys Met Lys Asp Ile Phe
            180                 185                 190

Asn Gly Ser Phe Thr Lys Leu Asp Glu Ser Tyr Phe Ala Asp Glu Thr
        195                 200                 205

Lys Asn Ile Leu Glu Asp Gln Phe Glu Asn Phe Thr Gly Glu Asn Tyr
    210                 215                 220

Ser Asn Glu Ile Ile Lys Cys Cys Gly Ser Leu Leu Lys Tyr Ile Arg
225                 230                 235                 240

Glu Thr Gln Lys Asn Asp Leu Ser His Ile Asn Lys Phe Ser Tyr Tyr
                245                 250                 255

Asn Ile Val Asp Tyr Leu Thr Ile Asp Gly Asn Ser Arg Arg Asn Leu
                260                 265                 270

Glu Ile Thr Glu Ser Leu Arg Glu Asn Asn Lys Lys Gly Ser Leu Leu
            275                 280                 285

Trp Val Ile Asp Lys Thr Asn Thr Ser Met Gly Gly Arg Gln Leu Arg
        290                 295                 300

Arg Trp Leu Glu Gln Pro Leu Ile Asn Lys Val Lys Ile Glu Glu Arg
305                 310                 315                 320

Leu Asp Ser Val Glu Glu Ile Ser Asn Asn Ile Ser Tyr His Glu Asp
                325                 330                 335

Leu Lys Glu Ala Leu Lys Asn Ile Tyr Asp Ile Glu Arg Leu Val Gly
                340                 345                 350

Lys Ile Ser Ser Lys Ser Val Asn Ala Lys Glu Leu Asn Phe Leu Lys
            355                 360                 365

Asn Ser Ile Glu Lys Ile Pro Glu Val Lys Ser Ile Leu Ser Asn Phe
        370                 375                 380

His Thr Lys Leu Leu Lys Asp Met Tyr Glu Asn Leu Asp Glu Leu Lys
385                 390                 395                 400

Asp Ile Tyr Ser Leu Leu Asp Lys Ser Ile Leu Asp Asn Pro Ala Ile
                405                 410                 415
```

```
Ser Leu Lys Glu Gly Asn Leu Ile Lys Lys Gly Tyr Asn Ser Asp Ile
            420                 425                 430

Asp Glu Leu Lys Glu Ile Lys Ala His Gly Lys Glu Trp Ile Ala Ser
            435                 440                 445

Leu Glu Asn Ser Glu Arg Glu Val Thr Lys Ile Lys Ser Leu Lys Ile
            450                 455                 460

Gly Tyr Asn Lys Val Phe Gly Tyr Tyr Ile Glu Val Thr Lys Ser Asn
465                 470                 475                 480

Leu Ser Leu Val Pro Glu Gly Arg Tyr Ile Arg Lys Gln Thr Leu Thr
            485                 490                 495

Asn Ala Glu Arg Tyr Ile Thr Pro Glu Leu Lys Glu Met Glu Asp Lys
            500                 505                 510

Ile Leu Gly Ala Glu Glu Lys Leu Ile Asn Leu Glu Tyr Ser Val Phe
            515                 520                 525

Ile Glu Val Arg Asp Lys Ile Glu Asn Glu Val Asp Arg Met Gln Lys
            530                 535                 540

Ser Ala Lys Ile Ile Ser Glu Val Asp Cys Leu Ser Ser Leu Ala Arg
545                 550                 555                 560

Val Ala Ile Glu Asn Asn Tyr Cys Lys Pro Glu Ile Thr Asn Ser Asp
            565                 570                 575

Asn Ile Ile Ile Glu Glu Gly Arg His Pro Val Val Glu Lys Met Ile
            580                 585                 590

Asp Ser Gly Glu Phe Ile Ser Asn Asp Ile Asn Ile Asp Thr Gly Lys
            595                 600                 605

Asn Gln Leu Leu Leu Ile Thr Gly Pro Asn Met Ala Gly Lys Ser Thr
            610                 615                 620

Tyr Met Arg Gln Ile Ala Leu Ile Val Ile Met Ala Gln Ile Gly Ser
625                 630                 635                 640

Phe Val Pro Ala Lys Asn Ala Ser Ile Ser Val Cys Asp Lys Ile Phe
            645                 650                 655

Thr Arg Ile Gly Ala Ser Asp Asp Leu Ala Ser Gly Lys Ser Thr Phe
            660                 665                 670

Met Val Glu Met Trp Glu Val Ser Asn Ile Leu Lys Asn Ala Thr Asn
            675                 680                 685

Lys Ser Leu Ile Leu Leu Asp Glu Val Gly Arg Gly Thr Ser Thr Tyr
690                 695                 700

Asp Gly Leu Ser Ile Ala Trp Ser Val Ile Glu Tyr Ile Cys Lys Asn
705                 710                 715                 720

Ser Lys Leu Lys Cys Lys Thr Leu Phe Ala Thr His Tyr His Glu Leu
            725                 730                 735

Thr Lys Leu Glu Gly Lys Ile Asp Gly Val Lys Asn Tyr Cys Val Ser
            740                 745                 750

Val Lys Glu Met Glu Asp Asn Ile Val Phe Leu Arg Lys Ile Ile Arg
            755                 760                 765

Gly Gly Ala Asp Gln Ser Tyr Gly Ile Glu Val Ala Lys Leu Ala Gly
            770                 775                 780

Leu Pro Glu Glu Val Leu Lys Arg Ala Gly Glu Ile Leu Asn Ser Leu
785                 790                 795                 800

Glu Ser Lys Lys Leu Lys Glu Asn Lys Cys Val Asp Ser Glu Ile Ala
            805                 810                 815

Leu Asp Ser Glu Tyr Ser Ile Asn Glu Lys Lys Ala Pro Leu Lys Asn
            820                 825                 830

Glu Glu Met Ile Lys Glu Lys Ala Pro Met Leu Glu Pro Thr Arg Gln
```

```
                 835                 840                 845
Leu Gly Phe Ser Asp Ile Glu Lys Thr Asn Leu Val Lys Asp Ile Thr
    850                 855                 860
Asp Ile Asp Ile Leu Asn Met Thr Pro Met Asp Gly Phe Asn Lys Leu
865                 870                 875                 880
Tyr Asp Ile Ile Arg Arg Ala Lys Ser Ile Arg
                885                 890

<210> SEQ ID NO 5
<211> LENGTH: 15408
<212> TYPE: DNA
<213> ORGANISM: Clostridium autoethanogenum

<400> SEQUENCE: 5
```

| | | | | | |
|---|---|---|---|---|---|
| taagtttttt | ggccagatag | ctcagtcggt | agagcagagg | actgaaaatc | ctcgtgtccc | 60 |
| tggttcgatt | cctggtctgg | ccaccaaaag | tttcagatat | aatctgaaac | tttttttatt | 120 |
| ttatatagaa | aaataattg | aactatgtaa | taattaagta | taaaatataa | aaatattaag | 180 |
| gagaaactta | tatgcaaaat | aatgtgttag | caattgtaaa | tggaatggaa | ataaaagaaa | 240 |
| gcgatcttaa | agaagcaatt | aatagatttc | cacaagataa | gagaaatcaa | ttaaatacag | 300 |
| ctgaaggtaa | gaaatattta | cttaatgaga | tggtattttt | tgaattagca | tatagttacg | 360 |
| ctaaagatga | aaacttagaa | aaagatgatg | agtatttaaa | gatgctggaa | tctgctaaaa | 420 |
| aagaaatatt | aactcaaata | gctatatcta | aagttatgaa | taaggttaat | gtaactgata | 480 |
| aagaaagtca | ggattattat | gaagccaata | agtatatgta | taaaaagcct | gaaagattaa | 540 |
| aagcaaagca | tatattagta | gatagtatag | aaaaagctaa | gaaaatttca | aaagagatct | 600 |
| cagaaggtat | gcctttgaa | gaagctgcac | aaaaatattc | aacttgtcca | tctaaggctc | 660 |
| aaggtggcag | tttaggtgaa | tttgctagag | acaaatggt | tccagaattt | gagaacgctg | 720 |
| catttagttt | agatatagat | gtagttagtg | aacctgtaaa | aactcaattt | ggataccacc | 780 |
| ttataaaagt | ggaagagaaa | atagaaccct | ctatagcatc | ttatgatgaa | gtaaagaacg | 840 |
| ctattaagaa | tggattatta | caggaaagac | agaaatatga | gtattcaaaa | tttaataaag | 900 |
| aattgagaag | taaatataaa | gttgaaatga | agtaatacat | attgcaataa | aaatgccaag | 960 |
| gtaataatgg | acataggttt | gtgtaaaaac | aaaacctatg | tccattattt | tatgtaactt | 1020 |
| tttgaaattt | aatggaaatt | tatttcaaat | taaactaaaa | tggtatttaa | tattatagca | 1080 |
| ttttctttta | tttgcaggta | atataatgtc | accgaaattt | ttataatgaa | ttgcatcagg | 1140 |
| taatgtctgc | ggttccaaag | ctattcccat | attggaaact | aattttttgat | tttgcactttt | 1200 |
| ccaagtgtca | tctttaatat | taagagtata | aacgattaga | gcattacgat | ctgattcaat | 1260 |
| gtctaaacgc | ctacatgtat | catgattaat | taaagtagca | atattttac | catttacatt | 1320 |
| aaagggatgg | tcaaagccat | tgaggcccga | ttcagtttgc | aaatatttaa | ttgcatcttc | 1380 |
| caaatttta | ggctgctgga | aatcaaaagg | tgttccagaa | acttctttta | aagtaccagt | 1440 |
| tggtaataag | gcttcattaa | tttcagcata | atgggatgca | ttaatttgta | gtgtatgacc | 1500 |
| tgagaacaac | tttgtaatgt | cattatttaa | gttgaagtat | gaatgtactg | taggattaaa | 1560 |
| aagtgcatct | ttattgctta | atccactaaa | agtgattaat | aaatcattat | tgttattaag | 1620 |
| tgtatattta | acctctacat | ttaatgtccc | aggaaatcca | tcttcgtcgg | gagatatagt | 1680 |
| cctatgaaaa | agtacactag | tggcttcttc | agagtcttct | gtgctactat | tccatataag | 1740 |
| agaattgaac | ccataagtgc | caccatgaag | tgtatttca | ccttcatttt | taggaacgtt | 1800 |

```
ataggagata cctttaattt taaaagagcc attagctatg cgaccagcta ctggtccgat    1860
agctgctcct agaaacatct ttctatcttt tatataacta tctaagttgt caaagcctaa    1920
taaaacgttt gaaaagttgc ctaacttatc gggtacaata atttctgtta aagtagctcc    1980
gtgtgagata caggaaactt tcataccatg tttgttagtc attgtatatt tataaatttt    2040
gtttcctttg aaagaaccaa aaacactttt ttctatcatt ttatatactc ctttaatatt    2100
taattttatc cgatgactac ctgctctaat actcacactt ttccaagtgg gagtaaagat    2160
cagctacgtc tctggataac gatttctaag catcaggcgg agttaaaaca ccgtctgatg    2220
cttagaactc tgtttataag ataaaaaatt taggtatgct taattatttg tgttatgata    2280
atattaaata ataagcatac ctttatataa ttaattattt tgtagtttct cttataacat    2340
ctcttaaatt tgtattatga tctataataa ttgattctaa attaaccatg cgggcccaat    2400
catatacttg ttcaactgtt aatcctagag taagaacagt atgatgacca ccaccagcat    2460
aaatccaggc ttttacacca tcagcaaagt ttggttcagg tttccatacc atcttagcta    2520
cagggagttc aggagtatcc tctgcaggtt ctacagcatt tacttcactg attatcaaac    2580
gataatgtgt tccaagatct agcattgtca ttgaagtacc tttaccagta gatccattga    2640
atatcaaacg tgcaggatct tcacgatcac ctattcctaa gggttttacc acaactctag    2700
gtttatcaga tgcaaatgtt ggatcaacct ccaacatatg agcgcctaag atttcctcat    2760
taccttcact taattcataa gtaatcttct ccataaatcc tgtcttttta ttgtttgtca    2820
tgatttttat aagtctactt aaagcagcag ttttccaatc accttctcct gcaaagccat    2880
atccttcagc atttaaacgc tgaactgcaa gtccaggtaa ctgtttcata ccatataaat    2940
cttcgaaatt tgttgtaaat gcagtatagc ctcctgcttc taagaagtga cgaagtccaa    3000
tttcaatttt aatttgttct tttacttgat tctcatagaa tttagggtca ttttctccta    3060
catccataat ataaatcttt ttaaattctt cataagtatc atcaatgtct ttttgggaaa    3120
ctttattcat ttcagcaact aaatcaccaa taccaaaata atctactgtc catccaaact    3180
gaatttgagc ttcaatctta tcaccttcag taacagcaac attacgcata ttatcaccaa    3240
aacgtgcaac tttgatgtct tgacttaaga tataacctgc ggctacgttc atccaatcag    3300
caatttgttt ttgaacattt tctttttttcc aatgtcctac aacaatttta ttatgtttct    3360
ttaatctagc attaataaaa ccatattctc tatccaccatg agcactttga tgtaagttca    3420
tataatccat atcaattgtt ttccaaggaa tatgttcgta aaattgtgtt gctagatgaa    3480
gtaatggttt ttgtaataat ttagtaccag caatccacat tttagctggt gagaatgtgt    3540
gcatccatgt aataacacca gctacattat cattgtagtt tacttccttc ataagttttg    3600
ttatttggct cgcagaagtt gcaagagatt taaatacaat aggataaggt aatttgccac    3660
tcttatttaa agcatctgca atttccatag aatgttcttt tacttctgat agtgcctctt    3720
caccatataa atgttggctg cctacaataa accaaaattc catttcttta ttttttagca    3780
taattgaccc tctttccttg tttttattta ttattttgac catagtatgc atttttttccg    3840 tgtttgcgtt taaatgcett atctaataaa acttgatcca ttctaatatt atggggattt    3900
aattgtaagg aatgatatgt aatttttgca acctcttcca atacgactgc attatgaact    3960
gcatttttag gatcggttcc ccaagtaaat ggaccatgat catttacaag aactccaggt    4020
atatcatttg gattaatact attgtccttg aatgttctaa caattacatc tcctgtctgc    4080
ttctcataat ctgtcactat ttcatcttta gtcatctttg gtgttacagg aatatctccg    4140
tagaaataat cgccatgtgt agtaccagct gcaggaatgc aaatacctgc ttgagcaaaa    4200
```

```
gacacggccc aaggagaatg tgtgtgtaca atgcctaaga tgtcagggaa gtttctatat    4260
aatactaagt gagttgctgt atcacttgac ggatttaaat ctccttcaat tactttccca    4320
ttaagatcta caacgaccat atcacttgct ttcattttg tatattcaac accactaggt     4380
ttaataacta caagactctg actgcgatca attccactta cgttgcccca tgtaaatgtt    4440
accatatggt attttggcaa catcaaatta gcctcgagca cttttctttt taaatcttct    4500
aacatgagct aaccttcttt cactaataag ataaattatc ttagttgttt ttaacttatt    4560
catctagatt aaataatcta ctgcagcttg ttcaatagga attccatttt tataacgttt    4620
cataaattgt tcaaaacctt taacgtcttt tgcttcaggt tttacttcat cagctacata    4680
accagcaaaa acttttttg ataaaaattc tgctagcgtg gagttacttt ctttattatt     4740
caaataacta gctaatagtg caattcccca tgcaccgcct tcacctgcag tttccataac    4800
tgatactggt gtatttactg cagctgcaac tgcttcttgt cctacaatag gtgtcttgaa    4860
taatccacca tgaccaagta acttatcaag ctttacgcct tcatctttta ggagaatgtc    4920
cattccaatt ttcaaggctc ctaatgaagt aaagagatgt gctttcataa agtttggtag    4980
attaaaatta cttttgg tt tcgtacaat tagaggtcta ccttccggaa cacctgtgat      5040
attttcgcct gcaaaatagt tatatgcaag aattcctcca caatcagggt cacctagaaa    5100
tgcttgagta tagagtccca tataaagaag atctcttgga atgttgacat ttattgcttc    5160
ggcaaattca tgaaagatat taatccatgc gtctatatca gaataaccat tatttgcatg    5220
aaccattcca actaagtctc ctgtaggtgt tgttaccata tcaatctctg gatgaacatt    5280
cttaagtgga ttctcaagga cgaccattgc aaaaattgat gtgcctgcag agatatttcc    5340
tgtacgtggt gcaactgaat ttgtagcaac cattcctgta cctgcatctc cttcaggtgg    5400
acatagtgga ataccacttt gaagatttcc acttacatca agtttattgg ctccttctgg    5460
agttaagacg ccagcatttt ctccggctag taagactttt ggtagaagct tctctacatt    5520
caatgaatac ttttcaactt ctggcaaatg attgaatgtt tctaacatat gtttatcgta    5580
attatgagtt ttcatatcaa ttggaaacat tcctgatgca tcacaaatac ccaaaacctt    5640
tttacctgtt aattcccaat gaatataacc agctaaagta gttataaaat caagcttttc    5700
aatatgaggt tctttatgga gaatagcctg atataaatga gctatactcc atctctcagg    5760
aatattgaag tgaaatgatt ctgttaactt tttggctgct tcctctgtca tggtattacg    5820
ccatgtccta aatggaacaa gtaggtttcc ttgtttatca aatgccatat atccatgcat    5880
cattgctgaa aaaccaattg aaccaatttt tgaaagtgtt acaccatatt tttctttat    5940 ctcagcaaaa agttttgat aactatattg taatcctttc cagatttctt ctagcgaata    6000
ggtccaaata ccatctctta agcttgtctc ccattcaaag ctgccactag ctaatggaga    6060
aaaatcgttt ccaataagaa cagctttaat acgagtagaa ccaaattcta ttcctaatga    6120
tgttttacca ttttgaattt ctttttactct atccttatt atagtcaata gaattacctc     6180
ccccttacaa taatagtaaa cggttttta tgataaatat atcatttata tacgtacatg      6240
tcaataaata tataaaaaaa gatacgtact tatttaaat gtatttagat aattacttat       6300
taaataatta tttttagtga tgatattatc gcgtttcatt acagcgtttt aaacaaatat     6360 aactacttt tcacaaacaa ttgctatatc attaaatatt aattttactt gtaaatttat     6420
tagtacaaat tgctcgatga ttgtaattat tttacttttt atattttat gctttaatat     6480 aatatgatat gtattataat atgaggtgta atataataaa ctattatttt gtgcaggaga    6540
```

```
taaacatgaa acataaatat gaaaaagtaa aagaagaaat tattagctgg gcagttaatg    6600
aaaaatataa accacatgaa aaattccaa cagaatcgga acttatggag ctatttaaag     6660
ttagtagaca tactataagg agagcaataa gtgatctagc ggcagagaaa tacttgtata    6720
gattgcaggg aagtggaata tatgtatctg atttttaaaca aaatgaaatt tacttgacaa    6780
acaacaagaa tgttggggtg cttacaacat atatttccaa ctatatattc cctgatataa    6840
ttagaggaat tgaagataca ctatatgatg aatcatactc cctttttatta tcttctacga   6900 agaataatat aatgcttgaa agcagcaatt taaaaaattt attagcacac aaaatagatg    6960
gactcattgt agagcctaca aagagtgcat atcaaagtcc taacatggga tattttaata    7020
atttaataga gcaagatatt ccttttatta tgataaatgc atcttattct caagttaaag    7080
taccaagctt atgtgtagat gatttaaagg ggggcaatat agctgcaaag tatttaatta   7140
ctttaggaca taagaatata gctggtattt tcaaggtaga tgacctacaa ggtgtgcaca    7200
ggatgaatgg ttttattact ggatgtcagg aaagtaatgt attgttaagg caagataaaa    7260
ttttaaccta tctgtcagag gaaacaaata cactactacc tgaaaagata aagaatgttt    7320
taaaacagga aaaacgtcca acgggtatat tttgctataa tgatgaaatt gcatacatgg    7380 tgttaaaatat tgcatatgat ctaaaattaa aggttccaga agatttatca attattggat    7440
ttgatgattc tccaatggca acaattatgg aaccgaaatt aacatcaata actcatccaa    7500
aggaaaagat gggaatagat gctgctaagt taattattag attaattaat aataataatc    7560
attttagtga atgtgattca atattatatg aacctgaaat tgttattaga agttctacag    7620
catcaattta aatttatgca cataataaaa taaaattttc aaaatgatcc ttatgaataa    7680
cataagggtc atttttgta aaaaaactaa taaaatgatc aaattttttaa gaaatacggg    7740 gatttatccc tataaaaata aaataaggtt gacatttgta cgaacaaata ttattattaa    7800
tttaagtaat cgctttcaaa aataaaatta aaggaggaat gttagtgtat aaatactcct    7860
ggtaatgtag tggcttacga tgatgtttga aagagtacgg tgatatggtt taaaggtact    7920
atcataattt attgcagatt ataaagattt ataattctct aaaaagttat attaagttat    7980 atttatcta taagaaagga gattgttata aaatgaaaaa agttagttat tattatgata    8040 atcatttta gattggagat gttaatgaaa atttatatag ttcatttatt gagcatttag    8100
gcagggctgt atatagtgga atttatgaac cagggcatga aaaggccgat gaagatggat    8160
tcagaacaga tgctatggaa gtaataaaag atttaaaatt gggattggtt cgttaccctg    8220
gcggaaattt tgtttccaat tatgattgga aagatggtat tggaccaaag gaaaacaggc    8280
ctaaaagaat ggaatttgct tggtcaagtg ttgaaacaaa tcaatttgga attgatgatt    8340
tttgtcgttg gcaaaaaaa gctggtattg aaccaatgat agcagttaat ttaggaacag    8400
gtagtgttaa aagtgcagct gaacttgtag aatattgtaa tcatcctggc gggacttact    8460
ggagtgatct tcgtatcaaa aatggaagta aggagcctta taatataaaaa tattggtgcc    8520 ttggaaatga aatggaaggt acctggcaag caggtcactt atcagcagaa gactatgcaa    8580
aaaaagcttg tgaagctgct aaacttatga atgggtaga caaagatatt aaattagttg    8640
cttgtggaag tagttatgaa atgcttccta cttatatgga ttgggataga attgtactta    8700
agaactttta tccttatgtt gattacatat ctactcataa ttataatatg aataccaatc    8760
aaggaacgtc aaatttttctt gcatcatata acaacttga tgaccatata aaaaatacag    8820
aaagagttct tgattatgta aaggcaaaaa ataaggaaga aaaagatata aaaatatgtt    8880
tagatgaatg gaatgtatgg aacttccagg atataaaact tgatagtctc gacgacttac    8940
```

```
agggactgac gacttttgaa gtaacttcag ctgagaaatg ggaagaagct cctgcaatct    9000
tagaggaaaa atatagtctt ttagatgcac taacagttgg tggacttgca ataactttaa    9060
taaataatgc tgatagagta aagattgcat gtcttgcaca attaattaat gtaatagcac    9120
ctattacaac gcagagaaat ggaggagttt taaaacagtc gacttattat ccatttagta    9180
tggttagtaa ttatggtaga ggaactgtac ttaaaccatc tgttaatggt gcaagctaca    9240
aatgtgattt tggtgaatta cctttagtag aagcagctac tgtttatgat aaagaatctg    9300
atgaaattag agtatttgca ttaaattgta accaggatga agacacagaa ttagaccttc    9360
aatttaatgg atttggagat cgtaaaatct ctaagcaatt tgtattatct ggagatgact    9420
tagaacttag aaatacattt gaaagtcctg ataacgttac tgtaaaggaa aagatctttt    9480
caaattgtga tggtacgaaa gttgttcttc caaagctttc ttggaatgtt ttaattataa    9540
agtaatttca ataaattatg aagggagtgg gaaggtaagt ggatatgaaa gtacaagata    9600
aagatgtttt taaagaaaat ttaaaattta gtgagaagtt tggttatgga tgtggtgatt    9660
tagccattaa ctttacttgg gcttctttgg gaatgtttgt agtttatttc tatactgatg    9720
ttgttggtat gtctgctgct attattggaa ctattatgtt gttctcacgt tgtttagatg    9780
gtgtcttaga tgttataatg ggcacaattg ttgataaaac taattcaaag tatggtaaag    9840
ctcgtccttg gatattatgg ggatcaattc cttttgttgt tttaacagta tcaatattta    9900
tggtaccaaa cataagcact tttggaaaga tagtgtatat tgtaatatcg tataatttac    9960
ttatgatagc gttactgca attgctattc cttatggtac attaaattca ttggttactc   10020
aagatcaaca tcagagagaa gtattaaatc ttttttagaat gttttttggca caaataggag   10080 tattaattgt tactaatctt acaatgccat tggtaaattt atttggagga aaacaacctg   10140
gatgggcttt aacttattca gttttaggag tagtttctct attattattt gtttatgttt   10200
ttaaaacgca aaaagaaaga gtaaaaccaa ttaaaaagga aaaaattcct ttgaagatta   10260
gtctaaaggc tttatgtcaa aataaatatt ggtttatagc aactatattt tttatagttt   10320
atagtattgg atatgctata atcaaggta gtacggtata ttatgctaaa tatcttcttg   10380
gtaattcttc tctagttgga ggattaacta ttgcatattt agctccagta ttagtgggat   10440
tccttatgat ctcaaaagtt tatgataaat acggaaaaag aaatgctatg atcattggtt   10500
caataataag cataggtggt tacttaatta caataataaa tccgtatagt ttaacagttg   10560
ttatggtttc tcaaattgtt aaaggttttg gccaagcttt cttgctagga ggagtgtggg   10620
cattattccc tgatactata gaatatggtg aatggaaaac aggcataaga atgaaggat   10680 tgctttatag cggaggtagt ttaggacaaa agatgggtat aggttttggt acagccataa   10740
caggatggat tttagcttgg ggaggatata atggtgcaca agcagtacaa gctagttctg   10800
cggtattttc aataaaagca ttgtttattc atgttccaat aataatatat gttgctcaaa   10860
ttatattatt gctctgttat ggacttgaca aagagtatcc acgcattatg aaggatttac   10920
aattaagaaa aagtaaaatg agtgcagaaa ataactaata aatgtacttg cagattttat   10980
acaatattgt aactgacata taaaaatgaa taagtgaaat aaggttttag tttcaataaa   11040
ataacaaata aataagaagt aaataatagg gagtgtcttt tctgatggtt tttttatcat   11100
tagagatgat actctctata ttttttaatt tgaatgtcaa aatatgccat taaaattcaa   11160
aagataataa ttaatagaaa gtaggttaat tttatgacaa aatataaaaa ttaatactga   11220
taatcacaaa aaacaattga catttgtacg aacaaatatt attataaatt taagaaatcg   11280
```

```
ctttcattta atggaatata agggactaat atggatacaa tgaagaccat aacagtaatt    11340
acaattgtta agattagtaa taaaaattta caatataaac ttgattttt aattaaaagg      11400 agagggatt taaaaatgat taaatttaaa tcaattagaa aaagcatgag gtcaattcta     11460
ttatgtggac ttgtattagt tctaagtgta ggtctcatgg catgtggaag tacaagtact    11520
tcaagttctg gtacaagcag taaaagaaa acgatagcat ttattccacc atcacttgta     11580
agcccatttt atactcaggc tgttacagga gcaaagcaag aagcagctaa agaaggattt    11640
aacataaaag tattggctcc tcaaacagaa gacgatttca atggattatt aaaaatagtt    11700
gaagacgtta taactcagca agttgatgct attgcaatat gtaccacaga tgataaaact    11760
atggctgctg ttgtaaaaaa agcaaatgat gcaaagatac cagttattgt atttaactca    11820
ttaagtccaa taagggtgc agatgtttat gcttatgttg gatatgacca aaaacaagca    11880
ggagctcagg ctgcagacta tttaggaact aaacttaaag acaagcaatt caatgttggt    11940
gtattagagg gtcttcctgg tgtatttaca gacaatagaa aaggtggatt tgtaaatgaa    12000
gctaaaaaat attcaaatgt aaagattgta gctacacaac cagctgattg gcagagagaa    12060
aaaggcatga atgttgcaac taaccttat caagctaata aggctataaa tatgtttta    12120 ggattgagtg atgaaatggc aataggtgca gcccaagctt ttaaatcagc aggggttaag    12180
gatggagtta ctattggtat agatggaaat ccagctactt tagattcaat cgcacaggga    12240
gaaactactg ctacaattta tacagatcca aaacaaattg gtaaagaaag tataatagat    12300
tgttctaaag cttaaaaagg tgaaaaaatg gcaaataaat tagatcagac aaagactttt    12360
gtagtagaca agagtaacgt tagtacttat aaagcaaaat aattctatat ttgctcttag    12420
aaaatgttag ctttaacatt ttctaagagt aaaatattta gttacgtaat ttgtggcaaa    12480
agggggggta atattgtcag aaactatatt gaaaatggag aacataacta aaagttttc    12540 aggagttaca gttcttaaaa attcgggaat tgaagttaaa aaaggagaag ttcatatttt    12600
acttggtgaa aatggtgcag gtaaatcaac tcttatgaag atactttctg gagcatattc    12660
aaaagatagt ggagacatta tactaaacgg aaacaaagta gagataaatt ctccaaaaga    12720
tgctgagaaa cttggaataa gcataattta tcaggaattt aatttagttc cctatatgac    12780
tgttgctgag aatatatatc ttggaagaga acctgaatcc aaggtacctg gtaaggttaa    12840
tttcaaaaaa atgtacaatg atgcacaaaa gatgattgat tacttaaatg tagatatacc    12900
tgtagataaa ccaataaaga attaggaat tgcccagcaa caaatggttg agatagcaaa    12960
agcactatcg gttcattctg atatcataat aatggatgag ccaacagcgg cactgacaga    13020 aaagaaata gataatttat ttaaaataat gagaaaaatt aaatctgaag gagtttctat    13080
aatatacatt tctcatagac ttgaggaatt tgctcaaatt ggtgatagag ttactgttat    13140
gagagatgga gaaactgtag aaacagttaa tatcaaaggt acatctatag atgaacttat    13200
aaaattaatg gtaggaagag aaattaaaga aaaatttcct aaaataaagg ttgatttagg    13260
agaagaaata ttaaggggtta agggattaac caaaaaagga gttttgaaa atataaattt    13320 cagtttgaga tcaggcgaaa tactaggatt ttctggtctt atgggtgcgg gaagaacaga    13380
agtaatgagg gctatatttg gtatagattc atttgattct ggtgaaatat atttaaaagg    13440
taaaaaagtt gaaataaatt cccctatgaa agcaataaaa aatggtatag gatttgtaac    13500
ggaaaataga agagatgaag gtcttgtttt acagatgggt gtaggtcaaa atataacctt    13560
agcatccctt ggcaaatata ttagtaatcc tataaaatta aatcttagaa aagagtcaa    13620 ggaaataaaa gattatatat ctaaattgtc aattaagtct tcaggatata gacaaattgc    13680
```

```
aggtacactg agcggtggaa accaacaaaa gattgttata gcaaagtggc tattatctga  13740
ttcaaaggtt ttaattgtgg atgaacctac tcgtggaata gatgtaggtg ctaaaataga  13800
aatttataat attatgaatg atttagttaa aagtggggta ggaataatta tggtttcttc  13860
agaacttcct gaagtacttg gcatgagtga tagaatatta gttatgtgta gagggaaaat  13920
aactggagaa ttaaataagg atgaggctac tcaagaaaaa ataatgcatt atgcaacagg  13980
aggtatagaa tgatgaatca gttagaagat actgaaaaaa agaaaaagac tagtataaat  14040
gacatactgg ataagctagg ggttgtcatt gcattagttg ttttaattgt agttatggct  14100
gtgttgtctc cagattttct tactgtaaaa aatgtattta acatattgca gcagattgca  14160
caaattggaa taatatctgt tggtatgact tttgtaatat tacttggagg aatcgactta  14220
tctgttggtt caattattgc atttacagga cttattatgg cattatgcat gaaagcagga  14280
atgtctgttg tgttagctat tttagtaggt attatactag gtgcagctat tggtttctta  14340
aatggaattt taatatcaaa ggttaaactc caaccttta tagctacact aggaactatg  14400
actatggcta gaggacttgc atatactata acaaatggac aaccagtata ttctttctca  14460
gctgggttta aaagctttgc tggatttatt ggagttgttc caattcctgc aattattatg  14520
gcagtaatat ttgcattagg ttattatgtg cttaaataca caaagtttgg aagatacatg  14580
tatgctattg gaggaaatag agtagcaagt aagctttcag gaataaatgt ggataaaatat  14640 gagatgttgg tttatacgat ttcaggaata tgctgtgcta tagctgctat aattttaaca  14700
gcaaggcttg attcagcagt accagttgca ggtgatggaa acgaacttga tgctatagcg  14760
gcagtagcta taggtggaac aagtatgacc ggtggagaag gcggtatagt tggaacactt  14820
attggtgcct taattatggg agtaattgcg aatggaatga acctactaga tgtgcaacag  14880
ggaccacaga ggtttgctaa aggtgcaatt ataatttag ctgtaggaat tgatgtaata  14940
agaaagaaaa gaacttctaa ataatacttt ggataaattc acaaggtgct tattaattt  15000 tattaaaaaa gtttcagatt atatccgaaa ctttttttgt atttaaatac tatagtttta  15060
tctccaatcc taaagaaat ttgtttatta gggttattta atgatatgta ataggtatca  15120
tatttattaa aaatgggtaa tatagttctc tgttagaata aattaagtat aaacatatcc  15180
atgtgtatct atgtaagaaa aatggtgaat ataagtagta taaggagaa atgcaaatt  15240 aagttataaa aataccggag taagtgaact gagttaagta aagctgtga tataataaat  15300 ttcgttgtca tggagattac agaaacagat taaatcaata gtttttatt taagaaaaa  15360 taataaaacg tattgacaga tgtaatttaa atgatatac tataaagg         15408
```

<210> SEQ ID NO 6
<211> LENGTH: 300
<212> TYPE: DNA
<213> ORGANISM: Clostridium autoethanogenum

<400> SEQUENCE: 6

```
atctgtatat tttttcccat tttaattatt tgtactataa tattcacactg agtgtattgc    60 atatttaaaa aatatttggt acaattagtt agttaaataa attctaaatt gtaaattatc   120
agaatcctta ttaaggaaat acatagattt aaggagaaat cataaaaagg tgtaatataa   180
actggctaaa attgagcaaa aattgagcaa ttaagacttt ttgattgtat ctttttatat   240
atttaaggta tataatctta tttatattgg gggaacttga tgaataaaca tattctagac   300
```

<210> SEQ ID NO 7

<211> LENGTH: 300
<212> TYPE: DNA
<213> ORGANISM: Clostridium autoethanogenum

<400> SEQUENCE: 7

```
atctgtat

| tcacactgtg | aattttttt | ataaattttt | cacactgtaa | aattcaatta | tgttattcaa | 120 |
| ctcattgtaa | ataccattca | catgttattt | ttgaccattc | gcatccgttt | ttttgcactt | 180 |
| tggaatattt | gggtatgaaa | atcaataaat | tcagactatt | ataaacatgt | aataaaattc | 240 |
| atataattaa | ttattaatga | actatttata | attattaaaa | attaaaaagg | aggtttttat | 300 |

<210> SEQ ID NO 12
<211> LENGTH: 2127
<212> TYPE: DNA
<213> ORGANISM: Clostridium autoethanogenum

<400> SEQUENCE: 12

| atgaatttat | ttcaaactgt | attcactggt | tcaaagcaag | ctttagcagc | tgctgaaggc | 60 |
| atagttaagc | aagctgttga | cgagaagggg | agagactata | aagtagcatt | tcctgatact | 120 |
| gaatattcat | taccagtaat | ttttgcagct | acaggaaaaa | agataactaa | tgtaggagaa | 180 |
| ttagaaggtg | cattagatat | agtaagaagt | ttgatagttg | aggaggaaat | gcttgataag | 240 |
| ctttttaaatt | caggacttgc | aacagctgtt | gcagcagaaa | ttatagaagc | tgcaaagtat | 300 |
| gttctttccg | atgctcctta | tgcagaacca | tgtgtaggt | ttatatctga | cccaataatt | 360 |
| cgttctcttg | gtgtaccact | tgttaccgga | gatataccag | gtgtagcagt | tatattagga | 420 |
| gaatgtccag | attcagaaac | cgcagctaaa | attataaagg | attatcaatc | aaaaggtctt | 480 |
| ttaacatgct | tagttggaaa | agtaattgat | caggcaatag | aaggaaaagt | taagatgggt | 540 |
| cttgacctca | gagttattcc | acttggatat | gatgttacat | ctgtaattca | cgttgtaact | 600 |
| atagctataa | gagctgcact | tatattcgga | ggaattaagg | gtggtcagtt | aaatgacata | 660 |
| ttgaaatata | cagcagaaag | ggtacctgct | tttgtaaatg | catttggacc | attaagtgaa | 720 |
| cttgtagttt | cagctggtgc | aggagctata | gcacttggat | tccctgtatt | aactgatcag | 780 |
| gttgtaccag | aagttcctac | attgttgtta | actcaaaaag | attatgataa | aatggttaaa | 840 |
| acttcattag | aagctagaaa | tataaagata | aagataactg | agatcccaat | tccagtttcc | 900 |
| tttgcagcag | catttgaagg | tgaaagaata | agaaagaatg | atatgcttgc | agagtttggt | 960 |
| ggaaataaga | ctaaagcttg | gaattagtt | atgtgtgcag | atcagggaga | agttgaagat | 1020 |
| cacaagatag | aagttatagg | accagatata | gatactatag | ataaggctcc | tggaagaatg | 1080 |
| cctcttggaa | tgcttattaa | agtaagtgga | acaaatatgc | agaaggattt | tgagccagtg | 1140 |
| cttgaaagaa | gacttcacta | cttcttaaac | tatatagaag | gagtaatgca | tgttggtcag | 1200 |
| agaaatctta | cttgggtaag | aataggtaag | gaagcttttg | aaaagggatt | tagattgaaa | 1260 |
| cattttggtg | aagtaatata | tgctaaaatg | ttagatgaat | ttggttcagt | tgtagataaa | 1320 |
| tgtgaagtaa | ctataataac | tgatccaggt | aaggctgaag | aattggaagg | caaatatgct | 1380 |
| gtaccaagat | ataagaaag | agatgcaaga | cttgaatcat | tagttgatga | aaaagttgat | 1440 |
| actttctatt | catgtaattt | gtgtcaatcc | tttgcacctg | cacatgtatg | tatagtaact | 1500 |
| cctgaaagac | ttggactttg | cggtgcagtt | tcatggcttg | atgctaaagc | tacacttgaa | 1560 |
| ttaaatccta | caggaccatg | tcaggccgtt | ccaaaagaag | gcgtggttga | tgaaaattta | 1620 |
| ggtatttggg | aaaaagtaaa | tgaaactgtt | tcaaaaattt | ctcaaggtgc | tgtaactagt | 1680 |
| gttacattat | acagtatatt | acaagatcca | atgacttcct | gtggatgttt | tgagtgtatt | 1740 |
| acaggtataa | tgccagaagc | aaatggtgtt | gtaatggtaa | acagagaatt | tggtgcaaca | 1800 |
| actcctcttg | gaatgacatt | tggtgaactt | gcatctatga | caggtggtgg | agttcagact | 1860 |

```
ccaggattta tgggacatgg aagacaattc atagcttcaa agaagtttat gaaaggtgaa    1920
ggcggacttg gcagaatagt ttggatgcca aaagaattaa aagactttgt tgcagaaaaa    1980
ttaaataaga cagcaaagga attatataat atagataatt ttgcagatat gatctgtgat    2040
gaaactatag ctacagaatc tgaagaagta gtaaaattct tggaagaaaa aggtcatcct    2100
gcattaaaga tggatccaat aatgtag                                       2127

<210> SEQ ID NO 13
<211> LENGTH: 2127
<212> TYPE: DNA
<213> ORGANISM: Clostridium autoethanogenum

<400> SEQUENCE: 13
atgaatttat tcaaactgt attcactggt tcaaagcaag ctttagcagc tgctgaaggc      60
atagttaagc aagctgttga cgagaagggt agagactata agtagcatt tcctgatact    120 gcatattcat taccagtaat ttttgcagct acaggaaaaa agataactaa tgtaggagaa    180
ttagaaggtg cattagatat agtaagaagt ttgatagttg aggaggaaat gcttgataag    240 ctttaaatt caggacttgc aacagctgtt gcagcagaaa ttatagaagc tgcaaagtat    300
gttctttccg atgctcctta tgcagaacca tgtgtaggat ttatatctga cccaataatt    360
cgttctcttg gtgtaccact tgttaccgga gatataccag gtgtagcagt tatattagga    420
gaatgtccag attcagaaac cgcagctaaa attataaagg attatcaatc aaaaggtctt    480
ttaacatgct tagttggaaa agtaattgat caggcaatag aaggaaaagt taagatgggt    540
cttgacctca gagttattcc acttggatat gatgttacat ctgtaattca cgttgtaact    600
atagctataa gagctgcact tatattcgga ggaattaagg gtggtcagtt aaatgacata    660
ttgaaatata cagcagaaag ggtacctgct tttgtaaatg catttggacc attaagtgaa    720
cttgtagttt cagctggtgc aggagctata gcacttggat tccctgtatt aactgatcag    780
gttgtaccag aagttcctac attgttgtta actcaaaaag attatgataa atgtgttaaa    840
acttcattag aagctagaaa tataaagata aagataactg agatcccaat tccagttttcc   900 tttgcagcag catttgaagg tgaaagaata agaaagaatg atatgcttgc agagtttggt    960
ggaaataaga ctaaagcttg gaattagtt atgtgtgcag atcagggaga agttgaagat   1020
cacaagatag aagttatagg accagatata gatactatag ataaggctcc tggaagaatg   1080
cctcttggaa tgcttattaa agtaagtgga acaaatatgc agaaggattt tgagccagtg   1140
cttgaaagaa gacttcacta cttcttaaac tatatagaag gagtaatgca tgttggtcag   1200
agaaatctta cttgggtaag aataggtaag gaagcttttg aaaagggatt tagattgaaa   1260
cattttggtg aagtaatata tgctaaaatg ttagatgaat ttggttcagt tgtagataaa   1320
tgtgaagtaa ctataataac tgatccaggt aaggctgaag aattggaagg caaatatgct   1380
gtaccaagat ataagaaag atgcaagaa cttgatcat tagttgatga aaagttgat   1440 actttctatt catgtaattt gtgtcaatcc tttgcacctg cacatgtatg tatagtaact   1500
cctgaaagac ttggactttg cggtgcagtt tcatggcttg atgctaaagc tacacttgaa   1560
ttaaatccta caggaccatg tcaggccgtt ccaaagaag gcgtggttga tgaaaattta   1620
ggtatttggg aaaagtaaaa tgaaactgtt tcaaaaattt ctcaaggtgc tgtaactagt   1680
gttacattat acagtatatt acaagatcca atgacttcct gtggatgttt tgagtgtatt   1740
acaggtataa tgccagaagc aaatggtgtt gtaatggtaa acagagaatt tggtgcaaca   1800
actcctcttg gaatgacatt tggtgaactt gcatctatga caggtggtgg agttcagact   1860
```

-continued

```
ccaggattta tgggacatgg aagacaattc atagcttcaa agaagtttat gaaaggtgaa    1920
ggcggacttg gcagaatagt ttggatgcca aagaattaa aagactttgt tgcagaaaaa    1980
ttaaataaga cagcaaagga attatataat atagataatt ttgcagatat gatctgtgat    2040
gaaactatag ctacagaatc tgaagaagta gtaaaattct tggaagaaaa aggtcatcct    2100
gcattaaaga tggatccaat aatgtag                                        2127
```

<210> SEQ ID NO 14
<211> LENGTH: 708
<212> TYPE: PRT
<213> ORGANISM: Clostridium autoethanogenum

<400> SEQUENCE: 14

```
Met Asn Leu Phe Gln Thr Val Phe Thr Gly Ser Lys Gln Ala Leu Ala
1               5                   10                  15

Ala Ala Glu Gly Ile Val Lys Gln Ala Val Asp Glu Lys Gly Arg Asp
            20                  25                  30

Tyr Lys Val Ala Phe Pro Asp Thr Glu Tyr Ser Leu Pro Val Ile Phe
        35                  40                  45

Ala Ala Thr Gly Lys Lys Ile Thr Asn Val Gly Glu Leu Glu Gly Ala
    50                  55                  60

Leu Asp Ile Val Arg Ser Leu Ile Val Glu Glu Met Leu Asp Lys
65                  70                  75                  80

Leu Leu Asn Ser Gly Leu Ala Thr Ala Val Ala Ala Glu Ile Glu
                85                  90                  95

Ala Ala Lys Tyr Val Leu Ser Asp Ala Pro Tyr Ala Glu Pro Cys Val
            100                 105                 110

Gly Phe Ile Ser Asp Pro Ile Ile Arg Ser Leu Gly Val Pro Leu Val
        115                 120                 125

Thr Gly Asp Ile Pro Gly Val Ala Val Ile Leu Gly Glu Cys Pro Asp
    130                 135                 140

Ser Glu Thr Ala Ala Lys Ile Ile Lys Asp Tyr Gln Ser Lys Gly Leu
145                 150                 155                 160

Leu Thr Cys Leu Val Gly Lys Val Ile Asp Gln Ala Ile Glu Gly Lys
                165                 170                 175

Val Lys Met Gly Leu Asp Leu Arg Val Ile Pro Leu Gly Tyr Asp Val
            180                 185                 190

Thr Ser Val Ile His Val Val Thr Ile Ala Ile Arg Ala Ala Leu Ile
        195                 200                 205

Phe Gly Gly Ile Lys Gly Gly Gln Leu Asn Asp Ile Leu Lys Tyr Thr
    210                 215                 220

Ala Glu Arg Val Pro Ala Phe Val Asn Ala Phe Gly Pro Leu Ser Glu
225                 230                 235                 240

Leu Val Val Ser Ala Gly Ala Gly Ala Ile Ala Leu Gly Phe Pro Val
                245                 250                 255

Leu Thr Asp Gln Val Val Pro Glu Val Pro Thr Leu Leu Thr Gln
            260                 265                 270

Lys Asp Tyr Asp Lys Met Val Lys Thr Ser Leu Glu Ala Arg Asn Ile
        275                 280                 285

Lys Ile Lys Ile Thr Glu Ile Pro Ile Pro Val Ser Phe Ala Ala Ala
    290                 295                 300

Phe Glu Gly Glu Arg Ile Arg Lys Asn Asp Met Leu Ala Glu Phe Gly
305                 310                 315                 320
```

```
Gly Asn Lys Thr Lys Ala Trp Glu Leu Val Met Cys Ala Asp Gln Gly
                325                 330                 335

Glu Val Glu Asp His Lys Ile Glu Val Ile Gly Pro Asp Ile Asp Thr
            340                 345                 350

Ile Asp Lys Ala Pro Gly Arg Met Pro Leu Gly Met Leu Ile Lys Val
        355                 360                 365

Ser Gly Thr Asn Met Gln Lys Asp Phe Glu Pro Val Leu Glu Arg Arg
    370                 375                 380

Leu His Tyr Phe Leu Asn Tyr Ile Glu Gly Val Met His Val Gly Gln
385                 390                 395                 400

Arg Asn Leu Thr Trp Val Arg Ile Gly Lys Glu Ala Phe Glu Lys Gly
                405                 410                 415

Phe Arg Leu Lys His Phe Gly Glu Val Ile Tyr Ala Lys Met Leu Asp
            420                 425                 430

Glu Phe Gly Ser Val Val Asp Lys Cys Glu Val Thr Ile Ile Thr Asp
        435                 440                 445

Pro Gly Lys Ala Glu Glu Leu Gly Lys Tyr Ala Val Pro Arg Tyr
    450                 455                 460

Lys Glu Arg Asp Ala Arg Leu Glu Ser Leu Val Asp Glu Lys Val Asp
465                 470                 475                 480

Thr Phe Tyr Ser Cys Asn Leu Cys Gln Ser Phe Ala Pro Ala His Val
                485                 490                 495

Cys Ile Val Thr Pro Glu Arg Leu Gly Leu Cys Gly Ala Val Ser Trp
            500                 505                 510

Leu Asp Ala Lys Ala Thr Leu Glu Leu Asn Pro Thr Gly Pro Cys Gln
        515                 520                 525

Ala Val Pro Lys Glu Gly Val Val Asp Glu Asn Leu Gly Ile Trp Glu
    530                 535                 540

Lys Val Asn Glu Thr Val Ser Lys Ile Ser Gln Gly Ala Val Thr Ser
545                 550                 555                 560

Val Thr Leu Tyr Ser Ile Leu Gln Asp Pro Met Thr Ser Cys Gly Cys
                565                 570                 575

Phe Glu Cys Ile Thr Gly Ile Met Pro Glu Ala Asn Gly Val Val Met
            580                 585                 590

Val Asn Arg Glu Phe Gly Ala Thr Thr Pro Leu Gly Met Thr Phe Gly
        595                 600                 605

Glu Leu Ala Ser Met Thr Gly Gly Val Gln Thr Pro Gly Phe Met
    610                 615                 620

Gly His Gly Arg Gln Phe Ile Ala Ser Lys Lys Phe Met Lys Gly Glu
625                 630                 635                 640

Gly Gly Leu Gly Arg Ile Val Trp Met Pro Lys Glu Leu Lys Asp Phe
                645                 650                 655

Val Ala Glu Lys Leu Asn Lys Thr Ala Lys Glu Leu Tyr Asn Ile Asp
            660                 665                 670

Asn Phe Ala Asp Met Ile Cys Asp Glu Thr Ile Ala Thr Glu Ser Glu
        675                 680                 685

Glu Val Val Lys Phe Leu Glu Glu Lys Gly His Pro Ala Leu Lys Met
    690                 695                 700

Asp Pro Ile Met
705

<210> SEQ ID NO 15
<211> LENGTH: 708
<212> TYPE: PRT
```

<213> ORGANISM: Clostridium autoethanogenum

<400> SEQUENCE: 15

Met Asn Leu Phe Gln Thr Val Phe Thr Gly Ser Lys Gln Ala Leu Ala
1               5                   10                  15

Ala Ala Glu Gly Ile Val Lys Gln Ala Val Asp Glu Lys Gly Arg Asp
            20                  25                  30

Tyr Lys Val Ala Phe Pro Asp Thr Ala Tyr Ser Leu Pro Val Ile Phe
        35                  40                  45

Ala Ala Thr Gly Lys Lys Ile Thr Asn Val Gly Glu Leu Glu Gly Ala
    50                  55                  60

Leu Asp Ile Val Arg Ser Leu Ile Val Glu Glu Met Leu Asp Lys
65                  70                  75                  80

Leu Leu Asn Ser Gly Leu Ala Thr Ala Val Ala Glu Ile Ile Glu
                85                  90                  95

Ala Ala Lys Tyr Val Leu Ser Asp Ala Pro Tyr Ala Glu Pro Cys Val
            100                 105                 110

Gly Phe Ile Ser Asp Pro Ile Ile Arg Ser Leu Gly Val Pro Leu Val
            115                 120                 125

Thr Gly Asp Ile Pro Gly Val Ala Val Ile Leu Gly Glu Cys Pro Asp
    130                 135                 140

Ser Glu Thr Ala Ala Lys Ile Ile Lys Asp Tyr Gln Ser Lys Gly Leu
145                 150                 155                 160

Leu Thr Cys Leu Val Gly Lys Val Ile Asp Gln Ala Ile Glu Gly Lys
                165                 170                 175

Val Lys Met Gly Leu Asp Leu Arg Val Ile Pro Leu Gly Tyr Asp Val
            180                 185                 190

Thr Ser Val Ile His Val Val Thr Ile Ala Ile Arg Ala Ala Leu Ile
        195                 200                 205

Phe Gly Gly Ile Lys Gly Gly Gln Leu Asn Asp Ile Leu Lys Tyr Thr
    210                 215                 220

Ala Glu Arg Val Pro Ala Phe Val Asn Ala Phe Gly Pro Leu Ser Glu
225                 230                 235                 240

Leu Val Val Ser Ala Gly Ala Gly Ala Ile Ala Leu Gly Phe Pro Val
                245                 250                 255

Leu Thr Asp Gln Val Val Pro Glu Val Pro Thr Leu Leu Leu Thr Gln
            260                 265                 270

Lys Asp Tyr Asp Lys Met Val Lys Thr Ser Leu Glu Ala Arg Asn Ile
        275                 280                 285

Lys Ile Lys Ile Thr Glu Ile Pro Ile Pro Val Ser Phe Ala Ala Ala
    290                 295                 300

Phe Glu Gly Glu Arg Ile Arg Lys Asn Asp Met Leu Ala Glu Phe Gly
305                 310                 315                 320

Gly Asn Lys Thr Lys Ala Trp Glu Leu Val Met Cys Ala Asp Gln Gly
                325                 330                 335

Glu Val Glu Asp His Lys Ile Glu Val Ile Gly Pro Asp Ile Asp Thr
            340                 345                 350

Ile Asp Lys Ala Pro Gly Arg Met Pro Leu Gly Met Leu Ile Lys Val
        355                 360                 365

Ser Gly Thr Asn Met Gln Lys Asp Phe Glu Pro Val Leu Glu Arg Arg
    370                 375                 380

Leu His Tyr Phe Leu Asn Tyr Ile Glu Gly Val Met His Val Gly Gln
385                 390                 395                 400

```
Arg Asn Leu Thr Trp Val Arg Ile Gly Lys Glu Ala Phe Glu Lys Gly
                405                 410

```
tatgatctag atagtgttgg aatattacag gtggcaagca ttttaaatgg tggaaaagac      420
atgggtggaa ctgatttaaa agggaaacca gatttctttt taggggcctg tgttacacct      480
agatatgatc cgttagagct tcaagttata aagatgaaga agaaaattaa agctggagct      540
aaattctttc aaactcaagc tgtttatgat atggaaactt taaagaaatt caaagaagag      600
actaaagctc aaggtgtaga tgctaaagtt atggtaggca taatacccttt aaagtcagct      660 ggtatggcta aatacatgaa taaaaacgta cctggtatat tcgtacctga tgaacttata      720
gatagaatga agaatgctga ggataaagtt caagaaggca taaagatagc aggagaattt      780
ataaaggccg taaaagaatc aggactttgc gatggagttc atataatggc aattggtgcg      840
gaagaaaatg tgccattaat attggatgaa gcaggattat aa                         882

<210> SEQ ID NO 17
<211> LENGTH: 882
<212> TYPE: DNA
<213> ORGANISM: Clostridium autoethanogenum

<400> SEQUENCE: 17
atgagcttat tgaaggaagc ttttgaaaag ggagagtttg caattacagc tgaaatggca       60
cctccaaagg gaacggatct ttctcattta attgaatgtg ccaaaaagat aaaaggaaga      120
gttcagggag ttaatgtaac ggattttcag tctgctacat aaaagctac atctttagct       180 acttgtaaag tattaaaaga tgcaggatta gagcctgtat tcaaataac aggaagagat       240 agaaacagaa tagcaattca aggagaattg ttatctgcag gtgttttgg aattgaaaat       300 gttttagctc ttactgggga ttatactgct acaggagatc accctggtgc aaagccagtt      360
tatgatctag atagtgttgg aatattacag gtggcaagca ttttaaatgg tggaaaagac      420
atgggtggaa ctgatttaaa agggaaacca gatttctttt taggggcctg tgttacacct      480
agatatgatc cgttagagct tcaagttata aagatgaaga agaaaattaa agctggagct      540
aaattctttc aaactcaagc tgtttatgat atggaaactt taaagaaatt caaagaagag      600
actaaagctc aaggtgtaga tgctaaagtt atggtaggca taatacccttt aaagtcagct      660 ggtatggcta aatacatgaa taaaaacgta cctggtatat tcgtacctga tgaacttata      720
gatagaatga agaatgctga ggataaagtt caagaaggca taaagatagc aggagaattt      780
ataaaggccg taaaagaatc aggactttgc gatggagttc atataatggc aattggtgcg      840
gaagaaaatg tgccattaat attggatgaa gcaggattat aa                         882
```

BACTERIA AND METHODS OF USE THEREOF

CROSS REFERENCE TO RELATED APPLICATIONS

This application is a continuation of U.S. patent application Ser. No. 13/812,029 filed Jan. 24, 2013, which is a national stage of International Patent Application PCT/NZ2011/000144 filed Jul. 28, 2011, which is a nonprovisional of U.S. Patent Application 61/368,486 filed Jul. 28, 2010, the entirety of which are incorporated herein by reference.

FIELD OF THE INVENTION

This invention relates generally to the field of microbial fermentation of gases. It more particularly relates to a novel class of bacteria with improved efficiency in the production of ethanol by anaerobic fermentation of substrates containing carbon monoxide (CO).

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, free, energy-rich by-product of the incomplete combustion of organic materials such as coal or oil and oil derived products. For example, the steel industry in Australia is reported to produce and release into the atmosphere over 500,000 tonnes of CO annually.

Catalytic processes may be used to convert gases consisting primarily of CO and/or CO and hydrogen (H2) into a variety of fuels and chemicals. Micro-organisms may also be used to convert these gases into fuels and chemicals.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase acetyl CoA synthase (CODH/ACS) pathway). A large number of anaerobic organisms including carboxydotrophic, photosynthetic, methanogenic and acetogenic organisms have been shown to metabolize CO to various end products, namely CO2, H2, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, CO2 and H2 via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is always associated with co-production of acetate and/or acetic acid. As some of the available carbon is converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

0011 Microbial fermentation of CO in the presence of H2 can lead to substantially complete carbon transfer into an alcohol. However, in the absence of sufficient H2, some of the CO is converted into alcohol, while a significant portion is converted to CO2 as shown in the following equations:

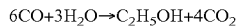

$$6CO + 3H_2O \rightarrow C_2H_5OH + 4CO_2$$

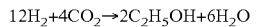

$$12H_2 + 4CO_2 \rightarrow 2C_2H_5OH + 6H_2O$$

The production of $CO_2$ represents inefficiency in overall carbon capture and if released, also has the potential to contribute to Green House Gas emissions.

WO2007/117157 describes a process that produces alcohols, particularly ethanol, by anaerobic fermentation of gases containing carbon monoxide. Acetate produced as a by-product of the fermentation process is converted into hydrogen gas and carbon dioxide gas, either or both of which may be used in the anaerobic fermentation process.

WO2008/115080 describes a process for the production of alcohol(s) in multiple fermentation stages. By-products produced as a result of anaerobic fermentation of gas(es) in a first bioreactor can be used to produce products in a second bioreactor. Furthermore, by-products of the second fermentation stage can be recycled to the first bioreactor to produce products.

WO2009/064200 describes a novel class of bacteria which has improved efficiency in the production of ethanol by anaerobic fermentation of substrates containing carbon monoxide.

It would be beneficial to provide micro-organisms that are capable of fermentation of gases containing carbon monoxide to ethanol at increased efficiency, that is micro-organisms capable of improved uptake of carbon monoxide, of producing more ethanol, and/or a greater ratio of ethanol to acetate from the same substrate, than do micro-organisms of the prior art.

It is an object of the present invention to provide a new class of bacteria which overcomes one or more of the limitations of the prior art in the conversion of gaseous sources containing CO into ethanol, or to at least provide the public with a useful choice.

SUMMARY OF THE INVENTION

In a first aspect the invention provides a biologically pure isolate of a bacterium wherein the bacterium is capable of producing products including ethanol and optionally acetate, by anaerobic fermentation of a substrate comprising CO, at a specific productivity of at least about 2 g ethanol/L fermentation broth/gram of biomass/day.

In other embodiments, the bacterium is capable of producing ethanol at a specific productivity of at least about 3 g ethanol/L fermentation broth/gram of biomass/day, at least about 4 g ethanol/L fermentation broth/gram of biomass/day, at least about 5 g ethanol/L fermentation broth/gram of biomass/day, at least about 6 g ethanol/L fermentation broth/gram of biomass/day or at least about 7 g ethanol/L fermentation broth/gram of biomass/day.

In another aspect the invention provides a biologically pure isolate of a bacterium wherein the bacterium is capable of producing products including ethanol and optionally acetate, by anaerobic fermentation of a substrate comprising CO, at a productivity of at least about 10 g ethanol/L of fermentation broth/day.

In other embodiments, the bacterium is capable of producing ethanol at a productivity of at least about 20 g ethanol/L of fermentation broth/day, at least about 30 g ethanol/L of fermentation broth/day, at least about 40 g ethanol/L of fermentation broth/day or at least about 50 g ethanol/L of fermentation broth/day, or at least about 60 g ethanol/L of fermentation broth/day, or at least about 70 g ethanol/L of fermentation broth/day.

In another aspect the invention provides a biologically pure isolate of a bacterium wherein the bacterium is capable of producing products including ethanol and optionally acetate, by anaerobic fermentation of a substrate comprising CO, and wherein the bacterium is capable of a specific uptake of CO of at least about 1.0 mMol CO/min/g of biomass.

In one embodiment the bacterium is capable of a specific uptake of CO of at least about 1.2 mMol CO/min/g biomass, at least about 1.4 mMol CO/min/g of biomass, at least about 1.6 mMol CO/min/g of biomass, at least about 1.8 mMol CO/min/g of biomass, or at least about 2.0 mMol CO/min/g of biomass. In one particular embodiment, the bacterium is capable of a specific uptake of CO of at least about 1.2 mMol CO/min/g biomass.

In another aspect the invention provides a biologically pure isolate of a bacterium wherein the bacterium is capable of producing products including ethanol and optionally acetate, by anaerobic fermentation of a substrate comprising CO, and wherein the bacterium is capable of a specific growth rate of at least about 0.8 day$^{-1}$.

In certain embodiments the bacterium is capable of a specific growth rate of at least about 1.0 day$^{-1}$, at least about 1.2 day$^{-1}$, at least about 1.4 day$^{-1}$, at least about 1.6 day$^{-1}$, at least about 1.8 day$^{-1}$ or at least about 2.0 day$^{-1}$.

In another aspect the invention provides a biologically pure isolate of a bacterium wherein the bacterium is capable of producing products including ethanol and optionally acetate, by anaerobic fermentation of a substrate comprising CO, and wherein the bacterium is capable of producing ethanol at an ethanol to acetate ratio of at least about 2:1.

In certain embodiments the bacterium is capable of producing ethanol at an ethanol to acetate ratio of at least about 3:1, of at least about 4:1, of at least about 5:1, of at least about 7:1 or of at least about 10:1.

In one embodiment, the bacterium is capable of producing ethanol with substantially no acetate.

In another aspect the invention provides a biologically pure isolate of a bacterium wherein the bacterium is capable of producing products including ethanol and optionally acetate, by anaerobic fermentation of a substrate comprising CO, and wherein the bacterium is capable of tolerating alcohol of up to about 30 g/L of fermentation broth.

In certain embodiment the bacterium is capable of tolerating alcohol of up to about 40 g/L of fermentation broth, of up to about 50 g/L of fermentation broth, of up to about 60 g/L of fermentation broth, or of up to about 70 g/L of fermentation broth.

In another aspect the invention provides a biologically pure isolate of a bacterium wherein the bacterium is capable of producing products including ethanol and optionally acetate, by anaerobic fermentation of a substrate comprising CO, and wherein the bacterium has two or more of the following characteristics:
  is capable of producing products including ethanol and optionally acetate, by anaerobic fermentation of a substrate comprising CO, at a specific productivity of at least about 2 g of ethanol/L of fermentation broth/gram of biomass/day;
  is capable of producing ethanol at a concentration of at least about 10 g ethanol/L of fermentation broth/day;
  is capable of a specific uptake of CO of at least about 1.0 mMol CO/min/g of biomass;
  is capable of a growth rate of at least about 1.0 g/day;
  is capable of producing ethanol at an ethanol to acetate ratio of at least about 2:1; and, is capable of tolerating alcohol of up to about 30 g/L of broth.

In one embodiment, the bacteria of the invention are derived from *Clostridium autoethanogenum*. In a preferred embodiment, the bacterium of the invention is a strain of *Clostridium autoethanogenum*.

In a particular embodiment the bacterium has the defining characteristics of the *Clostridium autoethanogenum* strain deposited at DSMZ under the accession number DMS23693. In one embodiment the bacterium is the *Clostridium autoethanogenum* strain deposited at DSMZ under the accession number DMS23693.

In a further aspect the invention provides a biologically pure isolate of the *Clostridium autoethanogenum* strain deposited at DSMZ under the accession number DMS23693

In another aspect, the invention provides a method for the production of one or more alcohols comprising fermenting a substrate comprising CO using a bacterium as herein before described.

In one embodiment the method comprises the steps of:
  (a) providing a substrate comprising CO to a bioreactor containing a culture of a bacterium of the invention; and
  (b) anaerobically fermenting the culture in the bioreactor to produce one or more alcohols.

In a further aspect, the invention provides a method for reducing the total atmospheric carbon emissions from an industrial process, the method comprising:
  (a) capturing CO-containing gas produced as a result of the industrial process, before the gas is released into the atmosphere;
  (b) the anaerobic fermentation of the CO-containing gas to produce one or more alcohols by a culture containing one or more bacterium of the invention.

In one embodiment of the method aspects, the fermentation is conducted at a temperature of about 34° C. to about 37° C. In one preferred embodiment, the fermentation is conducted at a temperature of about 34° C.

In certain embodiments of the method aspects, acetate is produced as a by-product of the fermentation. Preferably the one or more alcohols produced includes ethanol.

In particular embodiments of the method aspects, the bacterium is maintained in an aqueous culture medium.

In particular embodiments of the method aspects, the fermentation of the substrate takes place in a bioreactor.

In certain embodiments the substrate comprises at least about 25% CO by volume, at least about 30% CO by volume, at least about 40% CO by volume, at least about 50% CO by volume, at least about 65% CO by volume or at least about 70% CO by volume. In particular embodiments the substrate comprises at least about 75% CO by volume, at least about 80% CO by volume, at least about 85% CO by volume, at least about 90% CO by volume or at least about 95% CO by volume.

In one embodiment the substrate comprises about 30% or less $H_2$ by volume. In another embodiments, the substrate comprises about 20% or less $H_2$ by volume, about 15% or less $H_2$ by volume, about 10% or less $H_2$ by volume, about 5% or less $H_2$ by volume, about 4% or less $H_2$ by volume, about 3% or less $H_2$ by volume, about 2% or less $H_2$ by volume, about 1% or less $H_2$ by volume, or substantially no $H_2$.

In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In certain embodiments the substrate comprising CO is a gaseous substrate containing CO.

In certain embodiments, the gaseous substrate comprises a gas obtained as a by-product of an industrial process.

In certain embodiments, the industrial process is selected from the group consisting of ferrous metal products manufacturing, non-ferrous products manufacturing, petroleum refining processes, gasification of biomass, gasification of coal, electric power production, carbon black production, ammonia production, methanol production and coke manufacturing.

In one embodiment, the gaseous substrate may comprise a gas obtained from a steel mill.

In another embodiment, the gaseous substrate may comprise automobile exhaust fumes.

In certain embodiments of the method aspects the alcohol is recovered from the fermentation broth, the fermentation broth being the aqueous culture medium comprising bacterial cells and the alcohol.

In certain embodiments acetate is produced as a by-product of the fermentation.

In a further embodiment the alcohol and the acetate are recovered from the broth.

Although the invention is broadly as defined above, it is not limited thereto and also includes embodiments of which the following description provides examples.

BRIEF DESCRIPTION OF THE DRAWINGS

The invention will now be described in detail with reference to the accompanying Figures in which:

FIG. 5: SEQ ID NO: 1: Nucleotide sequence of DNA mismatch repair protein MutS gene in strain LZ1561

FIG. 6: SEQ ID NO: 2: Nucleotide sequence of DNA mismatch repair protein MutS gene in strain LZ1560

FIG. 7: SEQ ID NO: 3: Amino Acid sequence of DNA mismatch repair protein MutS gene in strain LZ1561

FIG. 8: SEQ ID NO: 4: Amino Acid sequence of DNA mismatch repair protein MutS gene in strain LZ1560

FIGS. 9A-9F: SEQ ID NO: 5: Nucleotide sequence found to be re-arranged in strains LZ561 and LZ1560

FIG. 10: SEQ ID NO: 6: Nucleotide sequence of putative promoter region of $F_1F_O$ ATP synthase operon in strain LZ1561

FIG. 11: SEQ ID NO: 7: Nucleotide sequence of putative promoter region of $F_1F_O$ ATP synthase operon in strain LZ1560

FIG. 12: SEQ ID NO: 8: Nucleotide sequence of putative promoter region of Rnf complex operon in strain LZ1561

FIG. 13: SEQ ID NO: 9: Nucleotide sequence of putative promoter region of Rnf complex operon in strain LZ1560

FIG. 14: SEQ ID NO: 10: Nucleotide sequence of putative promoter region of carbon starvation protein in strain LZ1561

FIG. 15: SEQ ID NO: 11: Nucleotide sequence of putative promoter region of carbon starvation protein in strain LZ1560

FIG. 16: SEQ ID NO: 12: Nucleotide sequence of CO dehydrogenase/CO-methylating acetyl-CoA synthase complex beta subunit gene in strain LZ1561

FIG. 17: SEQ ID NO: 13: Nucleotide sequence of CO dehydrogenase/CO-methylating acetyl-CoA synthase complex beta subunit gene in strain LZ1560

FIG. 18: SEQ ID NO: 14: Amino Acid sequence of CO dehydrogenase/CO-methylating acetyl-CoA synthase complex beta subunit gene in strain LZ1561

FIG. 19: SEQ ID NO: 15: Amino Acid sequence of CO dehydrogenase/CO-methylating acetyl-CoA synthase complex beta subunit gene in strain LZ1560

FIG. 20: SEQ ID NO: 16: Nucleotide sequence of 5,10-methylenetetrahydrofolate reductase gene in strain LZ1561

FIG. 21: SEQ ID NO: 17: Nucleotide sequence of 5,10-methylenetetrahydrofolate reductase gene in strain LZ1560

DETAILED DESCRIPTION OF THE INVENTION

Figure 1:
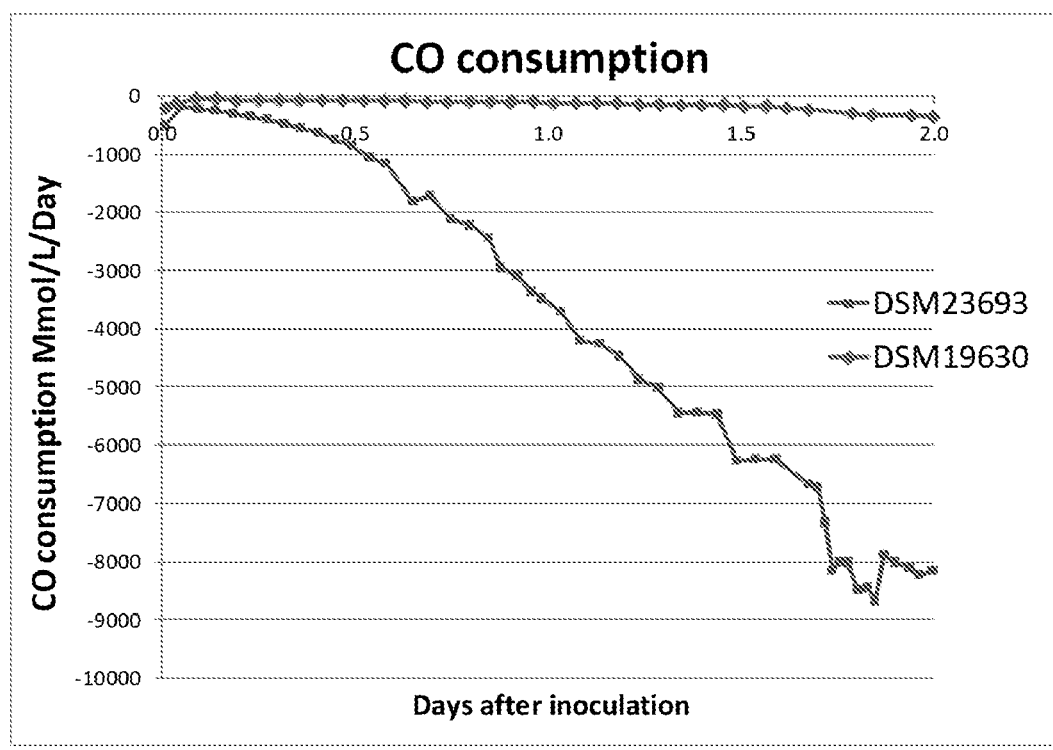
FIG. 1: Shows the CO consumption of DSM19630 and DSM23693

The inventors have developed novel bacteria. The bacteria are characterised by having one or more of a number of unexpected properties (as outlined herein after), and in one preferred embodiment all of these properties. The use of these novel bacteria in anaerobic fermentation processes provides an unexpected benefit over existing strains of bacteria which may allow for an increase in the overall efficiency of a fermentation process for producing products such as ethanol and/or acetate.

Accordingly, in broad terms, in one aspect, the present invention relates to a novel bacterium and a biologically pure isolate of a bacterium with increased efficiency in an anaerobic fermentation process. In one aspect the bacterium is capable of producing an alcohol, preferably ethanol, from a substrate comprising CO.

In a further aspect, the invention relates to processes for producing an alcohol, preferably ethanol, by anaerobic fermentation of a CO-containing substrate by the bacteria of the invention.

Definitions

Unless otherwise defined, the following terms as used throughout this specification are defined as follows:

A "substrate containing CO", a "substrate comprising CO" and like terms should be understood to include any substrate in which carbon monoxide is available to bacteria for growth and/or fermentation, for example. In particular embodiments of the invention the "substrate containing CO" is gaseous. Such substrates may be referred to herein as "gaseous substrates containing CO", "gaseous substrates comprising CO" and the like.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator for aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO".

The terms "increasing the efficiency", "increased efficiency" and the like, when used in relation to a fermentation process, include, but are not limited to, increasing one or more of: the rate of growth of micro-organisms catalysing the fermentation, the uptake or consumption of CO by the micro-organisms, the volume of desired product (such as alcohols) produced per volume of substrate (such as CO) consumed, the concentration of the desired product (such as alcohols) produced in the culture medium, the rate of production or level of production of the desired product, and the relative proportion of the desired product produced compared with other by-products of the fermentation.

The term "acetate" includes both acetate salt alone and a mixture of molecular or free acetic acid and acetate salt, such as the mixture of acetate salt and free acetic acid present in a fermentation broth as described herein. The ratio of molecular acetic acid to acetate in the fermentation broth is dependent upon the pH of the system.

The term "bioreactor" includes a fermentation device consisting of one or more vessels and/or towers or piping arrangement, which includes the Continuous Stirred Tank Reactor (CSTR), Immobilized Cell Reactor (ICR), Trickle Bed Reactor (TBR), Bubble Column, Gas Lift Fermenter, Static Mixer, or other vessel or other device suitable for gas-liquid contact.

The term "alcohol tolerance" as used herein should be taken to refer to the level of alcohol, preferably ethanol, that a bacterium or population of bacteria will tolerate while continuing to survive, grow and/or to produce at least a level of the desired product.

Bacteria of the invention, or cultures or isolates thereof, may be described to be in an "isolated" or "biologically pure" form. These terms are intended to mean that the bacteria have been separated from an environment or one or more constituents, cellular or otherwise, which they may be associated with if found in nature or otherwise. The terms "isolated" or "biologically pure" should not be taken to indicate the extent to which the bacteria have been purified. However, in one embodiment the isolates or cultures of the bacteria contain a predominance of the bacteria of the invention.

The invention provides a biologically pure isolate of a bacterium wherein the bacterium is capable of producing products including ethanol and optionally acetate, by anaerobic fermentation of a substrate containing CO and wherein the bacterium is capable of one or more of:

producing ethanol at a specific productivity of about 2 g ethanol/L fermentation broth/gram of biomass/day;

producing ethanol at a productivity of at least about 10 g/L of fermentation broth/day;

a specific uptake of CO of at least about 1.0 mMol CO/min/g of biomass;

a specific growth rate of at least about 0.8 $day^{-1}$;

producing ethanol at an ethanol to acetate ratio of at least about 2:1; and, tolerating alcohol of up to about 30 g/L of broth.

In a preferred embodiment, a bacterium of the invention is capable of two, three, four, or five of the above features.

In certain embodiments, the bacterium is capable of producing ethanol at a specific productivity of at least about 3 g ethanol/L fermentation broth/gram of biomass/day, at least about 4 g ethanol/L fermentation broth/gram of biomass/day, at least about 5 g ethanol/L fermentation broth/gram of biomass/day, at least about 6 g ethanol/L fermentation broth/gram of biomass/day or at least about 7 g ethanol/L fermentation broth/gram of biomass/day.

In certain embodiments, the bacterium is capable of producing ethanol at a productivity of at least about 20 g ethanol/L of fermentation broth/day, at least about 30 g ethanol/L of fermentation broth/day, at least about 40 g ethanol/L of fermentation broth/day or at least about 50 g ethanol/L of fermentation broth/day. The maximum value takes into account stoichiometry, CO uptake and ethanol stripping.

In certain embodiments the bacterium is capable of a specific uptake of CO of at least about 1.2 mMol CO/min/g biomass, at least about 1.4 mMol CO/min/g of biomass, at least about 1.6 mMol CO/min/g of biomass, at least about 1.8 mMol CO/min/g of biomass, or at least about 2.0 mMol CO/min/g of biomass. In one particular embodiment, the bacterium is capable of a specific uptake of CO of at least about 1.2 mMol CO/min/g biomass.

In certain embodiments the bacterium is capable of a specific growth rate of at least about 1.0 $day^{-1}$, at least about 1.2 $day^{-1}$, at least about 1.4 $day^{-1}$, at least about 1.6 $day^{-1}$, at least about 1.8 $day^{-1}$ or at least about 2.0 $day^{-1}$.

In certain embodiments the bacterium is capable of producing ethanol at an ethanol to acetate ratio of at least about 3:1, of at least about 4:1, of at least about 5:1, of at least about 7:1 or of at least about 10:1. In one particular embodiment, there is no net production of acetate during fermentation.

In certain embodiments the bacterium is capable of tolerating alcohol of up to about 40 g/L of fermentation broth, of up to about 50 g/L of fermentation broth, or of up to about 60 g/L of fermentation broth. In one particular embodiment, the bacterium is capable of tolerating alcohol of up to about 70 g/L of fermentation broth.

In a preferred embodiment, the bacteria of the invention are derived from *Clostridium autoethanogenum*. In a more preferred embodiment of the invention the bacteria are derived from *Clostridium autoethanogenum* strain DSM19630 (DSMZ, Germany) (described in WO2009/064200).

In a preferred embodiment, the bacterium of the invention is a strain of *Clostridium autoethanogenum*.

*Clostridium autoethanogenum* is described, for example, in Abrini et al; *Clostridium autoethanogenum*, sp. nov., an anaerobic bacterium that produces ethanol from carbon monoxide, Arch Microbiol (1994) 161:345-351.

In certain embodiments of the invention, the bacteria have the defining characteristics of *Clostridium autoethanogenum* strain DSM23693 deposited at DSMZ, Germany, in accordance with the Budapest Treaty, on 7 Jun. 2010. In a particular embodiment, the bacterium is *Clostridium autoethanogenum* strain DSM23693.

The invention also relates to bacteria derived from the bacteria of the invention.

The bacteria of certain embodiments of the invention are capable of an increased alcohol production rate, an increased growth rate, an increased CO consumption or update rate, a higher alcohol to acid production ratio, and/or an increased tolerance to alcohol. This provides a benefit over other strains of *Clostridia* sp including *Clostridium autoethanogenum*. Therefore, use of bacteria of the present invention may increase the overall efficiency of a fermentation process for producing products such as acetate and/or ethanol.

In certain embodiments the bacteria of the invention are capable of the productivity, growth rates, alcohol to acid ratio, CO consumption and alcohol tolerance mentioned herein before at elevated levels of CO in the gaseous substrate. For example, the gaseous substrate may comprise at least about 50% CO by volume, at least about 65% CO by volume, or at least about 70% CO by volume. In certain embodiments the gaseous substrate comprises at least about 80% CO by volume, or at least about 85% CO by volume, or at least about 90% CO by volume or at least about 95% CO by volume.

Similarly the productivity, growth rates, alcohol to acid ratio, CO consumption and alcohol tolerance herein before described are achievable in certain embodiments at low to non-existent levels of $H_2$ in the gaseous substrate. The gaseous substrate may comprise about 30% or less $H_2$ by volume. In particular embodiments the gaseous substrate comprises about 20% or less $H_2$ by volume, about 15% or less $H_2$ by volume, about 10% or less $H_2$ by volume, about 5% or less $H_2$ by volume, about 4% or less $H_2$ by volume, about 3% or less $H_2$ by volume, about 2% or less $H_2$ by volume, about 1% or less $H_2$ by volume, or substantially no $H_2$.

In certain embodiments the bacteria of the invention are also capable of the productivity, growth rates, alcohol to acid ratio, CO consumption and alcohol tolerance mentioned herein before when supplied with gaseous substrate comprising relatively little $CO_2$. In one embodiment the gaseous substrate comprises less than or equal to about 20% $CO_2$ by volume. In certain embodiments the gaseous substrate comprises less than or equal to about 15% $CO_2$ by volume, less than or equal to about 10% $CO_2$ by volume, or less than or equal to about 5% $CO_2$ by volume. In one particular embodiment, the gaseous substrate comprises substantially no $CO_2$.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and in Klasson et al [(1992). Bioconversion of Synthesis Gas into Liquid or Gaseous Fuels. Enz. Microb. Technol. 14:602-608.], Najafpour and Younesi [(2006). Ethanol and acetate synthesis from waste gas using batch culture of *Clostridium ljungdahlii*. Enzyme and Microbial Technology, Volume 38, Issues 1-2, p. 223-228] and Lewis et al [(2002). Making the connection-conversion of biomass-generated producer gas to ethanol. Abst. Bioenergy, p. 2091-2094]. In particular embodiments of the invention, the minimal anaerobic microbial growth medium is as described herein after in the Examples section.

0106 The invention also provides methods for the production of one or more alcohols from a gaseous substrate comprising CO, the methods comprising maintaining a culture of one or more bacterial isolate of the invention in the presence of the substrate, and the anaerobic fermentation of the substrate to one or more alcohols by the one or more bacterial isolate.

The invention also provides a method for reducing the total atmospheric carbon emissions from an industrial process, the method comprising:
  (a) capturing CO-containing gas produced as a result of the industrial process, before the gas is released into the atmosphere;
  (b) the anaerobic fermentation of the CO-containing gas to produce one or more alcohols by a culture containing one or more bacterial isolates of the invention.

In certain embodiments of the methods of the invention, acetate is produced as a by-product of the fermentation. The alcohol produced is ethanol.

In certain embodiments, the culture is maintained in a liquid nutrient medium.

The fermentation may be carried out in any suitable bioreactor, such as a continuous stirred tank reactor (CTSR), a bubble column reactor (BCR) or a trickle bed reactor (TBR). Also, in some preferred embodiments of the invention, the bioreactor may comprise a first, growth reactor in which the micro-organisms are cultured, and a second, fermentation reactor, to which fermentation broth from the growth reactor is fed and in which most of the fermentation product (ethanol and acetate) is produced.

As described above, the carbon source for the fermentation reaction is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal, electric power production, carbon black production, ammonia production, methanol production and coke manufacturing. In these embodiments, the CO-containing gas may be captured from the industrial process before it is emitted into the atmosphere, using any convenient method. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

In addition, it is often desirable to increase the CO concentration of a substrate stream (or CO partial pressure in a gaseous substrate) and thus increase the efficiency of fermentation reactions where CO is a substrate. Increasing CO partial pressure in a gaseous substrate increases CO mass transfer into a fermentation media. The composition of gas streams used to feed a fermentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

Substrate streams derived from an industrial source are typically variable in composition. Furthermore, substrate streams derived from industrial sources comprising high CO concentrations (such as, for example, at least 40% CO, at least 50% CO or at least 65% CO) often have a low H2 component (such as less than 20% or less than 10% or substantially 0%). As such, it is particularly desirable that micro-organisms are capable of producing products by anaerobic fermentation of substrates comprising a range of CO and H2 concentrations, particularly high CO concentrations and low H2 concentrations. The bacteria of the present invention have a surprisingly high growth rate and ethanol production rate while fermenting a substrate comprising CO (and no H2).

The presence of hydrogen in the substrate stream can lead to an improvement in efficiency of overall carbon capture and/or ethanol productivity. For example, WO02/08438 describes the production of ethanol using gas stream of various compositions. WO02/08438 reports a substrate stream comprising 63% H2, 32% CO and 5% CH4 being provided to a culture of *C. ljungdahlii* in a bioreactor to promote microbial growth and ethanol production. When the culture reached a steady state and microbial growth was no longer the main objective, the substrate stream was switched to 15.8% H2, 36.5% CO, 38.4% N2 and 9.3% CO2 in order to provide CO in a slight excess and promote ethanol production. This document also describes gas streams with higher and lower CO and H2 concentrations.

It will be appreciated that the processes of the present invention as described herein can be used to reduce the total atmospheric carbon emissions from industrial processes, by capturing CO-containing gases produced as a result of such processes and using them as substrates for the fermentation processes described herein.

Alternatively, in other embodiments of the invention, the CO-containing gaseous substrate may be sourced from the gasification of biomass. The process of gasification involves partial combustion of biomass in a restricted supply of air or oxygen. The resultant gas typically comprises mainly CO and $H_2$, with minimal volumes of $CO_2$, methane, ethylene and ethane. For example, biomass by-products obtained during the extraction and processing of foodstuffs such as sugar from sugarcane, or starch from maize or grains, or non-food biomass waste generated by the forestry industry may be gasified to produce a CO-containing gas suitable for use in the present invention.

It is generally preferred that the CO-containing gaseous substrate contains a major proportion of CO. In particular embodiments, the gaseous substrate comprises at least about 25%, at least about 30%, at least about 40%, at least about 50%, at least about 65%, or at least about 70% to about 95% CO by volume. It is not necessary for the gaseous substrate to contain any hydrogen. The gaseous substrate also optionally contains some $CO_2$, such as about 1% to about 30% by volume, such as about 5% to about 10% $CO_2$.

It will be appreciated that for growth of the bacteria and CO-to-ethanol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438 as well as other publications referred to herein before. In one embodiment of the invention the media is as described in the Examples section herein after.

The fermentation should desirably be carried out under appropriate conditions for the CO-to-ethanol fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

The optimum reaction conditions will depend partly on the particular micro-organism of the invention used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

Also, since a given CO-to-ethanol conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

In certain embodiments, a fermentation process according to the present invention described above will result in a fermentation broth comprising ethanol, as well as bacterial cells, in the aqueous culture medium. In preferred embodiments of the method the ethanol is recovered from the fermentation broth.

In certain embodiments, the recovering of ethanol comprises continuously removing a portion of broth and recovering the alcohol from the removed portion of the broth.

In particular embodiments the recovery of ethanol includes passing the removed portion of the broth containing ethanol through a separation unit to separate bacterial cells from the broth, to produce a cell-free alcohol-containing permeate, and returning the bacterial cells to the bioreactor.

In certain embodiments, the methods of the invention are continuous processes.

In particular embodiments, acetate is produced as a by-product of the fermentation.

In a further embodiment the ethanol and the acetate are recovered from the broth.

In certain embodiments, the recovering of ethanol and acetate comprises continuously removing a portion of the broth and recovering separately ethanol and acetate from the removed portion of the broth.

In some embodiments the recovery of ethanol and acetate includes passing the removed portion of the broth containing ethanol and acetate through a separation unit to separate bacterial cells from the ethanol and acetate, to produce a cell-free ethanol- and acetate-containing permeate, and returning the bacterial cells to the bioreactor.

In the above embodiments, the recovery of ethanol and acetate preferably includes first removing ethanol from the cell-free permeate followed by removing acetate from the cell-free permeate. Preferably the cell-free permeate is then returned to the bioreactor.

Ethanol is the preferred desired end product of the fermentation. The ethanol may be recovered from the fermentation broth by methods known in the art, such as fractional distillation or evaporation, and extractive fermentation. Distillation of ethanol from a fermentation broth yields an azeotropic mixture of ethanol and water (i.e. 95% ethanol and 5% water) Anhydrous ethanol can subsequently be obtained through the use of molecular sieve ethanol dehydration technology, which is also well known in the art. Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate may also be recovered from the fermentation broth using methods known in the art. Methods for the recovery of acetate are described in detail in WO2007/117157 and WO2008/115080.

In certain embodiments of the invention, ethanol and acetate are recovered from the fermentation broth by continuously removing a portion of the broth from the fermentation bioreactor, separating microbial cells from the broth (conveniently by filtration), and recovering first ethanol and then acetate from the broth. The ethanol may conveniently be recovered by distillation, and the acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Reaction Stoichiometry

Without wishing to be bound by any theory, the chemical reactions for the fermentation of CO to ethanol (a) and acetic acid (b) in the process of the present invention are believed to be as follows:

$$6CO + 3H_2O \Rightarrow CH_3CH_2OH + 4CO_2 \quad (a)$$

$$4CO + 2H_2O \Rightarrow 1CH_3COOH + 2CO_2 \quad (b)$$

The invention will now be described in more detail with reference to the following non-limiting examples.

EXAMPLES

Materials and Methods

| Solution A | |
|---|---|
| NH$_4$Ac | 3.083 g |
| MgCl$_2$•6H$_2$O | 0.4 g |
| CaCl$_2$•2H$_2$O | 0.294 g |
| KCl | 0.15 g |
| NaCl (optional) | 0.12 g |
| Distilled Water | Up to 1 L |
| Solution B | |
| Biotin | 20.0 mg |
| Folic acid | 20.0 mg |
| Pyridoxine•HCl | 10.0 mg |
| Thiamine•HCl | 50.0 mg |
| Riboflavin | 50.0 mg |
| Nicotinic acid | 50.0 mg |
| Calcium D-(*)-pantothenate | 50.0 mg |
| Vitamin B12 | 50.0 mg |
| p-Aminobenzoic acid | 50.0 mg |
| Thioctic acid | 50.0 mg |
| Distilled water | To 1 Litre |

| Solution C | |
|---|---|
| Component | mmol/L H2O |
| FeCl$_3$ | 0.1 |
| CoCl$_2$ | 0.05 |
| NiCl$_2$ | 0.05 |
| H$_3$BO$_3$ | 0.01 |
| Na$_2$SeO$_3$ | 0.01 |
| Na$_2$MoO$_4$ | 0.01 |
| ZnCl$_2$ | 0.01 |
| MnCl2 | 0.01 |
| Na2WO3 | 0.01 |

Preparation of Cr (II) Solution

A 1 L three necked flask was fitted with a gas tight inlet and outlet to allow working under inert gas and subsequent transfer of the desired product into a suitable storage flask. The flask was charged with $CrCl_3 \cdot 6H_2O$ (40 g, 0.15 mol), zinc granules [20 mesh] (18.3 g, 0.28 mol), mercury (13.55 g, 1 mL, 0.0676 mol) and 500 mL of distilled water. Following flushing with $N_2$ for one hour, the mixture was warmed to about 80° C. to initiate the reaction. Following two hours of stirring under a constant $N_2$ flow, the mixture was cooled to room temperature and continuously stirred for another 48 hours by which time the reaction mixture had turned to a deep blue solution. The solution was transferred into $N_2$ purged serum bottles and stored in the fridge for future use.

Bacteria

The two types of *Clostridium autoethanogenum* used were those deposited at the German Resource Centre for Biological Material (DSMZ) and allocated the accession numbers DSM 19630 and DSM 23693. DSM 23693 was developed from *Clostridium autoethanogenum* strain DSM19630 (DSMZ, Germany) via an iterative selection process.

Sampling and Analytical Procedures

Media samples were taken from the CSTR reactor at intervals over the course of each fermentation. Each time the media was sampled care was taken to ensure that no gas was allowed to enter into or escape from the reactor.

HPLC

HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for Sample Preparation

400 µL of sample and 50 µL of 0.15M $ZnSO_4$ and 50 µL of 0.15M $Ba(OH)_2$ are loaded into an Eppendorf tube. The tubes are centrifuged for 10 min. at 12,000 rpm, 4° C. 200 µL of the supernatant are transferred into an HPLC vial, and 5 µL are injected into the HPLC instrument.

Headspace Analysis

Measurements were carried out on a Varian CP-4900 micro GC with two installed channels. Channel 1 was a 10 m Mol-sieve column running at 70° C., 200 kPa argon and a backflush time of 4.2 s, while channel 2 was a 10 m PPQ column running at 90° C., 150 kPa helium and no backflush. The injector temperature for both channels was 70° C. Runtimes were set to 120 s, but all peaks of interest would usually elute before 100 s.

Cell Density

Cell density was determined by counting bacterial cells in a defined aliquot of fermentation broth. Alternatively, the absorbance of the samples was measured at 600 nm (spectrophotometer) and the dry mass determined via calculation according to published procedures.

Sequencing

Genome sequencing revealed several changes in genomes of *C. autoethanogenum* strain LZ1560 (DSM19630) and new strain LZ1561 (DSM23693), which are likely to contribute to the improved performance.

Both strains were grown anaerobically in PETC media to an optical density ($OD_{600nm}$) of 1 and genomic DNA was isolated from 100 ml overnight cultures. Cells were harvested by centrifugation (6,000×g, 15 min, 4° C.), washed with potassium phosphate buffer (10 mM; pH 7.5) and suspended in 1.9 ml STE buffer (50 mM Tris-HCl, 1 mM EDTA, 200 mM sucrose; pH 8.0). This suspension was treated with 300 µl lysozyme (~100,000 U; 30 min, 37° C.) and 280 µl of a SDS solution (10% (w/v); 10 min). RNA was digested by addition of 240 µl of an EDTA solution (0.5 M; pH 8), 20 µl Tris-HCl (1 M; pH 7.5), and 10 µl RNase A (50,000 U) for 1 hour. Proteolysis was performed by addition of 100 µl Proteinase K (0.5 U) for 1-3 h at 37° C. Finally, 600 µl of sodium perchlorate (5 M) were added, followed by a phenol-chloroform extraction and an isopropanol precipitation. Purity and quantity of DNA was verified using a NanoDrop® 1000 spectrophotometer (Thermo Fisher Scientific, Waltham, Mass., USA) and by gel electrophoresis.

Shotgun genome sequencing was performed using a 454 GS (Roche Applied Science, Indianapolis, Ind., USA). 191,368 single reads with a total length of 44,424,523 bases were created for LZ1560 (10× coverage), while 579,545 paired-end reads with a total length of 202,591,572 bp were created for LZ1561 (47.5× coverage). The reads were assembled using the Newbler package (Roche Applied Science, Indianapolis, Ind., USA) and sequences compared using Geneious (Biomatters Ltd., Auckland, NZ) with the MAUVE package (Darling et al., 2004, *Genome Res.* 14: 1394-1403) and by Artemis Comparison Tool (Carver et al., 2008, *Bioinformatics* 24:2672-6).

Figure 4:
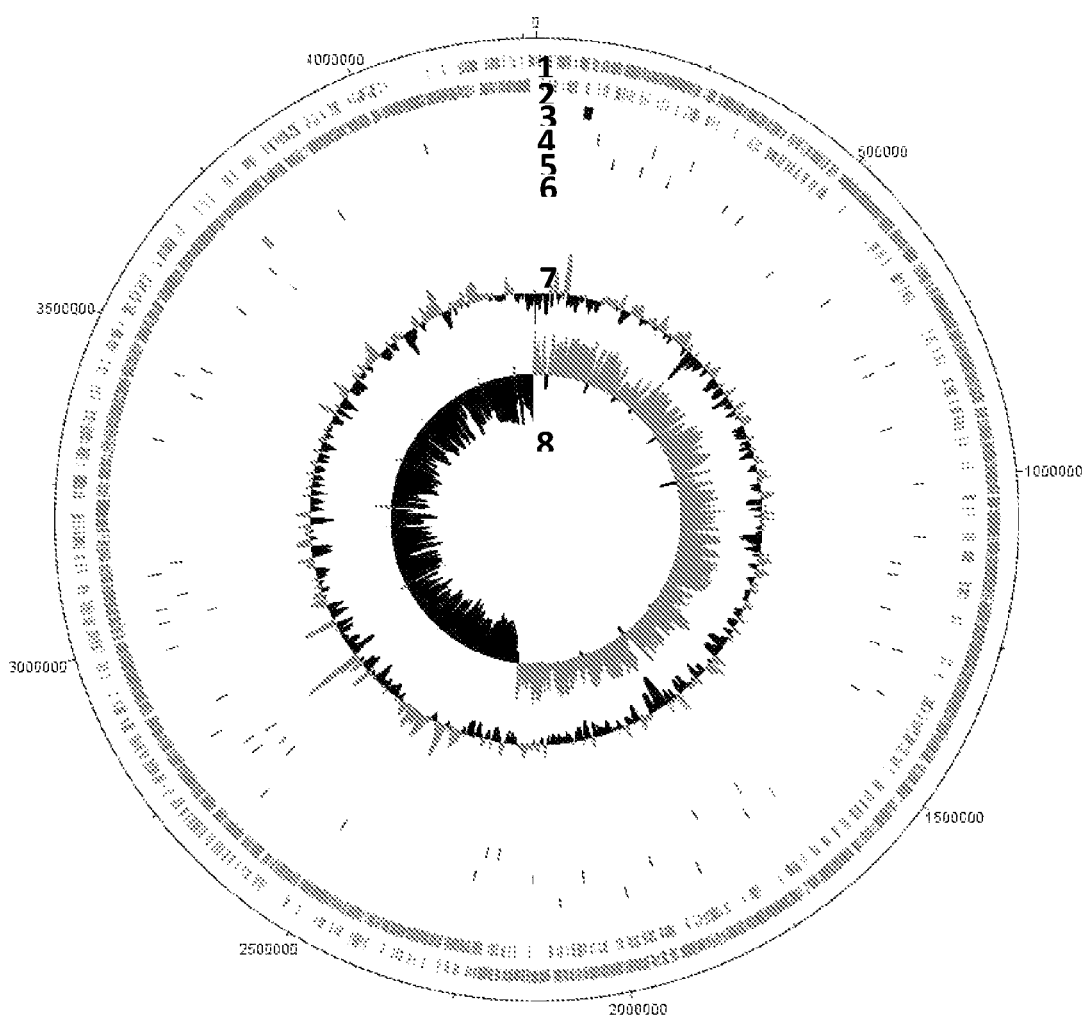
FIG. 4: Shows a genetic map of new *C. autoethanogenum* strain LZ1561 (DSM23693) showing the variations to strain LZ1560 (DSM19630)

A total of 64 changes were found in assembled genome sequences of LZ1560 (DSM19630) and new strain LZ1561 (DSM23693) (FIG. 4). While most changes were single base variations, one 21 bp deletion (in gene encoding a putative DNA mismatch repair protein MutS; SEQ ID NOs: 1-4) and a rearrangement event of a 15,408 bp region (SEQ ID NO: 5) containing 11 genes (involved in nitrogen fixation, sugar metabolism, sugar transport and catabolite control) were found. From the 62 single base variations, 22 were point mutations, and 40 insertions/deletions. 18 of these variations were found in intergenic regions and 44 in coding regions. While 5 of the variations in the coding region were silent and didn't result in a change of amino acid sequence, 14 resulted in a single amino acid change and 25 in a frameshift.

Most notably were changes in positions 212,530 (putative promoter region of $F_1F_O$ ATP synthase operon, SEQ ID NOs: 6-7), 1,171,874 (putative promoter region of Rnf complex operon, SEQ ID NOs: 8-9), 3,717,495 (putative promoter region of carbon starvation protein, SEQ ID NOs: 10-11), and two variations in the Wood-Ljungdahl-gene cluster at positions 3,741,730 (CO dehydrogenase/CO-methylating acetyl-CoA synthase complex beta subunit, SEQ ID NOs: 12-15) and 3,748,058 (5,10-methylenetetrahydrofolate reductase gene, SEQ ID NOs: 16-17), which can be traced back directly to growth on $CO/H_2$ and energy metabolism. Most other genes affected are uncharacterized genes.

Example 1

A: Batch Fermentation in CSTR

Approximately 1500 mL of solution A was transferred into a 1.5 L fermenter and sparged with nitrogen. Resazurin (1.5 mL of a 2 g/L solution) and $H_3PO_4$ (85% solution, 2.25 mL) was added and the pH adjusted to 5.3 using concentrated $NH_4OH(aq)$. Nitrilotriacetic acid (0.3 ml of a 0.15M solution) was added prior to 1.5 ml of solution C. This was followed by $NiCl_2$ (0.75 ml of 0.1M solution) and $Na_2WO_3$ (1.5 mL of a 0.01M solution). 15 ml of solution B was added and the solution sparged with N2 before switching to CO containing gas (50% CO; 28% N2, 2% H2, 20% CO2) at 70 mL/min. The fermenter was then inoculated with 200 ml of a *Clostridium autoethanogenum* 19630 culture. The fermenter was maintained at 37° C. and stirred at 300 rpm. During this experiment, Na2S solution (0.2M solution) was added at a rate of approx 0.3 ml/hour. Substrate supply was increased in response to the requirements of the microbial culture.

Figure 2A:
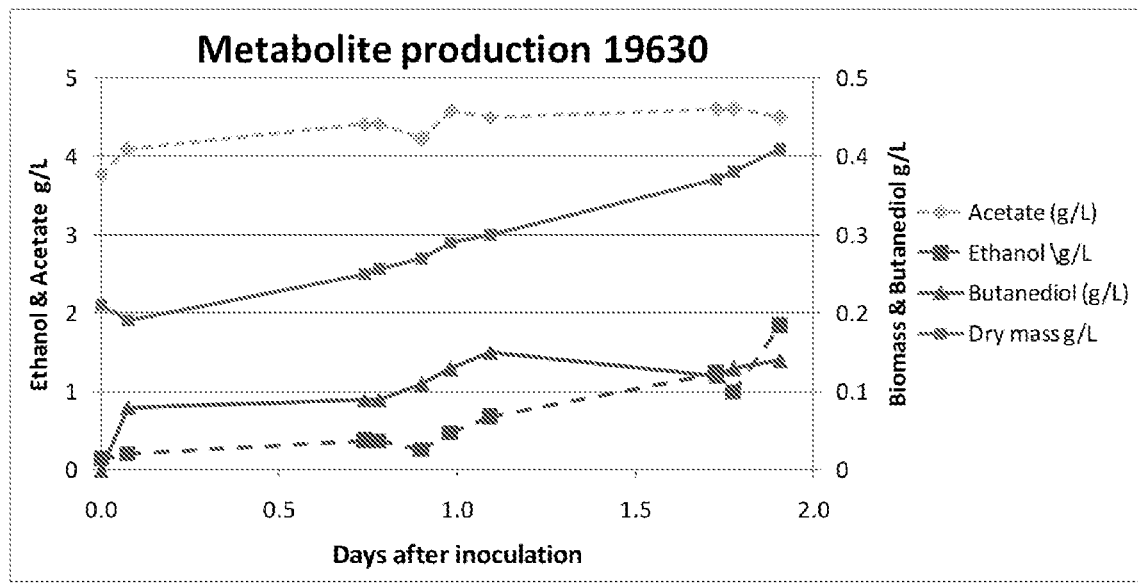
FIG. 2a: Shows the metabolite production of DSM19630.

The bacterial culture did not proliferate in the experimental conditions used. The culture showed a 350 mM CO uptake after 48 hrs of growth (FIG. 1a and Table 2) while the doubling time of the culture was 40.8 hrs (FIG. 2a). This corresponds to a specific growth rate of 0.41 day$^{-1}$. The specific CO uptake increased during the experiment with a maximum value of 0.54 mM CO/min/g biomass. Day 1.0 specific uptake: 0.28 mM CO/min/g biomass (Table 1). Day 2.0 specific uptake: 0.54 mM CO/min/g biomass (Table 2).

B: Batch Fermentation in CSTR

Approximately 1500 mL of solution A was transferred into a 1.5 L fermenter and sparged with nitrogen. Resazurin (1.5 mL of a 2 g/L solution) and $H_3PO_4$ (85% solution, 2.25 mL) was added and the pH adjusted to 5.3 using concentrated $NH_4OH(aq)$. Nitrilotriacetic acid (0.3 ml of a 0.15M solution) was added prior to 1.5 ml of solution C. $Na_2WO_3$ (1.5 mL of a 0.01M solution) was added. 15 ml of Solution B was added and the solution sparged with N2 before switching to CO containing gas (50% CO; 50% N2) at 60 mL/min. The fermenter was then inoculated with 180 ml of a *Clostridium autoethanogenum* 23693 culture. The fermenter was maintained at 37° C. and stirred at 300 rpm. During this experiment, Na2S solution (0.5M solution) was added at a rate of approx 0.12 ml/hour. Substrate supply was increased in response to the requirements of the microbial culture.

Figure 2B:
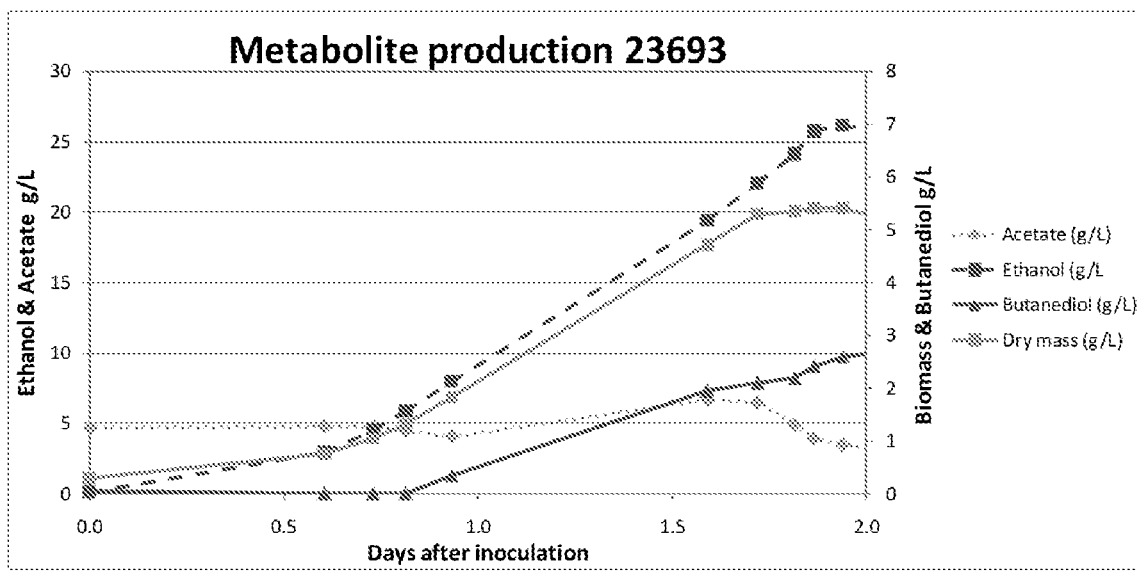
FIG. 2b: Shows the metabolite production of DSM23693
Figure 3:
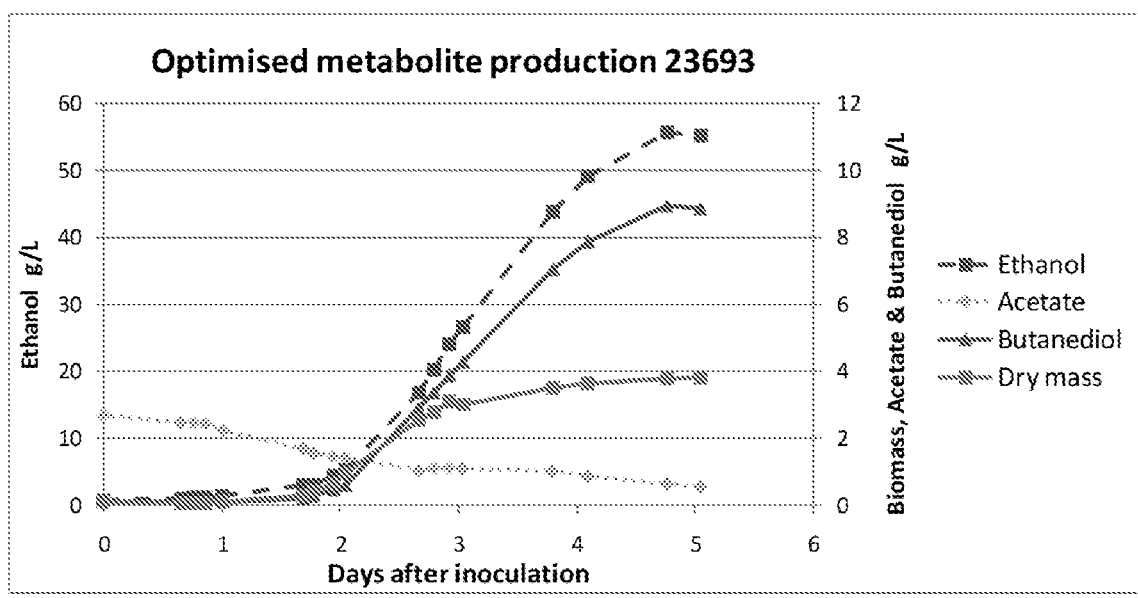
FIG. 3: Shows the optimised biomass accumulation and metabolite production of DSM23693 as described in Example 2.

The bacterial culture proliferated in the experimental conditions used. The culture showed a 8400 mM CO uptake after 43 hrs of growth (FIG. 2b) while the doubling time of the culture was 9.6 hrs (FIG. 2b). This corresponds to a specific growth rate of 1.73 day$^{-1}$. The maximum specific CO uptake reached during the experiment was 1.17 mMol CO/min/g biomass. Day 1.0 specific uptake: 1.17 mM CO/min/g biomass (Table 1). Day 2.0 specific uptake: 1.03 mM CO/min/g biomass (Table 2). The fermentation conditions were identical or at least highly similar to the conditions used in Example 1A. The media preparation has identical components at similar concentrations while both gasses contained CO at least 50% (v/v). The similar fermentation conditions compared to the vast difference in CO uptake indicates the culture performance varied due to the improved efficiency of the developed *Clostridium autoethanogenum* 23693 culture compared to the parent strain *Clostridium autoethanogenum* 19630.

Results

TABLE 1

| | Day 1 | |
|---|---|---|
| Strain | DSM19630 | DSM23693 |
| CO consumption mM/L | 113 mM | 3700 mM |
| Ethanol Production g/L | 0.48 g/L | 7.98 g/L |
| Acetate Production g/L | 4.58 g/L | 4.06 g/L |
| Biomass g/L | 0.29 g/L | 1.83 g/L |
| Specific uptake | 0.28 CO/min/g biomass | 1.17 CO/min/g biomass |
| Specific ethanol production | 2.5 g/L/g biomass/day | 4.3 g/L/g biomass/day |

TABLE 2

| | Day 2 | |
|---|---|---|
| Strain | DSM19630 | DSM23693 |
| CO consumption mM/L | 350 mM | 8150 mM |
| Ethanol Production g/L | 1.84 g/L | 26.14 g/L |
| Acetate Production g/L | 4.5 g/L | 3.47 g/L |
| Biomass g/L | 0.41 g/L | 5.42 g/l |
| Specific uptake | 0.54 CO/min/g biomass | 1.03 CO/min/g biomass |
| Specific ethanol production | 3.0 g/L/g biomass/day | 6.5 g/L/g biomass/day |

Example 2

Approximately 1500 mL of solution A was transferred into a 1.5 L fermenter and sparged with nitrogen. Resazurin (1.5 mL of a 2 g/L solution) and $H_3PO_4$ (85% solution, 0.56 mL) was added and the pH adjusted to 5.3 using concentrated $NH_4OH(aq)$. Solution C (1.5 mL) was added after which $Na_2WO_3$ (1.5 mL of a 0.01M solution) was added. 15 ml of Solution B was added and the solution sparged with $N_2$ before switching to CO containing gas (50% CO; 50% N2) at 60 mL/min. The fermenter was then inoculated with 100 ml of a *Clostridium autoethanogenum* 23693 culture. The fermenter was maintained at 37° C. and stirred at 300 rpm. During this experiment, Na2S solution (0.5M solution) was added at a rate of approx 0.15 ml/hour. Substrate supply was increased in response to the requirements of the microbial culture.

The bacterial culture proliferated in the experimental conditions used. The fermentation conditions were identical or at least highly similar to the conditions used in Example 1A+B while both gasses contained CO at least 50% (v/v). The culture was grown to the stationary phase where maximum ethanol concentration was measured by HPLC (55.8 g/L).

The specific methods and compositions described herein are representative of preferred embodiments and are exemplary and not intended as limitations on the scope of the invention. Other objects, aspects and embodiments will occur to those skilled in the art upon consideration of this specification, and are encompassed within the scope and spirit of the invention. It will be readily apparent to one skilled in the art that varying substitutions and modifications may be made to the invention disclosed herein without departing from the scope and spirit of the invention. The invention illustratively described herein suitably may be practised in the absence of any element or elements, or limitation or limitations, which is not specifically disclosed herein as essential. Thus, for example, in each instance herein, in embodiments or examples of the present invention, the terms "comprising", "including", "containing" etc are to be read expansively and without limitation. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as, an acknowledgment or any form of suggestion that they constitute valid prior art or form part of the common general knowledge in any country in the world.

The invention claimed is:

1. A bacterium derived from *Clostridium autoethanogenum* wherein the bacterium comprises at least one DNA or amino acid sequence selected from SEQ ID NOs: 1, 3, 6, 8, 10, 12, 14, and 16.

2. The bacterium of claim 1, wherein the bacterium is a bacterium deposited under DSMZ accession number DSM23693 or a bacterium derived therefrom.

3. The bacterium of claim 1, wherein the bacterium is derived from *Clostridium autoethanogenum* deposited under DSMZ accession number DSM19630 or naturally occurring *Clostridium autoethanogenum*.

4. The bacterium of claim 1, wherein the bacterium ferments a gaseous substrate to produce one or more products.

5. The bacterium of claim 4, wherein the gaseous substrate comprises one or more of CO, $CO_2$, and $H_2$.

6. The bacterium of claim 4, wherein the products comprise one or more of alcohol and acetate.

7. The bacterium of claim 6, wherein the alcohol is ethanol.

8. A method of producing a product comprising culturing the bacterium of claim 1 in the presence of a gaseous substrate whereby the bacterium produces one or more products.

9. The method of claim 8, wherein the bacterium is a bacterium deposited under DSMZ accession number DSM23693 or a bacterium derived therefrom.

10. The method of claim 8, wherein the bacterium is derived from *Clostridium autoethanogenum* deposited under DSMZ accession number DSM19630 or naturally occurring *Clostridium autoethanogenum*.

11. The method of claim 8, wherein the gaseous substrate comprises one or more of CO, $CO_2$, and $H_2$.

12. The method of claim 8, wherein the products comprise one or more of alcohol and acetate.

13. The method of claim 12, wherein the alcohol is ethanol.

\* \* \* \* \*